US010188744B2

(12) United States Patent
McCarthy et al.

(10) Patent No.: US 10,188,744 B2
(45) Date of Patent: *Jan. 29, 2019

(54) AMPHIPATHIC PEPTIDE

(71) Applicant: The Queen's University of Belfast, Belfast Antrim (GB)

(72) Inventors: Helen McCarthy, Belfast Antrim (GB); Aleksey Zholobenko, Larchwood Staffordshire (GB); Ashley Davison, Belfast Antrim (GB); Tracy Robson, Belfast Antrim (GB)

(73) Assignee: The Queen's University of Belfast, Belfast Antrim (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/688,484

(22) Filed: Aug. 28, 2017

(65) Prior Publication Data
US 2018/0043031 A1    Feb. 15, 2018

Related U.S. Application Data

(63) Continuation of application No. 14/649,606, filed as application No. PCT/EP2013/075985 on Dec. 9, 2013, now Pat. No. 9,744,244.

(30) Foreign Application Priority Data

Dec. 7, 2012  (GB) .................................. 1222041.4

(51) Int. Cl.
| | |
|---|---|
| *A61K 47/64* | (2017.01) |
| *C07K 14/00* | (2006.01) |
| *A61K 31/713* | (2006.01) |
| *A61K 48/00* | (2006.01) |
| *A61K 33/24* | (2006.01) |
| *A61K 38/44* | (2006.01) |
| *A61K 33/42* | (2006.01) |
| *C12N 15/113* | (2010.01) |
| *A61K 47/60* | (2017.01) |
| *C12N 15/87* | (2006.01) |
| *C07K 7/08* | (2006.01) |
| *A61K 47/69* | (2017.01) |

(52) U.S. Cl.
CPC ............ *A61K 47/64* (2017.08); *A61K 31/713* (2013.01); *A61K 33/24* (2013.01); *A61K 33/42* (2013.01); *A61K 38/44* (2013.01); *A61K 47/60* (2017.08); *A61K 47/6455* (2017.08); *A61K 47/6929* (2017.08); *A61K 48/0025* (2013.01); *C07K 7/08* (2013.01); *C07K 14/00* (2013.01); *C07K 14/001* (2013.01); *C12N 15/113* (2013.01); *C12N 15/87* (2013.01); *C07K 2319/00* (2013.01); *C07K 2319/09* (2013.01); *C07K 2319/10* (2013.01); *C07K 2319/33* (2013.01); *C12N 2310/14* (2013.01); *C12N 2310/3513* (2013.01); *C12N 2320/32* (2013.01); *C12Y 114/13039* (2013.01)

(58) Field of Classification Search
CPC ............ A61K 47/6455; A61K 2039/53; A61K 49/0056; A61K 47/62; C12N 2320/32; C12N 2310/3513; C07K 2319/03; C07K 14/195; C07K 14/4723
See application file for complete search history.

(56) References Cited

FOREIGN PATENT DOCUMENTS

| WO | 2002010197 | 2/2002 | |
|---|---|---|---|
| WO | WO2002010197 A1 * | 2/2002 | ............. C07K 14/00 |

OTHER PUBLICATIONS

Zhao et al., "Modification of calcium carbonate based gene and drug delivery systems by a cell-penetrating peptide," Mol. BioSyst., 2012, 8, 3288-3294.
Cohen-Avrahami et al., "Sodium Diclofenac and Cell-Penetrating Peptides Embedded in HII Mesophases: Physical Characterization and Delivery," J. Phys. Chem. B 2011, 115, 10189-10197.
Office Action dated Sep. 23, 2016, in corresponding U.S. Appl. No. 14/649,606, filed Jun. 4, 2015.
McCarthy et al., "Human osteocalcin: a strong promoter for nitric oxide synthase gene therapy, with specificity for hormone refractory prostate cancer," The Journal of Gene Medicine, Mar. 9, 2007, vol. 9, pp. 511-520.

(Continued)

*Primary Examiner* — Marcela M Cordero Garcia
*Assistant Examiner* — Jia-Hai Lee
(74) *Attorney, Agent, or Firm* — Hovey Williams LLP

(57) ABSTRACT

The present invention is directed to an amphipathic peptide and methods of using the amphipathic peptide for delivering small molecule agents to a cell. Ideally, the amphipathic cell penetrating peptide comprises less than approximately 50 amino acid residues with at least 6 arginine residues, at least 12 Alanine Residues, at least 6 leucine residues, optionally at least one cysteine residue, and at least two but no greater than three glutamic acids wherein the arginine residues are evenly distributed along the length of the peptide; and the peptide has a defined ratio of arginine to negatively charged amino acid residues and a defined ratio of hydrophilic amino acid residues to hydrophobic amino acid residues. The present invention is also directed to a nanoparticle and cell delivery system comprising the amphipathic cell penetrating peptide of the invention. The peptide, nanoparticle or cell delivery system of the invention may be used in therapy. For example, the peptide may be used as a therapeutic agent delivery system, in which the therapeutic agent may include nucleic acids or other small molecules.

17 Claims, 51 Drawing Sheets

Figure 1:
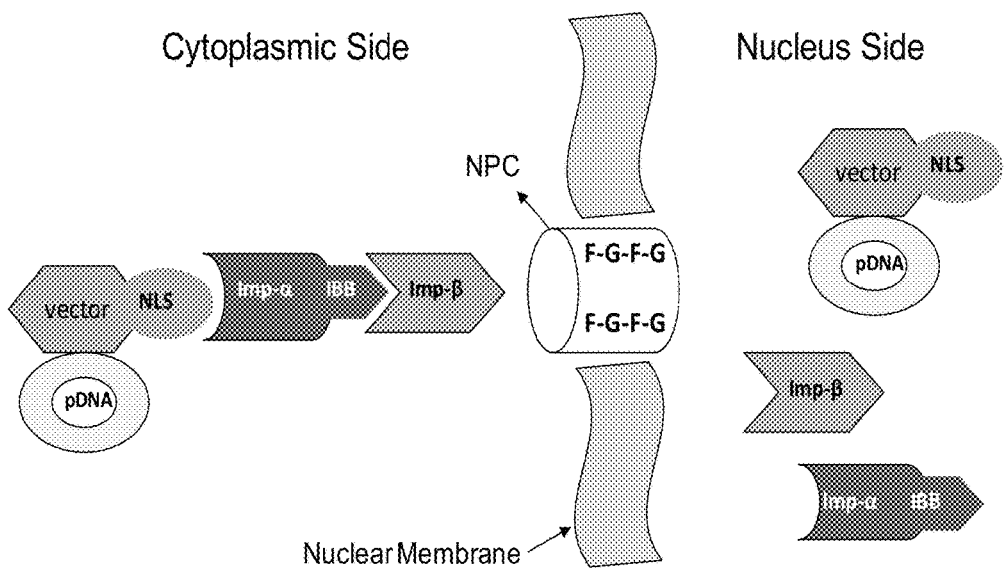

Specification includes a Sequence Listing.

(56) References Cited

OTHER PUBLICATIONS

Mero et al., "Covalent Conjugation of Poly(Ethylene Glycol) to Proteins and Peptides: Strategies and Methods," Bioconjugation Protocols: Strategies and Methods, Methods in Molecular Biology, 2011, Chapter 8, vol. 751, pp. 95-129.
Arai et al., "Design of the linkers which effectively separate domains of a bifunctional fusion protein," Protein Eng., Aug. 2001, vol. 14(8), pp. 529-532.
Yang et al., "TMTP1, a Novel Tumor-Homing Peptide Specifically Targeting Metastasis," Clin. Cancer Res., Sep. 1, 2008, vol. 14(17), pp. 5494-5502.
Liu et al., "Amphipathicity Determines Different Cytotoxic Mechanisms of Lysine- or Arginine-Rich Cationic Hydrophobic Peptides in Cancer Cells," Journal of Medicinal Chemistry, May 19, 2016, vol. 59, pp. 5238-5247.
McCarthy et al., "Development and characterization of self-assembling nanoparticles using a bio-inspired amphipathic peptide for gene delivery," Journal of Controlled Release, Jul. 1, 2014, vol. 189, pp. 141-149.
Ambroggio et al., "Piercing Lipid Bilayers with Peptides," Advances in Planar Lipid Bilayers and Liposomes, vol. 5, Chapter 1, Elsevier Inc., Jan. 1, 2006, pp. 1-23.
Lee et al., "A new gene delivery formulation of polyethylenimine/DNA complexes coated with PEG conjugated fusogenic peptide," Journal of Controlled Release, vol. 76, Sep. 11, 2001, 183-192.
Min et al., "A composite gene delivery system consisting of polyethylenimine and an amphipathic peptide KALA," The Journal of Gene Medicine, vol. 8, No. 12, 2006, 1425-1434.
McCarthy et al., "Evaluation of a multi-functional nanocarrier for targeted breast cancer iNOS gene therapy," International Journal of Pharmaceutics, vol. 405, 2011, 196-202.
Nam et al., "Ion pairs of risedronate for transdermal delivery and enhanced permeation rate on hairless mouse skin," International Journal of Pharmaceutics, vol. 419, 2011, 114-120.
Conde et al., "Design of Multifunctional Gold Nanoparticles for In Vitro and In Vivo Gene Silencing," ACS NANO, vol. 6, No. 9, Aug. 12, 2012, 8316-8324.
Nouri et al., "A Recombinant Biopolymeric Platform for Reliable Evaluation of the Activity of ph-Responsive Amphiphile Fusogenic Peptides," Biomacromolecules, vol. 14, May 17, 2013, 2033-2040.
Ma et al., "Anti-Tumor Effects of the Peptide TMTP1-GG-D(KLAKLAK)2 on Highly Metastatic Cancers," PLOS ONE, vol. 7, Issue 9, Sep. 11, 2012, pp. 1-10.
Wyman et al., "Design, Synthesis, and Characterization of a Cationic Peptide That Binds to Nucleic Acids and Permeabilizes Bilayers," Biochemistry, vol. 36, Jan. 1, 1997, 3008-3017.
International Search Report and Written Opinion dated Feb. 10, 2014, in PCT/EP2013/075985, filed Dec. 9, 2013.
Office Action dated Mar. 18, 2016, in corresponding U.S. Appl. No. 14/649,606, filed Jun. 4, 2015.
Brooks et al., "Tat peptide-mediated cellular delivery: back to basics," Advanced Drug Delivery Reviews 57 (2005) 559-577.
Cohen-Avrahami et al., "HII mesophase and peptide cell-penetrating enhancers for improved transdermal delivery of sodium diclofenac," Colloids and Surfaces B: Biointerfaces 77 (2010) 131-138.
McCaffrey et al., "Selective expression of antigen in Dendritic cells to elicit an antibody response," Experimental Therapeutics, School of Pharmacy, Queen's University Belfast, Mar. 9, 2011, Abstract, 1 page.
Davison et al., "Peptide as a delivery system for optimisation of the antitumour effects of the bisphosphonate alendronate," Experimental Therapeutics, School of Pharmacy, QUB, Mar. 20, 2013, 1 page.
McCaffrey et al., "Delivery of Interleukin-4 gene using a novel amphipathic peptide for the treatment of psoriasis," Experimental Therapeutics Group, School of Pharmacy, Queen's University Belfast, BT9 7BL Northern Ireland, Jul. 20, 2011, Abstract, 1 page.
McCaffrey et al., "Delivery of Interleukin-4 gene using a novel amphipathic peptide for the treatment of psoriasis," Experimental Therapeutics, School of Pharmacy, Queen's University Belfast, Oct. 24, 2011, Poster, 1 page.
Davison et al., "Bio-inspired delivery of RUNX2 siRNA as an adjuvant therapy for metastatic prostate cancer," Experimental Therapeutics Group, School of Pharmacy, Queen's University Belfast, BT9 7BL, Northern Ireland, Jul. 19, 2011, Abstract, 1 page.
McCarthy et al., "DNA Vaccination via Polymeric Microneedles; The use of a Novel Amphipathic Peptide," Experimental Therapeutics, School of Pharmacy, Queen's University Belfast, Northern Ireland, Apr. 15, 2013, Poster, 1 page.
Davison et al., "Characterisation of the RALA Peptide as a Vector to Deliver RUNX2 siRNA," Experimental Therapeutics, School of Pharmacy, QUB, Apr. 9, 2011, Poster, 1 page.
McCarthy, Helen, "A Novel Technology Platform for DNA Vaccine Delivery," Queen's University Belfast, Sep. 2, 2013, 12 pages.

* cited by examiner

Figure 11A-F

Figure 12 A-F

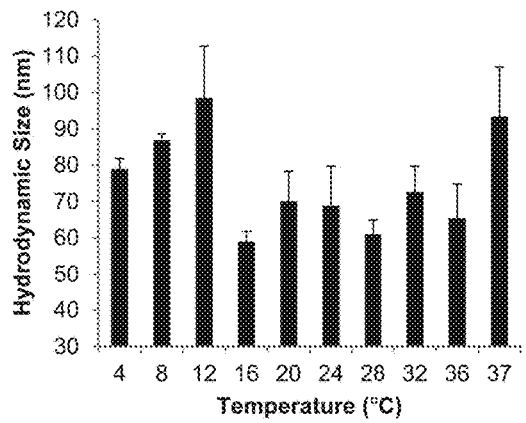
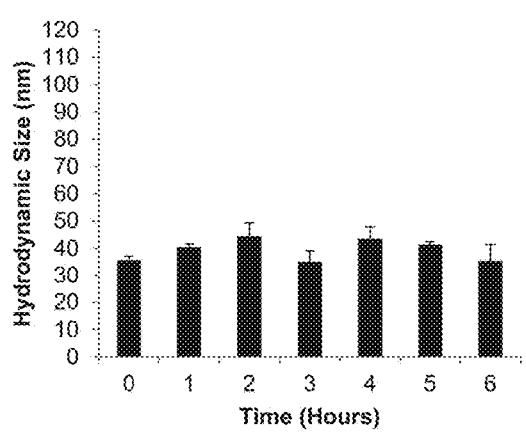
Figure 29A
Figure 29B
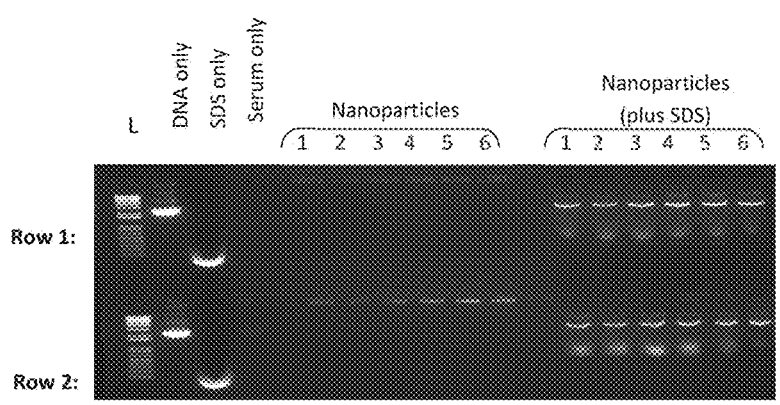
Figure 30

NVVRQLA(EAAAK)⁴AAAWEARLARALARALARHLARALARALRACEA

Targeting Peptide-alpha helical spacer-RALA 25000x          6000x

WEARLARALARALARHLARALARALRACEA-C2-PEG5K

Figure 60

AMPHIPATHIC PEPTIDE

RELATED APPLICATIONS

This application is a continuation of U.S. patent application Ser. No. 14/649,606, filed Jun. 4, 2015 and still pending, which is a national stage application, under 35 U.S.C. § 371, of International Patent Application No. PCT/EP2013/075985, filed Dec. 9, 2013, and published as WO 2014/087023, on Jun. 12, 2014, which claims the priority benefit of Great Britain Patent Application No. 1222041.4, filed Dec. 7, 2012, all of which are hereby incorporated by reference in their entirety.

SEQUENCE LISTING

This application contains a Sequence Listing, submitted as a text file entitled "Sequence$_{13}$ Listing," created on Aug. 1, 2018, as 7 KB, to satisfy both the written copy and computer readable form requirements for Sequence Listings. The content of the Sequence Listing in the text file is hereby incorporated by reference into the application.

INTRODUCTION

The present invention is directed to an amphipathic peptide and methods of using the amphipathic peptide for delivering small molecule agents to a cell. Ideally, the peptide may be used as a therapeutic agent delivery system, in which the therapeutic agent includes nucleic acids or other small molecules.

Gene therapy has the promise to cure almost any disease, provided that we understand its genetic or molecular basis. However, the progress of gene therapy has been impeded by the lack of a suitable delivery vehicle.

There are many barriers to effective delivery of a therapeutic agent to in vivo systems. In order to overcome these delivery barriers, for the systemic administration of therapeutic genes/nucleic acids, a suitable vector for clinical applications should have low cytotoxicity/immunogenicity, high transfection efficiency, tissue specificity and be cost effective.

Gene therapy vectors include viral vectors, such as adenovirus, non-viral vectors such as cationic lipids (DOTAP) or cationic polymers such as polyethlyemine (PEI) and poly-L-Lysine.

Unfortunately, all currently available vectors have significant limitations. For example, although high transfection efficiency can be achieved by lipoplexes there are problems with reproducibility and direct cytotoxicity. Cationic polyplexes are robust and biocompatible but they have poor gene-transfer efficiency. The high efficiency and recombinant engineering possibilities of viral vectors give them the delivery edge, but safety and toxicity issues have limited their use for systemic gene therapy. An ideal delivery system should have the biocompatibility of polyplexes, efficiency of lipoplexes and the engineering capability of viruses.

There are a very low number of commercial gene therapy delivery systems. Most common non-viral systems are those that are used in the laboratory such as Lipofectamine, Oligofectamine, Fugene etc. However, none of these are effective in for in vivo delivery. In terms of polymers, polyethlyemine (PEI) and polylactic-co-glycolic acid (PLGA) have been approved in humans. Both have been approved for parenteral delivery although there are still concerns surrounding the long term toxicity whenever PEI releases its payload and similarly the disadvantage of PLGA is the production of acids upon degradation. Several recombinant viral vectors are in clinical trials with the only one single subject. Gendicine is a recombinant adenovirus engineered to express wildtype-p53 and has been approved by the Chinese State Food and Drug Administration since 2003. Glybera® has also been approved by the European Medical Agency for the treatment of lipoprotein lipase deficiency.

It is also desirable to deliver other agents to a cell, including siRNA, shRNA and other small molecules. RNAi therapies require the nucleic acid to be delivered to either the cytoplasm and/or nucleus of the cell in which the target gene is to be silenced. This is not a straightforward goal to achieve.

An alternative route, to achieve localisation of the agent in the cytoplasm and/or nucleus of the cell, being explored is the use of peptide motifs of diverse biological origins. For example, DNA-condensing peptides such as the Mu peptide or TAT. TAT is very good at cellular entry but does not disrupt endosomes. Other natural and synthetic peptides are also being explored.

Several biological barriers exist both extracellularly and intracellularly. Upon systemic administration the delivery vector must not be degraded in the circulation and must be able to extravasate to surround tissues. Again stability is necessary in the extracellular matrix and the fibrous network of proteins must be navigated. Even when reaching the target tissue cellular entry must be achieved and this is dependent upon charge and size of the particle to be delivered. When foreign particles are endocytosed they become trapped in the endosome which is degraded into a lysozyme. Therefore endosomal escape is critical for successful delivery to the cytoplasm. However several studies have shown that the uptake of DNA into the cytoplasm does not correlate with efficient gene delivery and this is perhaps because the most important barrier is the one to the nucleus. If the final destination site is the nucleus then an active transport system is required otherwise entry into the nucleus is a chance effect during cellular division when the nuclear membrane dissolves. Translocation to the nucleus is dependent on the presence of basic amino acids known as a nuclear localisation signal. The nuclear localisation signal binds to the importin alpha protein which has an importin beta binding domain. The importin beta binding domain then recruits and binds importin beta which will transport the whole complex through the nuclear pore channel through the transient association and disassociation of the phenyalanine-glycine repeats (FIG. 1).

GALA, is a synthetic derivative of the influenza peptide with a Glu-Ala-Leu-Ala repeat that perturbs lipid membranes and forms an aqueous pore. It is an anionic amphiphilic peptide 30 amino acids long and is unable to bind nucleic acids due to their negative charge. It forms an alpha-helical conformation at a low pH of 5.0. GALA cannot condense DNA but can substantially increase the transfection efficiency of standard cationic liposomes. GALA is designed to undergo a pH-dependent conformational change, creates a structure that is capable of penetrating liposomal bilayer membranes causing release of entrapped contents. Thus, GALA is a helper motif to assist with nucleic acid delivery to the cytosol.

Wyman et al in "Design, Synthesis, and Characterization of a Cationic Peptide that Binds to Nucleic Acids and Permeablizes Bilayer" Biochemistry (1997), 36:3008-3017, discloses a low molecular weight cationic amphiphilic peptide, KALA, which mediated nucleic acid delivery and transfection. KALA, has been shown to be excellent at binding and condensing DNA into small nanoparticles and disrupting endosomes and improved gene expression compared to GALA. However, with 50% ethidium bromide displaced from KALA with charge ratios greater than 1 this indicates that KALA is not highly efficient at compacting DNA. The arginine rich Mu sequence can bind DNA within milliseconds. Other studies have shown that arginine rich sequences are required for nuclear uptake (Vives et al 1997).

Cohen-Avrahami et al (J. Phys. Chem. B 2011, 115: 10189-1097 and Colloids and Surfaces B: Biointerfaces 77 (2010) 131-138) discloses an amphipathic peptide that exhibits improved permeability, 16mer RALA. This enables the enhanced delivery of sodium diclofencac (Na-DFC). This is a 16 amino acid sequence that exhibits improved cell membrane permeability. 16mer RALA was developed based on GALA with the addition of Arginine (R) residues. This peptide enhances the permeability of cell membranes to deliver a drug. However, the 16 mer RALA has not been used to deliver nucleic acids nor has it been tested in vivo in terms of stability, degradation or immune response.

TABLE 1

| NAME | AMINO ACID SEQUENCE |
| --- | --- |
| GALA (anionic) | WEAALAEALAEALAEHLAEALAEALEALAA (SEQ ID No. 9) |
| KALA (cationic) | WEAKLAKALAKALAKHLAKALAKALKACEA (SEQ ID No. 10) |
| RALA 16 mer | RALARALARALRALAR (SEQ ID No. 11) |

Thus, the problem of effective delivery of small molecules to a cell to achieve localisation of a therapeutic and other agents in the cytoplasm and/or nucleus of the cell and overcome the many barriers to delivery has not been overcome. Additionally, the need for new and improved vectors for gene therapy remains. The present invention is directed to these problems.

STATEMENTS OF THE INVENTION

According to a general aspect of the invention, there is provided an amphipathic cell penetrating peptide less than approximately 100 amino acid residues, preferably less than approximately 80 amino acid residues, more preferably less than approximately 70 amino acid residues, even more preferably less than approximately 60 amino acid residues, most preferably less than approximately 50 amino acid residues comprising or consisting of at least 6 arginine residues (R), at least 12 Alanine Residues (A), at least 6 leucine residues (L), optionally at least one cysteine residue (C) and at least two but no more than three glutamic acids (E).

Optionally, the amphipathic cell penetrating peptide of the invention does not comprise glycine (G). It will be understood that the peptide of the invention is a pH-dependant fusogenic peptide. The peptide of the invention is cationic and arginine-rich. Furthermore, it will be understood that the amphipathic cell penetrating peptide of the present invention in use complexes to nucleic acids or other agents to form a nanoparticle which penetrates a cell.

The amphipathic cell penetrating peptide may comprise less than or equal to approximately 55, 50, 40, 45, 40, 35, 34, 33, 32, 31, 30, 29, 28, 27, 26, 25, 24 amino acid residues. Ideally, the amphipathic cell penetrating peptide comprises 30, 29, 28, 27, 26, 25, 24 or 23 amino acids residues. Ideally, the peptide has greater than 16 amino acid residues, preferably greater than 23 amino acid residues, more preferably 23 amino acid residues or more.

Ideally, the arginine (R) residues are evenly distributed along the length of the peptide; and/or the ratio of arginine (R) to negatively charged amino acid residues glutamic acid (E) is from at least 6:2 to 9:2 or 8:2; and/or the ratio of hydrophilic amino acid residues to hydrophobic amino acid residues at pH 7 is at least 30:70 or 30:67 to 40:60. Optionally, the ratio of arginine (R) to negatively charged amino acid residues glutamic acid (E) is a minimum of 2 to a maximum of 4.

According to one aspect of the invention, there is provided an amphipathic cell penetrating peptide of less than approximately 50 amino acid residues, preferably less than approximately 40 amino acid residues, preferably less than or equal to 30 amino acid residues, more preferably less than or equal to 29 amino acid residues, comprising or consisting of at least 6 arginine residues (R), at least 12 Alanine Residues (A), at least 6 leucine residues (L), optionally at least one cysteine residue (C) and at least two but no more than three glutamic acids (E) wherein
a. the arginine (R) residues are evenly distributed along the length of the peptide;
b. the ratio of arginine (R) to negatively charged glutamic acid (E) amino acid residues is from at least 6:2 to 9:2 or 6:2 to 8:2; and/or
c. the ratio of hydrophilic amino acid residues to hydrophobic amino acid residues at pH 7 is at least 30:70 to 40:60 or 30:67 to 40:60.

According to a second aspect of the invention, there is provided an amphipathic cell penetrating peptide less than approximately 50 amino acid residues, preferably less than approximately 40 amino acid residues, preferably less than or equal to 30 amino acid residues, more preferably less than or equal to 29 amino acid residues, comprising or consisting of at least 6 arginine residues (R), at least 12 Alanine Residues (A), at least 6 leucine resiues (L), optionally at least one cysteine residue (C) and at least two but no more than three glutamic acids (E) wherein the peptide comprises the consensus sequences EARLARALARALAR (SEQ ID No. 15) and/or LARALARALRA (SEQ ID No. 16).

According to a third aspect of the invention, there is provided an amphipathic cell penetrating peptide less than approximately 50 amino acid residues, preferably less than approximately 40 amino acid residues, preferably less than or equal to 30 amino acid residues, more preferably less than or equal to 29 amino acid residues, comprising or consisting of at least 6 arginine residues (R), at least 12 Alanine Residues (A). at least 6 leucine resiues (L), optionally at least one cysteine residue (C) and at least two but no more than three glutamic acids (E) wherein the peptide comprises the consensus sequences EARLARALARALAR (SEQ ID No. 15) and LARALARALRA (SEQ ID No. 16).

According to a fourth aspect of the invention, there is provided an amphipathic cell penetrating peptide less than approximately 50 amino acid residues, preferably less than approximately 40 amino acid residues, preferably less than or equal to 30 amino acid residues, more preferably less than or equal to 29 amino acid residues, comprising or consisting of at least 6 arginine residues (R), at least 12 Alanine Residues (A), at least 6 leucine resiues (L), optionally at least one cysteine residue (C) and at least two but no more than three glutamic acids (E) wherein the peptide comprises the amino acid sequence X-EARLARALARALAR-Y-LARALARALRA-Z-EA (SEQ ID No. 17), wherein X is W or R; Y is optional or selected from H or E; and Z is C or R, or a sequence with at least 99%, 98%, 97%, 96%, 95%, 94%, 93%, 92%, 91%, 90%, 85%, 80% sequence identity or homology.

The present invention is also directed to modified peptides or peptide derivatives. For example, the peptide of the invention may be coupled or conjugated to a polyethylene glycol (PEG) molecule. Alternatively, the peptide of the invention may comprise a cell targeting motif, preferably to confer specificity to metastatic cell lines, conjugated to the peptide through or via a spacer sequence, preferably an alpha helical spacer.

According to a fifth aspect of the invention, there is provided a nanoparticle or cell delivery system comprising the peptide of any the invention complexed with a nucleic acid or other agent, preferably a negatively charged or hydrophilic compound.

According to a sixth aspect of the invention, there is provided the use of the peptide, nanoparticle or cell delivery system according to the invention for the delivery, preferably nuclear localisation, of nucleic acids to cells.

According to a seventh aspect of the invention, there is provided a peptide, nanoparticle or cell delivery system according to the invention for use in therapy, preferably gene therapy.

According to a eighth aspect of the invention, there is provided the use of the peptide, nanoparticle or cell delivery system according to the invention to improve the bioavailability of a phosphate based drug, preferably a bisphosphonate drug.

According to a ninth aspect of the invention, there is provided the use of the peptide, nanoparticle or cell delivery system according to the invention to improve the cellular uptake of gold.

According to a tenth aspect of the invention, there is provided the use of a peptide, nanoparticle or cell delivery system according to the invention in the manufacture of medicament for use in therapy, preferably gene therapy.

According to an eleventh aspect of the invention, there is provided a method of treating an individual in need of gene therapy comprising the administration of the peptide, nanoparticle or cell delivery system according to the invention, complexed with a nucleic acid or other agent to an individual in need thereof.

According to a twelfth aspect of the invention, there is provided a method of improving the bioavailability of a phosphate based drug, comprising the administration of the peptide, nanoparticle or cell delivery system according to the invention complexed with a phosphate based drug, preferably a bisphosphonate drug, to an individual in need thereof.

According to a thirteenth aspect of the invention, there is provided a method of improving the cellular uptake of gold in an individual comprising the administration of the peptide, nanoparticle or cell delivery system according to the invention complexed with gold to an individual.

According to a fourteenth aspect of the invention, there is provided a pharmaceutical composition comprising the a peptide, nanoparticle or cell delivery system according to the invention and a pharmaceutically acceptable excipient.

DETAILED DESCRIPTION

According to a general aspect of the invention, there is provided an amphipathic cell penetrating peptide comprising or consisting of an amphipathic cell penetrating peptide less than approximately 50 amino acid residues comprising at least 6 arginine residues (R), at least 12 Alanine Residues (A), at least 6 leucine residues (L), optionally at least one cysteine residue (C) and at least two but no more than three glutamic acids (E) wherein a. The arginine (R) residues are evenly distributed along the length of the peptide;
b. the ratio of arginine (R) to negatively charged amino acid residues glutamic acid (E) is from at least 6:2 to 9:2 or 6:2 to 8:2; and/or
c. the ratio of hydrophilic amino acid residues to hydrophobic amino acid residues at pH 7 is at least 30:70 to 40:60 or 30:67 to 40:60.

We have found that the presence of arginine (R) residues in the amphipathic cell penetrating peptide is essential. Ensuring an even distribution of arginine (R) residues along the length of the peptide facilitates delivery of the peptide across a cell membrane by condensing the negatively charged compound or nucleic acid through electrostatic interactions. The presence of arginine (R) enables nanoparticles less than 20 nm to form and ensures a positive zeta potential which enables internalisation into the cell. We have also found that the presence of arginine (R) residues also enhances nuclear localisation.

The ratio of the positively charged amino acid residues arginine (R) to negatively charged amino acid is also important because this is necessary to condense the payload into nanoparticles through electrostatic interactions. It is generally accepted that a nanoparticle less than <200 nm will be small enough to cross the cell membrane. In addition, the ratio of positively charged residues ensures an overall positively charged nanoparticle which has two main advantages. Firstly, that the particles will not aggregate and repel each other which aids in systemic delivery otherwise embolisms could occur. Secondly, as the cell membrane is negatively charged, nanoparticles that are either neutral or mildly positively charged will not enter the cell.

Finally, the peptide has a greater proportion of hydrophobic residues than hydrophilic residues (see table below) because this enables an amphipathic helical conformation and when the pH lowers in the endosome it is likely that RALA undergoes a conformational change to a mixture of alpha helix and random coil. This conformational change exposes the hydrophobic residues that can then fuse and destabilize the endosomal membrane enabling release to the cytosol. Having more hydrophobic residues increases the extent of membrane destabilisation.

| | ph7 | Polar/ Non-Polar | Hydrophilic | Hydrophobic |
| --- | --- | --- | --- | --- |
| R - Arg | Positive | Polar | Yes | |
| W - Trp | | Non-Polar | | Yes - very |
| E - Glu | Negative | Polar | Yes | |
| L- Leu | | Non-Polar | | Yes - very |
| A - Ala | | Non-Polar | | Yes - mildly |
| H - His | Positive | Polar | Yes | |
| C-Cys | Slightly Negative | Partially Polar | | Yes - mildly |

As shown in the Examples, we have surprisingly found that the peptide of the invention has improved cell penetration activity compared to, for example, KALA for DNA delivery and conventional transfection reagents such as Oligofectamine® for siRNA delivery. Advantageously, the peptide of the invention is less toxic than another conventional transfection reagent such as, for example, Lipofectamine 2000®.

According to a preferred embodiment of the invention, the arginine (R) residues are evenly distributed at every third and/or fourth amino acid position along the entire length of the peptide.

According to another preferred embodiment of the invention, the amount of hydrophilic amino acid residues in the peptide should not exceed approximately 40% or 37% and the ratio of hydrophilic amino acid residues to hydrophobic amino acid residues ratio at pH 7 is from 30:67 to 40:60, preferably 30:70 to 37:63.

According to another embodiment of the invention, the peptide comprises less than approximately 40 amino acid residues. Optionally, the peptide comprises 35, 34, 33, 32, 31, 30 amino acid residues, preferably 30, 29, 28, 27, 26, 25, 24 or 23 amino acid residues.

Ideally, the peptide comprises the consensus sequence EARLARALARALAR (SEQ ID No. 15).

Optionally, the peptide may comprise the consensus sequences EARLARALARALAR (SEQ ID No. 15) and/or LARALARALRA (SEQ ID No. 16) as highlighted in the preferred sequences according to the invention listed below;

WEARLARALARALARHLARALARALRACEA (SEQ ID No. 1)

WEARLARALARALARLARALARALRACEA (SEQ ID No. 2)

WEARLARALARALARLARALARALRACEA (SEQ ID No. 3)

WEARLARALARALARELARALARALRACEA (SEQ ID No. 4)

REARLARALARALARLARALARALRACEA (SEQ ID No. 5)

REARLARALARALARLARALARALRAREA (SEQ ID No. 6)

REARLARALARALARELARALARALRAREA (SEQ ID No. 7)

Ideally, the present invention provides a peptide comprising the amino acid sequence X- EARLARALARALAR-Y-LARALARALRA-Z-EA (SEQ ID No. 17)

or a sequence at least 99%, 98%, 97%, 96%, 95%, 94%, 93%, 92%, 91%, 90%, 85%, 80% identical, wherein
X is W or R;
Y is optional and if present is selected from H or E; and
Z is C or R.

Preferably, the peptide comprises or consists of one of the following amino acid sequences:

WEARLARALARALARHLARALARALRACEA (SEQ ID No. 1)

WEARLARALARALARLARALARALRACEA (SEQ ID No. 2)

WEARLARALARALARLARALARALRACEA (SEQ ID No. 3)

WEARLARALARALARELARALARALRACEA (SEQ ID No. 4)

REARLARALARALARLARALARALRACEA (SEQ ID No. 5)

REARLARALARALARLARALARALRAREA (SEQ ID No. 6)

REARLARALARALARELARALARALRAREA (SEQ ID No. 7)

or a fragment thereof. Ideally, the fragment comprises at least 23 amino acids from SEQ ID Nos. 1 to 7.

Table 2 below provides further details of the several different examples amino acid sequences of preferred amphipathic cell penetrating peptides listed above.

TABLE 2

| Amino Acid Residue Sequence | SEQ ID No. | Length | % Ratio of Hydrophilic: Hydrophobic: Neutral amino acid residues | +/− charged amino acid residues |
|---|---|---|---|---|
| "RALA"<br>1. WEARLARALARALARHLARALARALRACEA | 1 | 30 mer | 30:67:1 | 8:2 |
| H removed<br>2. WEARLARALARALARLARALARALRACEA | 2 | 29 mer | 31:70 | 7:2 |
| H replaced with glutamic acid (E)<br>3. WEARLARALARALARELARALARALRACEA | 4 | 30 mer | 33:67 | 7:3 |
| H Removed and W replaced with R<br>4. REARLARALARALARLARALARALRACEA | 5 | 29 mer | 34:66 | 8:2 |
| H Removed and W replaced with R and C replaced with R<br>5. REARLARALARALARLARALARALRAREA | 6 | 29 mer | 37:63 | 9:2 |
| H Replaced with E and W replaced with R and C replaced with R<br>6. REARLARALARALARELARALARALRAREA | 7 | 30 mer | 40:60 | 9:3 |
| 7. WEARLARALARALARHLRACEA (comparative peptide) | 8 | 22 mer | | |

A most preferred sequence comprises/consists of the amino acid sequence WEARLARALARALARHLARAL-ARALRACEA (herein referred to as "RALA") (SEQ ID No. 1).

It will be understood, in this specification "RALA" is a generic term referring to the RALA sequence (SEQ ID No. 1) or other similar sequences, including but not limited to SEQ ID Nos. 2 to 7, which also fall within the scope of the invention.

The invention also encompasses sequence with at least 90%, 95%, 96%, 97%, 98% or 99% sequence identity or sequence homology with SEQ ID Nos. 1 to 7.

Advantageously, the claimed amphipathic cell penetrating peptides of the invention consist of arginine/alanine/leucine/alanine repeats that result in a specifically tailored hydrophobic and hydrophilic region facilitating interaction with the lipid bilayers enabling transport of the peptide across cellular membranes. As stated above, the presence of arginine (R) residues is an essential feature of the claimed peptide. There are two main advantages of using arginine. Firstly, arginine has consistently been shown to be the optimal amino acid for condensing DNA with arginine rich sequences binding in milliseconds. Secondly, arginine rich sequences based on the Rev sequence have the capacity to actively transport DNA into the nucleus of cells via the importin pathway (see FIG. 1).

In addition, there must be at least 2, but no more than 3, glutamate residues (E) to ensure pH-dependent solubility and protonation which facilitates endosomal disruption.

The present invention is also directed to modified peptides or peptide derivatives.

Optionally, the peptide according to any of the preceding claims is coupled or conjugated to a polyethylene glycol (PEG) molecule, such as RALA-PEG. Preferably, coupling takes place at the C-terminus of the peptide. The presence of the PEG molecule is advantageous because it increases circulation time of the peptide in vivo and provides for an enhanced permeation and retention effect of the peptide.

Alternatively, the peptide of the invention may comprise a cell targeting motif, preferably a motif which confers specificity to metastatic cell lines, conjugated to the N-terminus of the peptide through or via a spacer sequence. Ideally, the spacer sequence is an alpha helical spacer.

In this manner, the cell targeting motif may be the metastatic prostate cancer targeting peptide TMTP-1 (NV-VRQ) SEQ ID No. 12) and the spacer may be an alphabetical concatemeric spacer, preferably comprising 1 or more, preferably, 2, 3, or 4 repeats of the sequence EAAAK (SEQ ID No. 13).

Advantageously, we have found that the claimed amphipathic cell penetrating peptide (RALA and similar sequences) or modified peptide/peptide derivative facilitates nuclear localisation. This gives the amphipathic cell penetrating peptide of the invention a distinct advantage over conventional non-viral and viral delivery systems. Surprisingly, the claimed amphipathic cell penetrating peptide has also been shown to form nanoparticles after 5 mins and be stable up to 48 hours at room temperature. The peptides of the present invention have been found to be stable as nanoparticles up to 5, 6 and 15 days after delivery.

Advantageously, we have found that the claimed amphipathic cell penetrating peptide can create nanoparticles with a size less than 150 nm or even 100 nm with nucleic acids or other agents. This facilitates transport of these agents across cell membranes, out of the endosomes and to the nucleus. We have found that these nanoparticles are stable in serum and over a temperature range of 4 to 37° C.

According to another aspect of the invention, there is provided a nanoparticle comprising the peptide of the invention complexed or condensing with a nucleic acid or other agent, preferably a negatively charged or hydrophilic compound. In this specification, it will be understood the terms "complexed" and "condensing" are interchangeable.

Advantageously, the peptide of the invention condenses the nucleic acid or other agent.

According to one embodiment, the peptide of the invention may be complexed with a nucleic acid, preferably DNA or siRNA, to form discrete spherical nanoparticles, each nanoparticle with a diameter less than approximately 150 nm, preferably less than or equal to 100 nm.

According to another embodiment, the nanoparticles may have a N:P ratio greater than 2, preferably greater than 4.

According to another aspect of the invention, there is provided a cell delivery system comprising the peptide of the invention complexed or condensing with a nucleic acid or other agent, preferably a negatively charged or hydrophilic compound.

This delivery system is applicable across a wide range of nucleic acids, including DNA, RNA, siRNA and shRNA, and other agents, preferably small molecule agents.

According to another aspect of the invention, there is provided use of the peptide, nanoparticle or cell delivery system according to of the invention for the delivery, preferably nuclear localisation, of nucleic acids to cells, either in-vitro or in-vivo.

According to a preferred embodiment, the nanoparticle or cell delivery system of the invention is complexed with a hydrophilic compound when used for the delivery of nucleic acids to cells, either in-vitro or in-vivo.

It will be understood that the nucleic acid may be selected from one or more of DNA, RNA, shRNA, and siRNA.

According to a preferred embodiment, the nucleic acid is siRNA or shRNA and may inhibit the expression of a disease causing gene.

Preferably, the nanoparticles comprise the claimed amphipathic cell penetrating peptide and siRNA, and hence act as a siRNA transfection agent. With siRNA we have shown a much higher level of cellular entry compared to commercially available transfection reagents e.g. Oligofectamine®. In-vivo tests have shown that successful gene delivery following systemic injection into the bloodstream. Importantly, repeated injection of the RALA nanoparticles does not illicit a significant immune response, either adaptive (IgG or IgM) or inflammatory (IL-6, Il-1b). Furthermore we have shown that the there is no neutralisation of the claimed amphipathic cell penetrating peptide following systemic delivery. This is another major advantage of the claimed amphipathic cell penetrating peptide.

Accordingly, the peptide as defined above presents a viable alternative in the field of gene delivery and may be used as a transfection agent for siRNA.

According to this embodiment, the claimed amphipathic cell penetrating peptide may also be used in DNA gene therapy. Confocal imaging has clearly shown delivery of Cy3 labelled DNA to the nucleus of prostate cancer cells. This provides the opportunity for the delivery of any nucleic acid to a cell in vivo, in which the nucleic acid may be utilised for gene therapy.

The nucleic acid may encode a functional, therapeutic gene to replace a mutated gene. Alternatively, the nucleic acid may correct a mutation or encodes a therapeutic protein drug. In this manner, the nanoparticles of the invention may be used as adjuvant gene therapy treatment administered optionally prior to conventional treatments.

According to another embodiment of the invention, the nucleic acid may be DNA in the form of an iNOS (inducible nitric oxide synthase) plasmid DNA under control of a tumour specific promoter. The iNOS plasmid DNA may be condensed with or complexed with the peptide of the invention to form nanoparticles and delivered as nanoparticles in-vivo. This results in the inducible production of nitric oxide in-vivo which is detrimental to tumour metastasis. In this manner, the nanoparticles or cell delivery system of the invention comprise the claimed amphipathic cell penetrating peptide and iNOS plasmid DNA.

According to one embodiment the tumour specific promoter is the human osteocalcin (hOC) promoter. It will be understood that the hOC promoter is specific to ovarian, breast and prostate cancers and although the peptide of the invention will deliver to all tissues the use of this promoter will ensure transcriptional targeting and expression of the desired gene only in the tumours. However, other known promoters may be used which will be dependent on differential expression in tumour tissue. Examples include the osteopontin promoter known to be overexpressed in breast cancer, the prostate specific membrane antigen promoter for prostate cancer or radiation inducible promoters such as WAF1 or CARG. Both WAF1 and CARG have the added advantage of also being activated in hypoxic regions such as those found in the centre of tumours.

According to another embodiment of the invention, the tumour specific promoter may be a prostate specific promoter, such as the prostate membrane specific antigen promoter (PSMA).

The amphipathic cell penetrating peptide of the invention may also be used to deliver hOC-iNOS (inducible nitric oxide synthase) systemically in vivo to any tumour model that has been shown to metastasize to bone. In this manner iNOS plasmid DNA may be condensed with the peptide of the invention and delivered as nanoparticles in-vivo. Advantageously, the RALA/hOC-iNOS nanoparticles may be administered in tandem with the current recommended chemotherapy regimen of docetaxel. For those with bone metastases docetaxel remains the standard front-line treatment but increasingly many patients develop resistance to this drug. This new combination therapy provides an alternative strategy for treating bone metastases.

Alternatively, promoters specific for cardiovasculature may be used to increase the levels of iNOS to dilate blood vessels. One potential administration method includes the application of the nanoparticles as a coating for stents. A major unresolved issue following percutaneous transluminal coronary angioplasty (PTCA) is the physical injury to the blood vessel wall, which leads to vessel re-occlusion, i.e. restenosis. The endothelial denudation associated with this injury is accompanied by varying degrees of medial disruption and is followed by an inappropriate response-to-injury of vascular smooth muscle. Therefore using smooth muscle cell (SMC) (e.g. SM22 alpha promoters) promoters to drive expression of the iNOS transgene will confer tissue specific targeting at the site of injury either with or without stents.

Other uses may also be contemplated for delivery of agents, preferably small molecule agents. These include but are not limited to any phosphate or lipophilic based drug, preferably a bisphosphonate drug and gold. Bisphosphonate drugs are characterised by a very low bioavailability, rapid excretion from the body, harsh side effects and poor patient compliance. Improving upon the delivery of this drug to where it is needed there provides a significant impact on patient health. As a lipophilic drug bisphosphonates cannot cross the cell membrane to effect the therapy. Therefore there is a need for an effective delivery system to encapsulate the bisphosphonates and improve cellular entry and bioavailability in vivo.

The agent may be a small molecule agent, such as a therapeutic agent or drug. The therapeutic agent may be a phosphate based drug, preferably a bisphosphonate drug including alendronate, etidronate, zolendrate or any other nitrogen or non-nitrogen based bisphosphonate drug. Bisphosphonate drugs have low bioavailability which can advantageously be enhanced when complexed with the peptide of the present invention.

According to another aspect of the invention, there is provided the use of the peptide, nanoparticle or cell delivery system according to the invention to improve the bioavailability of a phosphate based drug, preferably a bisphosphonate drug.

We have also shown that the peptide of the invention has potential to increase the bioavailability of bisphosphonate drugs. The peptide of the invention may be used for the condensation and delivery of the nitrogen bisphosphonate, Alendronate. N-BP nanoparticles were formed with sizes less than 100 nm and an overall positive charge facilitating cellular entry. The alendronate nanoparticles were spherical, uniform and did not aggregate as evidenced by TEM. More importantly, when the alendronate loaded nanoparticles were added to prostate cancer cells in vitro there was significantly greater cytotoxicity at lower concentrations compared to the alendronate only treated cells. Thus, the delivery system of the invention provides significant promise for improving the delivery and bioavailability of bisphosphonates patients with osteoporosis and cancer.

An alternative use involves the improvement of the delivery of gold particles. The effectiveness of many radiotherapy treatment plans are limited by normal tissue toxicity. Using gold nanoparticles (GNPs) can increase the therapeutic benefit by radiosensitizing cancer cells. However whenever these gold nanoparticles are delivered the majority remain trapped within the endosome creating an inhomogeneous distribution and limiting their full potential. We have found that when the GNPs are wrapped with the peptide of the invention there is a significant increase in endosomal escape which facilitates a marked increase in therapeutic efficacy.

Thus, according to yet another embodiment of the invention the agent may be gold. This can be useful as gold can be used as a radiosensitizers when it gets to the nucleus of cells and this is facilitated when complexed with the peptide of the present invention.

In this manner, according to another aspect of the invention, there is provided the use of the peptide, nanoparticle or cell delivery system according to the invention to improve the cellular uptake of gold.

Alternatively, the agent may be a therapeutic drug, comprising any conventional drug.

Thus, according to this aspect of the invention, the peptide, nanoparticle or cell delivery system according to the invention may be used for the delivery of nucleic acids or other agents to cells.

Administration of the peptide, nanoparticle or cell delivery system may be carried out via a variety of routes including, but not limited to, oral, topical, pulmonary, rectal, subcutaneous, intradermal, intranasal, intracranial, intramuscular, intraocular, or intra-articular injection, and the like.

Ideally delivery is by intravenous, intradermal, subcutaneous, intraperitoneal, intramuscular or transdermal delivery of the peptide, nanoparticle or cell delivery system to a patient. The most typical route of administration is intravenous followed by subcutaneous, although other routes can be equally effective.

In this manner, the peptide, nanoparticle or cell delivery system of the invention may be administered as injectable dosages of a solution or suspension of the peptide, nanoparticle or cell delivery system in a physiologically acceptable diluent or adjuvant with a pharmaceutical carrier that can be a sterile liquid such as water, oils, saline, glycerol, or ethanol. Such pharmaceutically acceptable adjuvants include carriers, diluents, and excipients such as sterile water and oil. Additionally, auxiliary substances, including but not limited to wetting or emulsifying agents, surfactants, pH buffering substances and the like can be provided with the peptide, nanoparticle or cell delivery system of the invention. Other components may include those of petroleum, animal, vegetable, or synthetic origin, for example, peanut oil, soybean oil, and mineral oil. In general, glycols such as propylene glycol or polyethylene glycol are suitable liquid carriers, particularly for injectable solutions.

Optionally, the peptide, nanoparticle or cell delivery system may be delivered systemically, locally or parenterally. Oral formulations take the form of solutions, suspensions, tablets, pills, capsules, sustained-release formulations or powders. Topical application can result in transdermal or intradermal delivery. Local delivery means include direct injection to the site of interest. Systemic delivery means may include parenteral or enteral means and encompass all non-local delivery means. Systemic delivery means may include direct injection, such as intravenous injection.

According to another aspect of the invention, there is provided a peptide, nanoparticle or cell delivery system according to the invention for use in therapy, preferably gene therapy.

According to another aspect of the invention, there is provided a method of treating an individual in need of gene therapy comprising the administration of the peptide, nanoparticle or cell delivery system according to the invention, complexed with a nucleic acid or other agent to an individual in need thereof.

According to another aspect of the invention, there is provided a method of improving the bioavailability of a phosphate based drug, comprising the administration of the peptide, nanoparticle or cell delivery system according to any according to the invention complexed with a phosphate based drug, preferably a bisphosphonate drug, to an individual in need thereof.

According to another aspect of the invention, there is provided a method of improving the cellular uptake of gold in an individual comprising the administration of the peptide, nanoparticle or cell delivery system according to any according to the invention complexed with gold to an individual.

According to a another aspect of the invention, there is provided a pharmaceutical composition comprising the peptide, nanoparticle or cell delivery system according to the invention and a pharmaceutically acceptable excipient.

According to another aspect of the invention there is provided freeze-dried or spray-dried nanoparticles. Standard freeze-drying and spray-drying techniques may be used. These nanoparticles are stable after lyophilisation with no reduction in transfection efficacy. They remain as discrete nanoparticles when reconstituted or rehydrated. Advantageously, water or trehalose may be used to reconstitute the freeze-dried or spray-dried nanoparticles.

The present invention will now be described with reference to the following non-limiting figures and examples.

FIG. 1: The nuclear localisation signal (NLS) dependent nuclear import of plasmid DNA is shown schematically. The arginine rich NLS recognises importin (IMP)-$\alpha$ protein. IMP-$\beta$ binds the importin-$\beta$ binding (IBB) domain of IMP-$\alpha$ to form the IMP-$\alpha$/$\beta$ heterodimer. Once docked to the nuclear pore complex through IMP-$\beta$, it binds to specific nucleoporins (Nups) on the cytoplasmic side of the NPC. The translocation of the importin/cargo complex through the NPC involves transient association/disassociation interactions of IMP-$\beta$ with the phe-gly (F-G) repeats of Nups throughout the NPC central channel.

Figure 2:
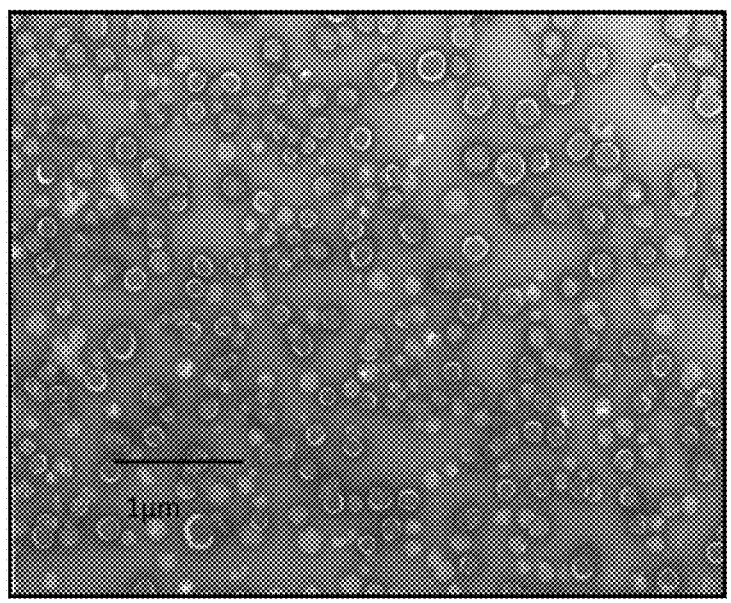

FIG. 2: Transmission electron microscope image highlighting that RALA can also condense siRNA to form spherical nanoparticles formed at N:P 12. Particles were accelerated at a voltage of 80 kV and viewed at a magnification of 40,000×.

Figure 3:
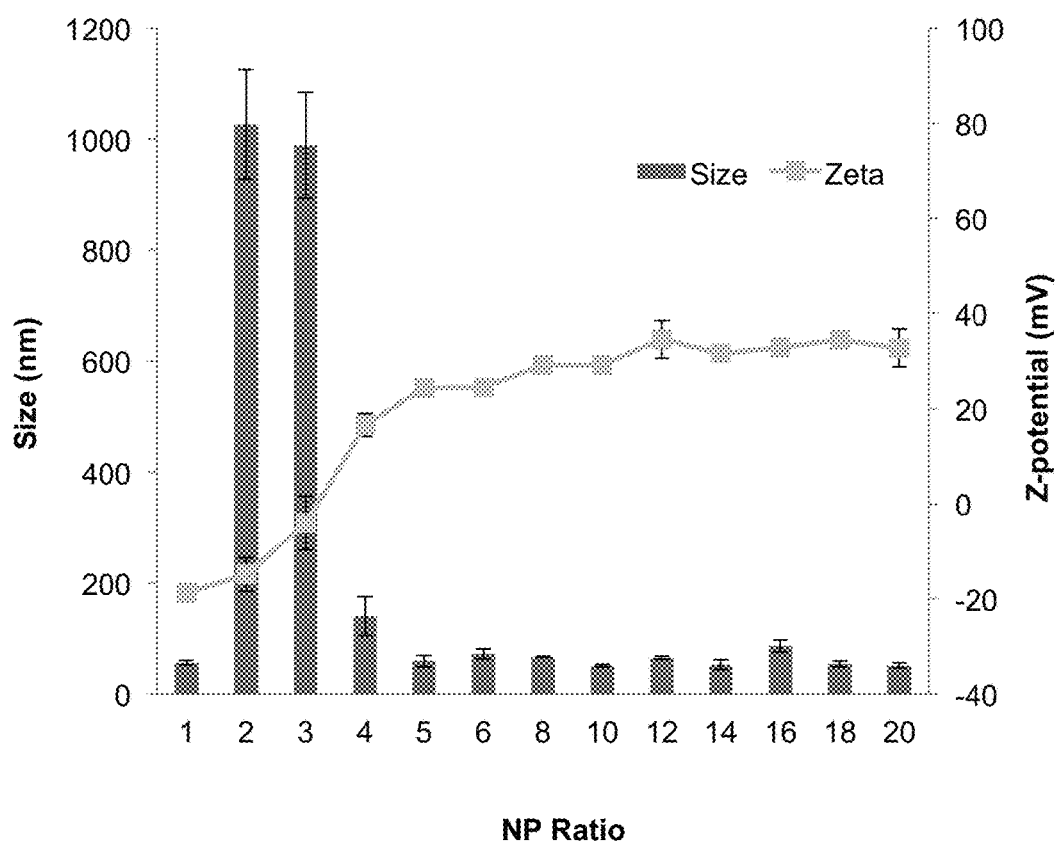

FIG. 3: Nanoparticle size and charge analysis of RALA/GFP with sizes less than 150 nm enabling transport across the cellular membrane. A positive charge of 20-30 mV indicates that the nanoparticles are stable. N:P ratio indicates the ratio of Peptide RALA (N) to pEGFP DNA (P). Data is the mean of three experiments +/−S.E.

Figure 4:
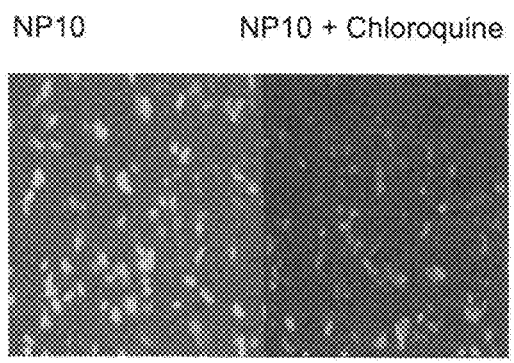

FIG. 4: Evaluation of the transfection efficiency of RALA/GFP nanoparticles in ZR-75-1 (breast cancer) cells transfected N:P ratio of 10. Chloroquine is a known endosomal disruption agent and transfection is not improved upon the addition of this agent indicating effective endosomal disruption with the RALA vector.

Figure 5:
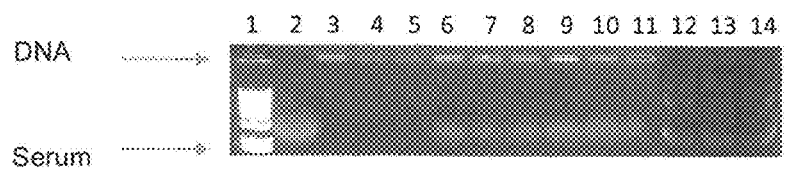

FIG. 5: Incubation of RALA/GFP nanoparticles in 10% serum for 30 mins. Particles remain complexed. 1—ladder, 2—serum only, 3-5 no serum, 6-8 5% serum, 9-11 10% serum, 12-14 Sodium Dodecyl Sulphate. SDS is used to de-complex the nanoparticles. Note that the nanoparticles remain condensed after incubation in 10% serum indicating stability.

Figure 6:
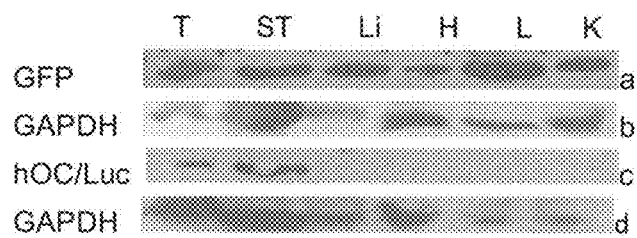

FIG. 6: Western blots showing expression of GFP or luciferase in organs from a SCID mouse bearing a ZR-75 tumour. RALA/GFP or RALA/hOC-Luc nanoparticles N:P ratio of 10 were injected i.v. and 48 hours later the organs were excised and protein extracted. T—tumour, S.T.—surrounding tissue, Li—Liver, H—Heart, Lu—Lungs, K—Kidney. A total of 10 µg of DNA was delivered. Note this is 2.5 times less DNA than previous experiments using lipofectamine delivery injected i.t.

Figure 7A:

FIG. 7A: Incubation of RALA/GFP nanoparticles (N:P 10) in 10% serum and 1% SDS for one hour at 37° C. following freeze drying with the cryoprotectant trehalose. The numbers indicate the ratio of trehalose:DNA. 0 is serum only. The nanoparticles remain condensed after incubation in serum post freeze drying at all trehalose concentrations.

Figure 7B:
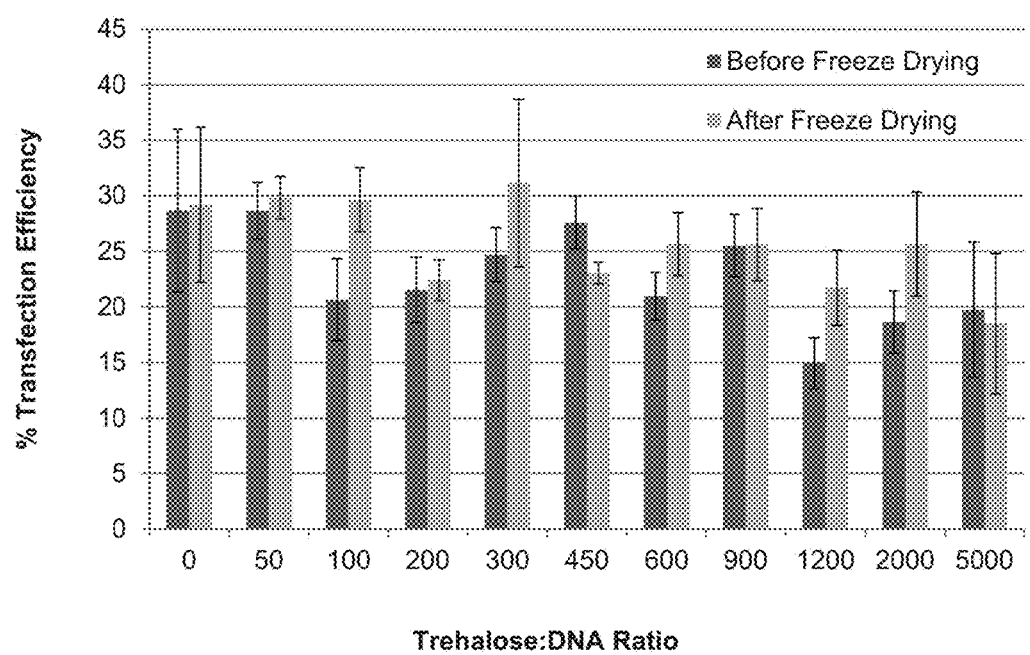
Figure 8A:
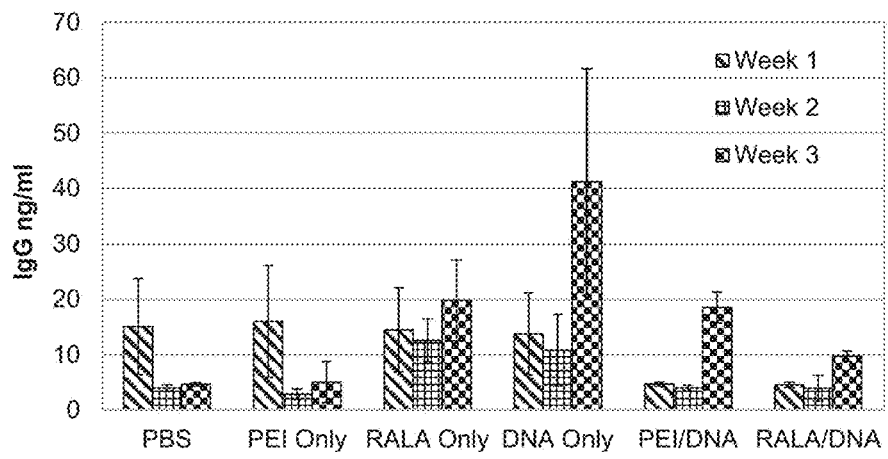
Figure 8B:
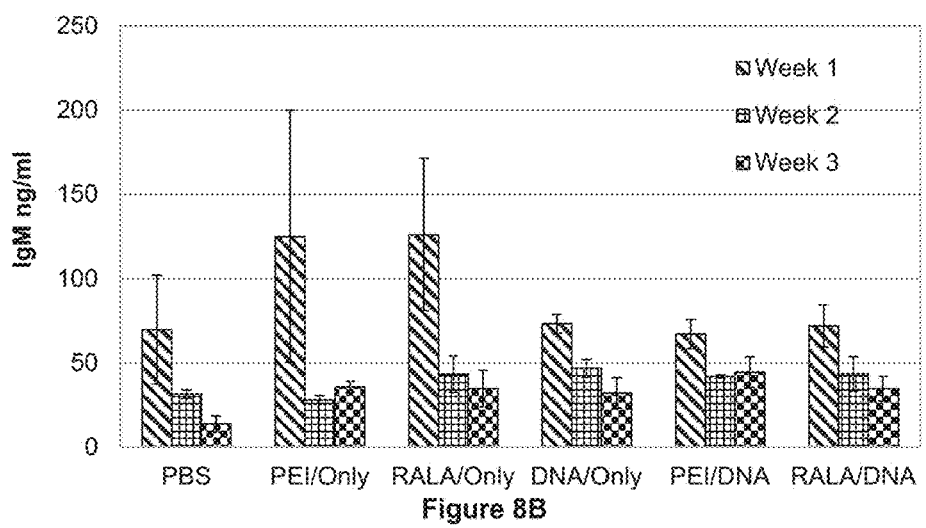
Figure 8C:
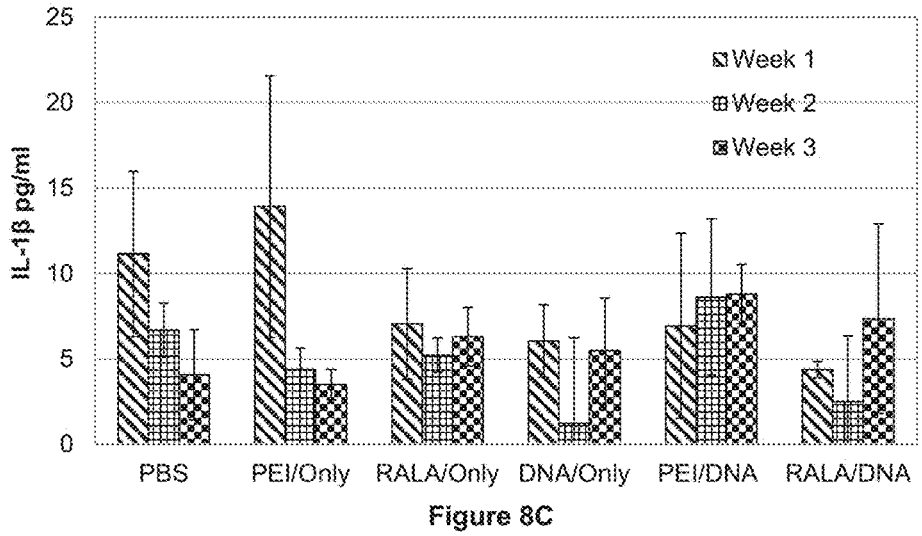
Figure 8D:
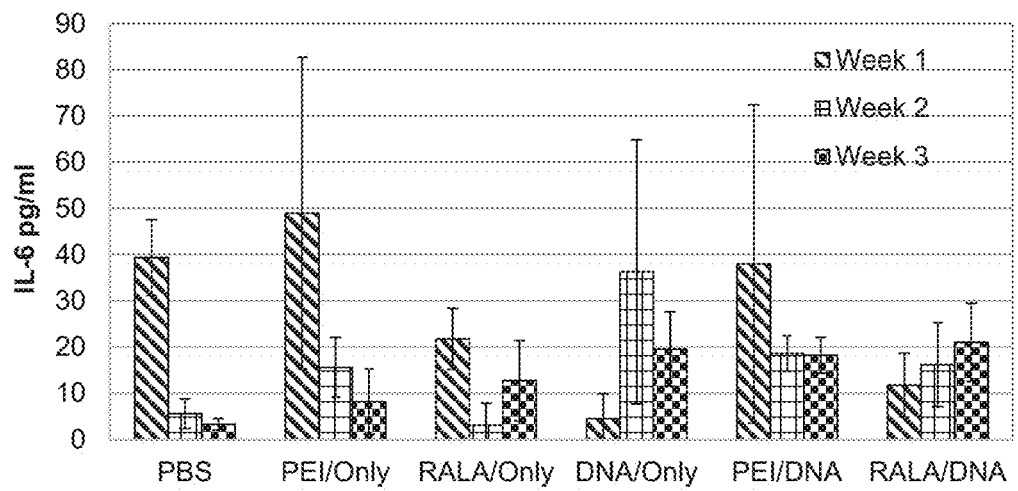
Figure 8E:
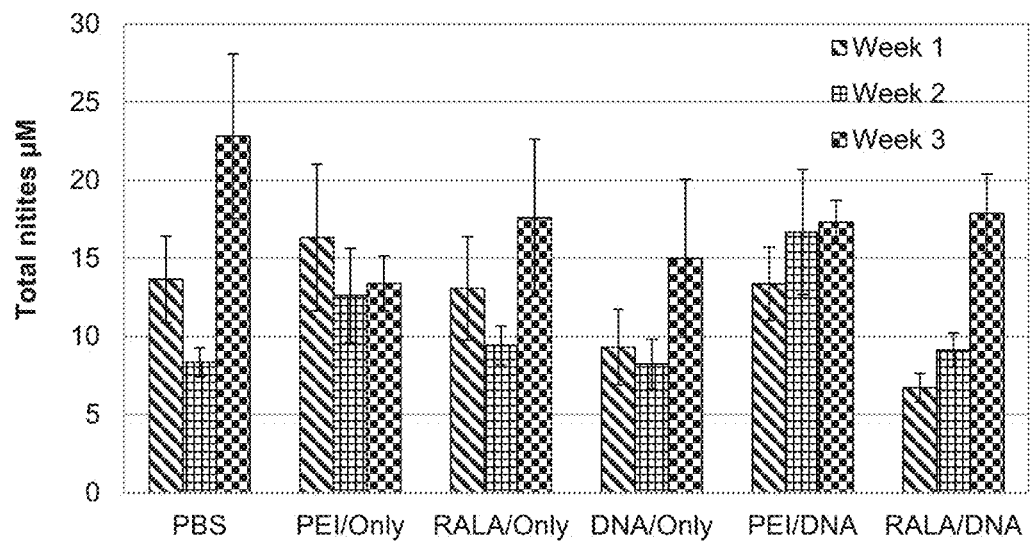

FIG. 7B: Transfection efficiencies of RALA/GFP nanoparticles (N:P 10) before freeze drying (fresh) and after (reconstituted) with trehalose. Transfection efficiency was measured via FACS analysis. Data is the mean of four experiments +/−S.E.

FIG. 8A-E: Immune response of C57BL/6 mice injected with PBS only, PEI only, RALA only, DNA only, PEI/DNA or RALA/DNA nanoparticles. For each injection the equivalent to N:P 10 with 10 µg of DNA was injected. Mice received one injection per week for three weeks. 48 h after each injection three mice were sacrificed and the serum was extracted for analysis. A) IgG, B) IgM, C) IL-1$\beta$, D) IL-6 and E) Greiss test for total nitrites. Each data point is the mean of three independent mice sera +/−S.E. For each of the tests the RALA/DNA nanoparticles do not induce a significant immune response.

Figure 9:
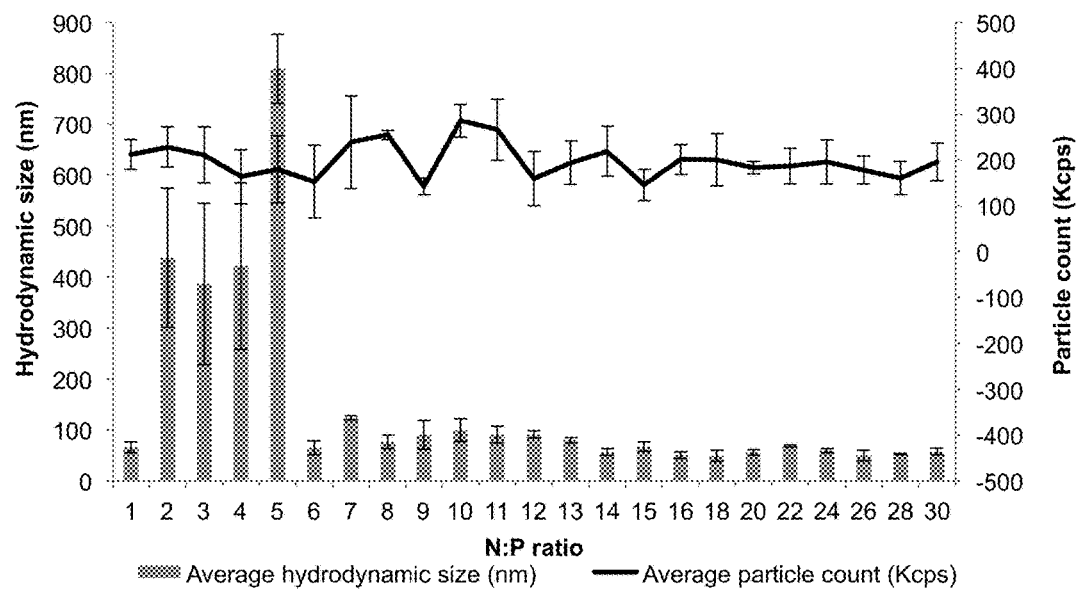

FIG. 9: Characterisation of particles using Malvern Zetasizer. Hydrodynamic size of the RALA/RUNX2 siRNA nanoparticles and their corresponding particle count over a range of N:P ratios. Particle count is fairly consistent and within the ideal range of 100-500 nm. From N:P 6 onwards sizes are consistently less than 150 nm which is within the desired boundary for successful delivery to cells.

Figure 10:
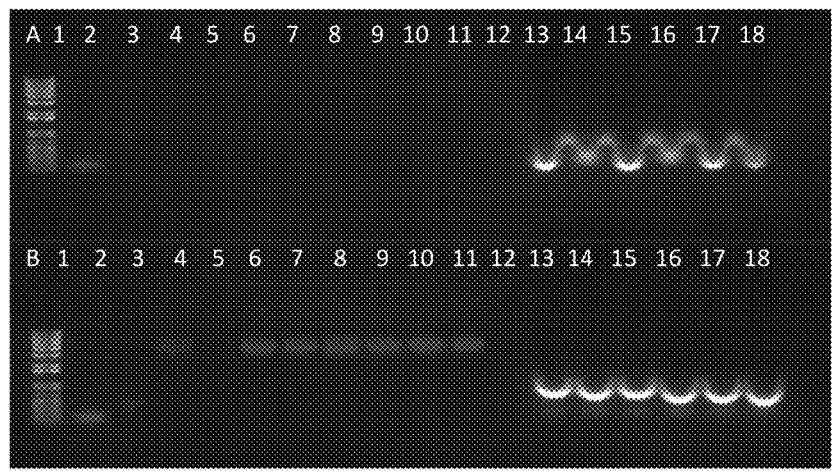
Figure 11A:
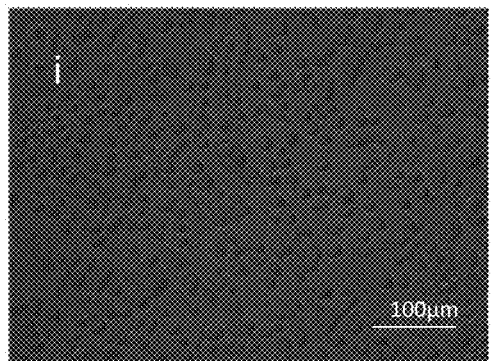
Figure 11B:
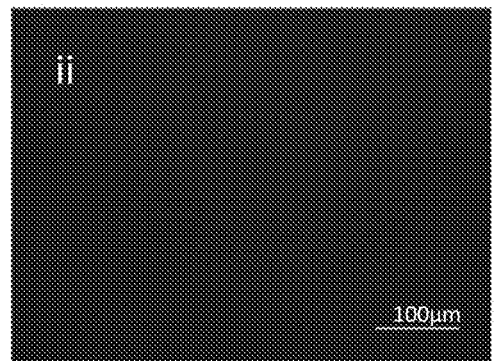
Figure 11C:
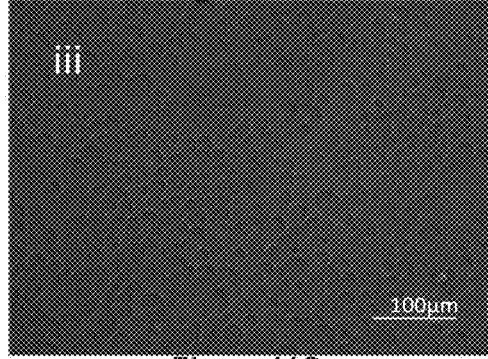
Figure 11D:
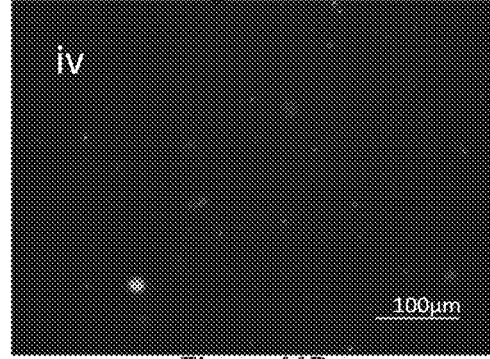
Figure 11E:
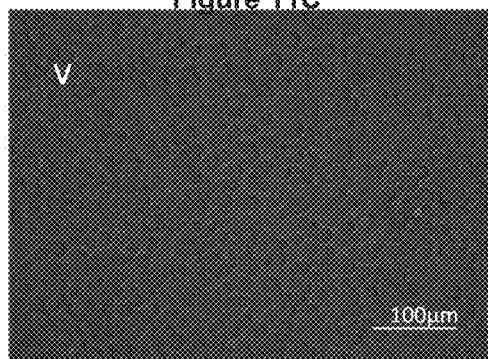
Figure 11F:
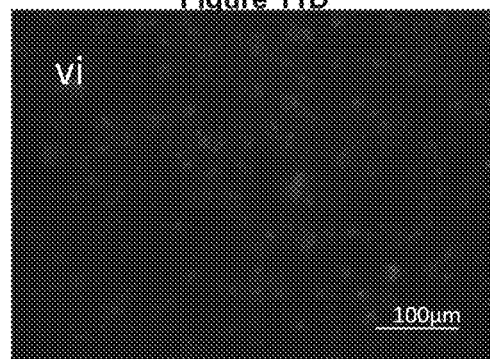
Figure 12A:
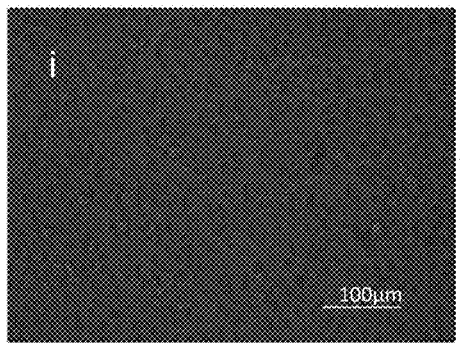
Figure 12B:
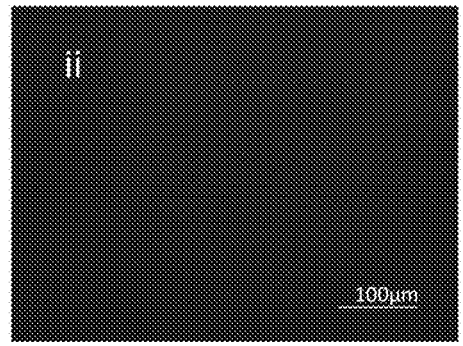
Figure 12C:
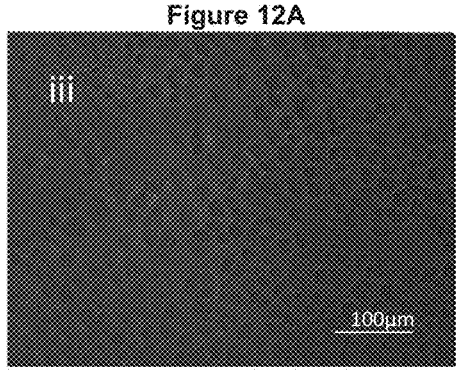
Figure 12D:
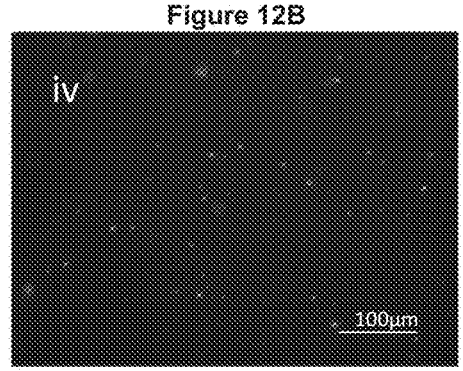
Figure 12E:
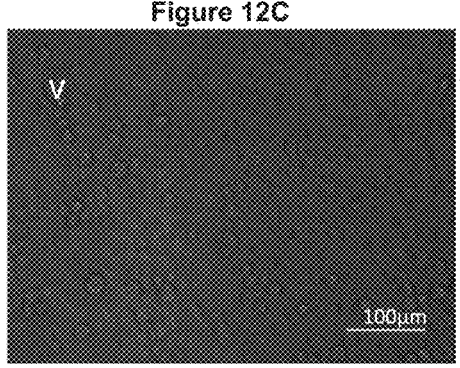
Figure 12F:
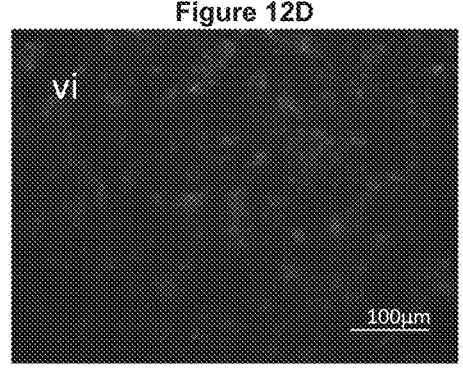

FIG. 10: 1% agarose gel illustrating the stability of the RALA/RUNX2 siRNA nanoparticles at N:P ratio 12+/− serum. Nanoparticles were decomplexed using Sodium Dodecyl Sulphate to confirm integrity of siRNA. A: Lane 1: 1 Kb plus ladder Lane 2: RUNX2 siRNA only Lane 3: SDS only Lanes 6-11: RALA/RUNX2 siRNA nanoparticles incubated at 37° C. for 1-6 hours respectively Lanes 13-18: RALA/RUNX2 siRNA nanoparticles incubated at 37° C. for 1-6 hours respectively and decomplexed with SDS for 10 minutes B: Lane 1: 1 Kb plus ladder Lane 2: RUNX2 siRNA only Lane 3: SDS only Lane 4: Foetal calf serum only Lane 6-11: RALA/RUNX2 siRNA nanoparticles incubated in foetal calf serum at 37° C. for 1-6 hours respectively Lane 13-18: RALA/RUNX2 siRNA nanoparticles incubated in foetal calf serum at 37° C. for 1-6 hours respectively and decomplexed with SDS for 10 minutes.

FIG. 11A-F: PC3 cell line was transfected for 4 hours with RALA/control siRNA nanoparticles N:P 12 containing 0.125 ug siRNA, RALA only equivalent to N:P 12 and oligofectamine/control siRNA complexes and imaged immediately after transfection. (A): Light image of cells transfected with RALA only. (B): Fluorescent image of cells transfected with RALA only. (C): Light image of cells transfected with oligofectamine based complexes. (D): Fluorescent image of cells transfected with oligofectamine based complexes. (E): Light image of cells transfected with RALA based nanoparticles. (F): Fluorescent image of cells transfected with RALA based nanoparticles. Fluorescence was much greater following transfection with RALA/control siRNA compared to the fluorescence seen with oligofectamine/control siRNA under identical conditions.

FIG. 12A-F: MDA-MB-231 cell line was transfected for 4 hours with RALA/control siRNA nanoparticles at N:P 12 containing 0.125 ug siRNA, RALA only, equivalent to N:P 12, and oligofectamine/control siRNA complexes and imaged immediately after transfection. (A): Light image of cells transfected with RALA only. (B): Fluorescent image of cells transfected with RALA only. (C): Light image of cells transfected with oligofectamine based complexes. (D): Fluorescent image of cells transfected with oligofectamine based complexes. (E): Light image of cells transfected with RALA based nanoparticles. (F): Fluorescent image of cells transfected with RALA based nanoparticles. Fluorescence was much greater following transfection with RALA/control siRNA compared to the fluorescence seen with oligofectamine/control siRNA under identical conditions.

Figure 13:
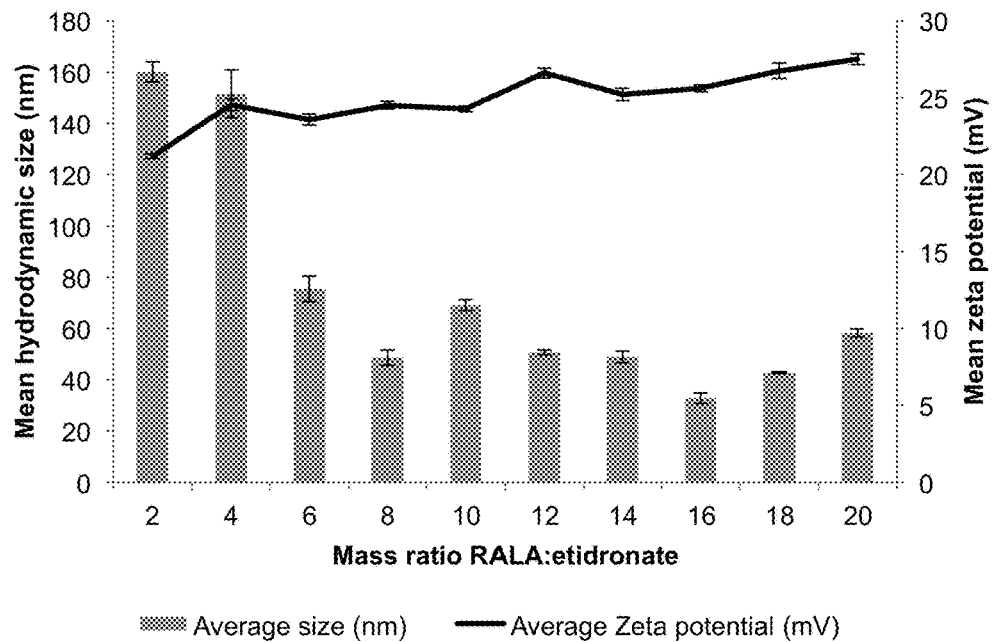

FIG. 13: Characterisation of RALA/etidronate nanoparticles using Malvern Zetasizer Hydrodynamic size of the RALA/etidronate nanoparticles and their corresponding zeta potential over a range of mass ratios. Particles are consistently less than the 150 nm boundary preferred to maximise transfection efficiency with a ratio of 10 producing the optimal hydrodynamic size.

Figure 14:
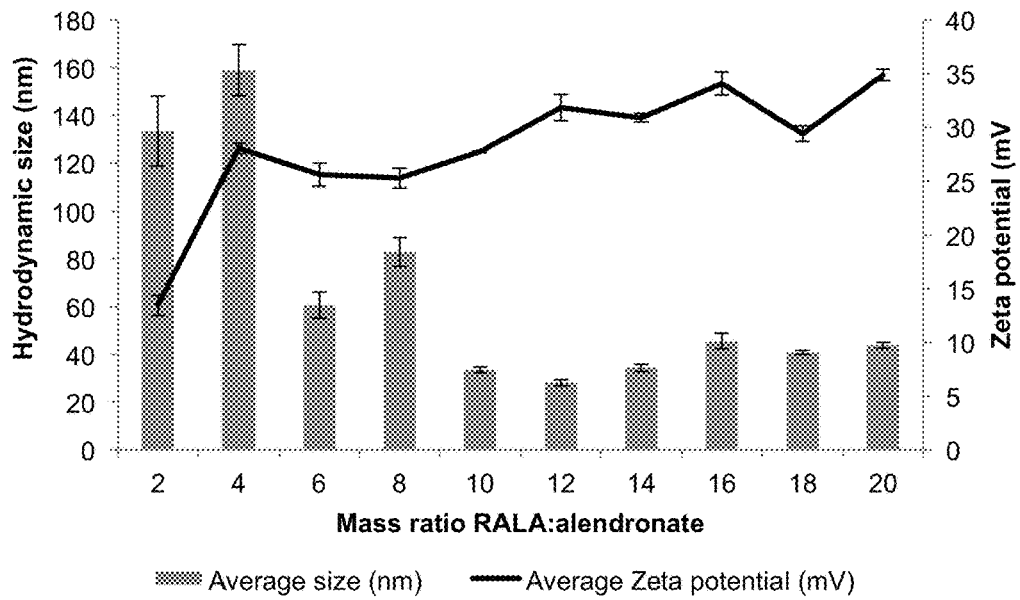

FIG. 14 Nanoparticle size and charge analysis of RALA/Alendronate with sizes less than 150 nm enabling transport across the cellular membrane. A positive charge of 20-30 mV indicates that the nanoparticles are positively charged and will enter cells. Data is the mean of three experiments +/−S.E.

Figure 15:
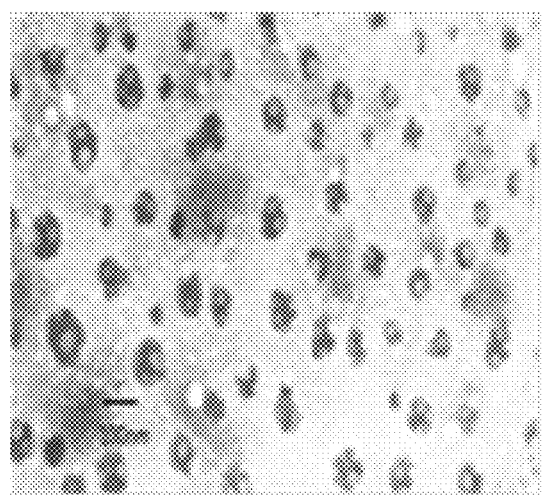

FIG. 15: Transmission electron microscope image highlighting that RALA can condense Alendronate to form spherical nanoparticles at N:P 32. Particles were stained with uranyl acetate at room temperature for 10 mins and accelerated at a voltage of 80 kV. 40,000×.

Figure 16:
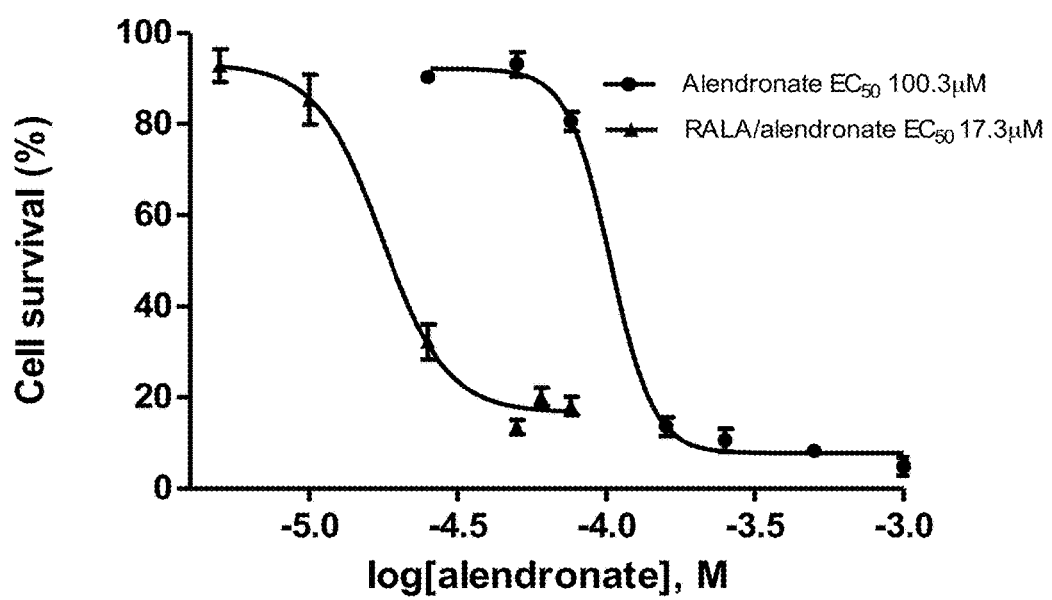
Figure 17A:
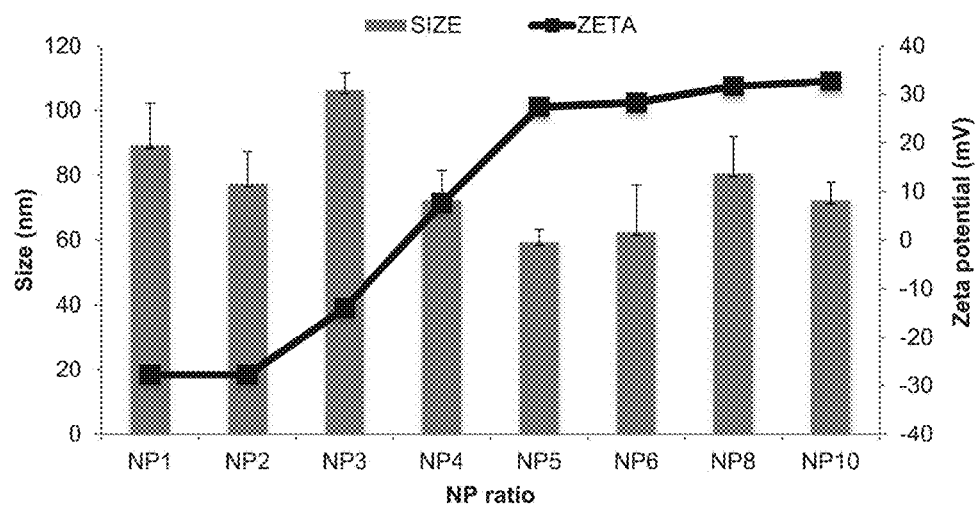
Figure 17B:
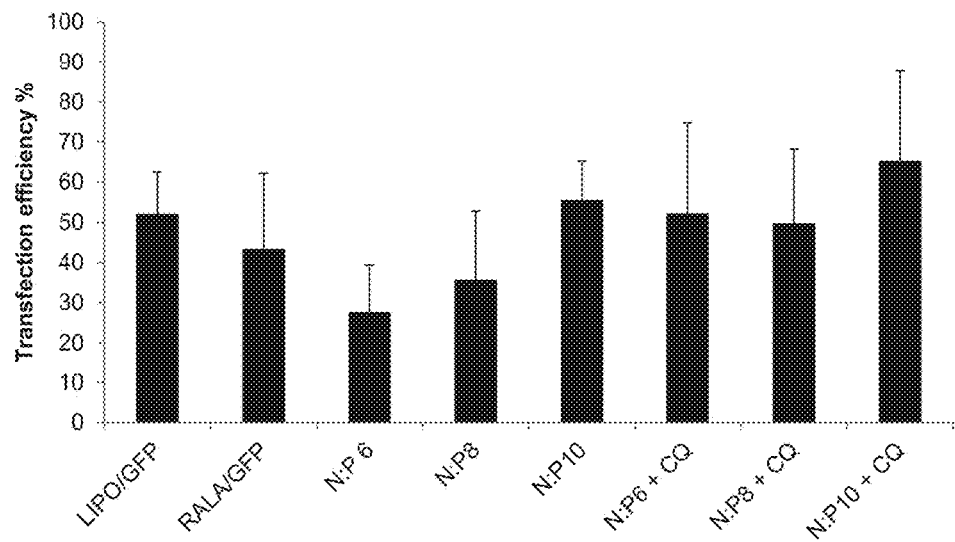
Figure 18A:
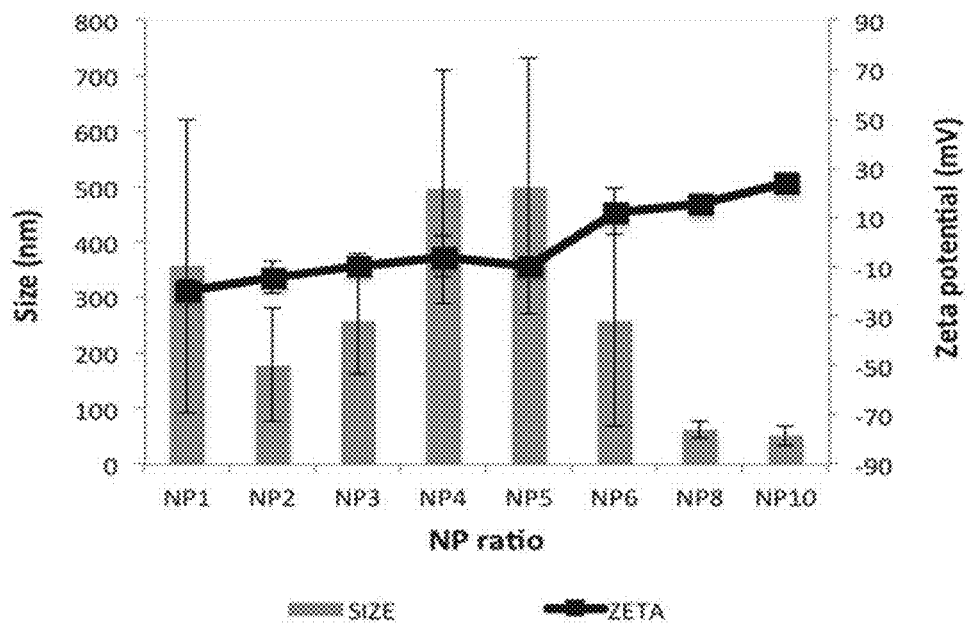
Figure 18B:
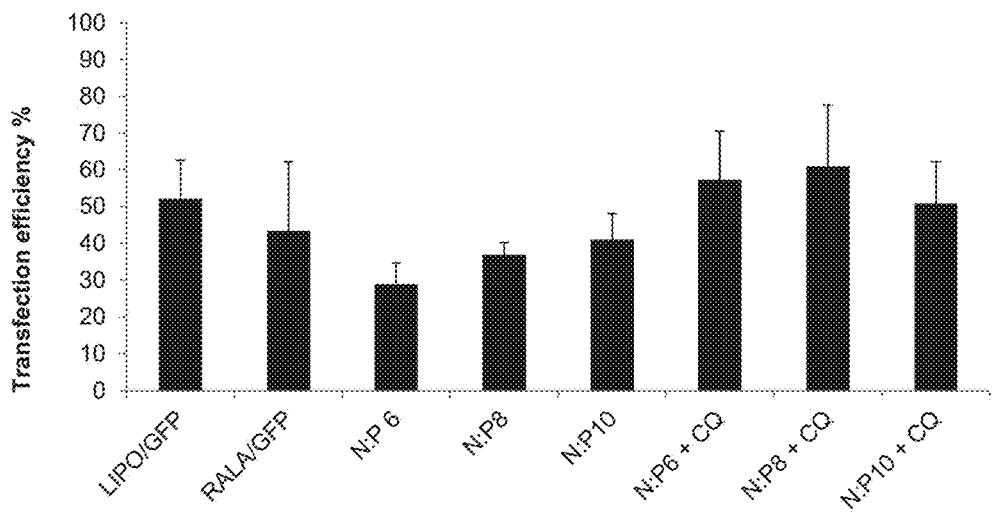
Figure 19A:
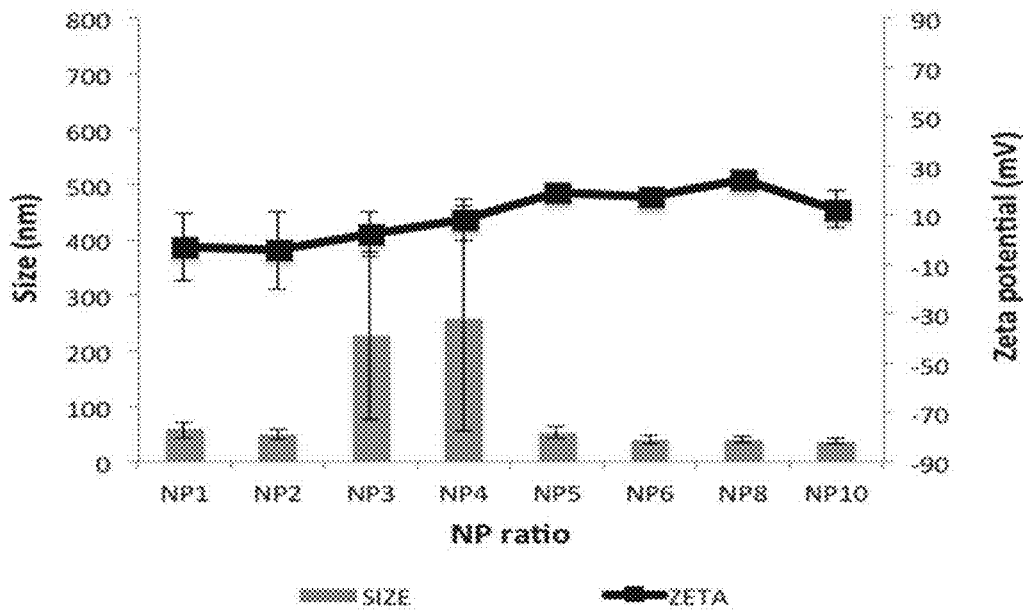
Figure 19B:
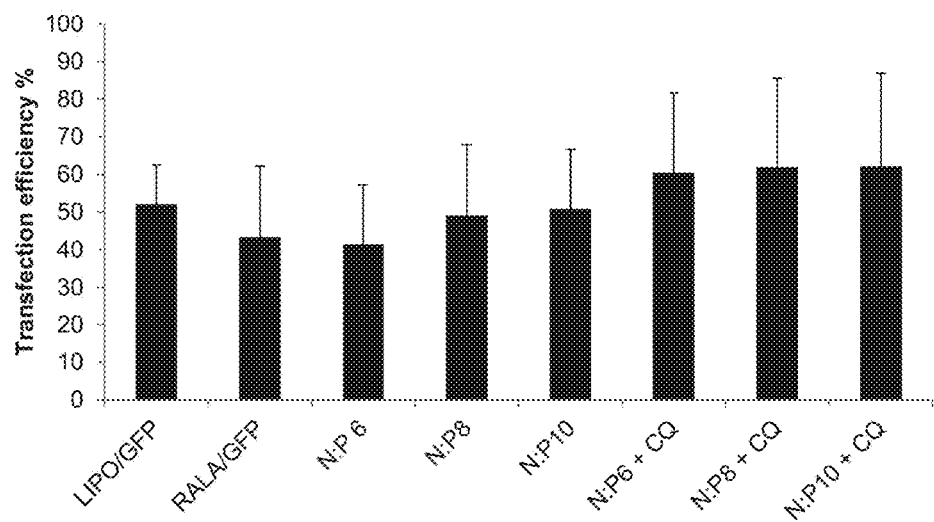
Figure 20A:
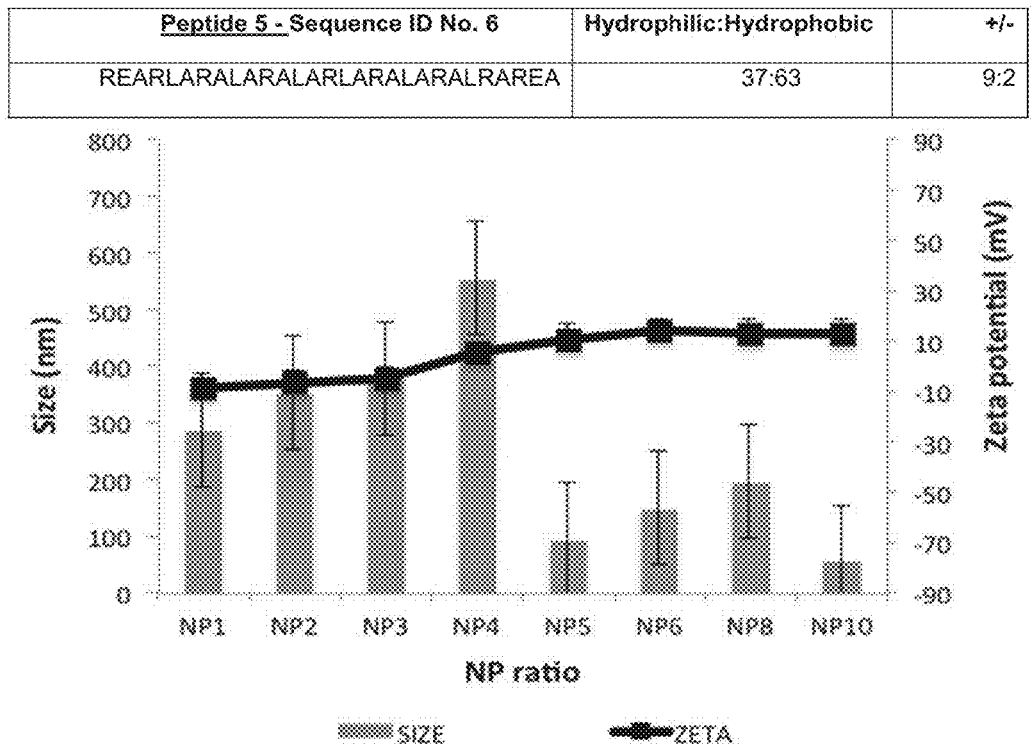
Figure 20B:
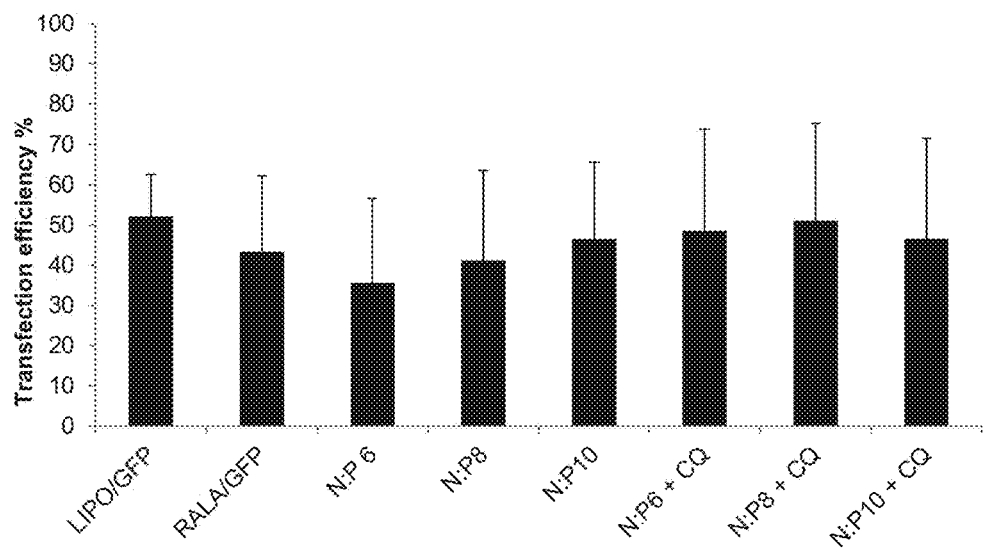
Figure 21A:
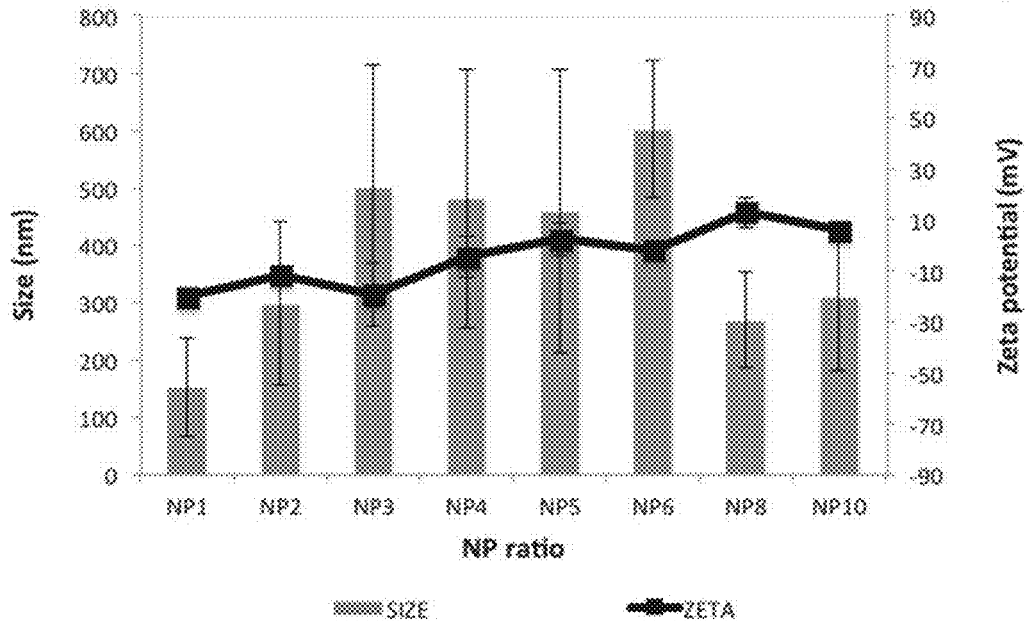
Figure 21B:
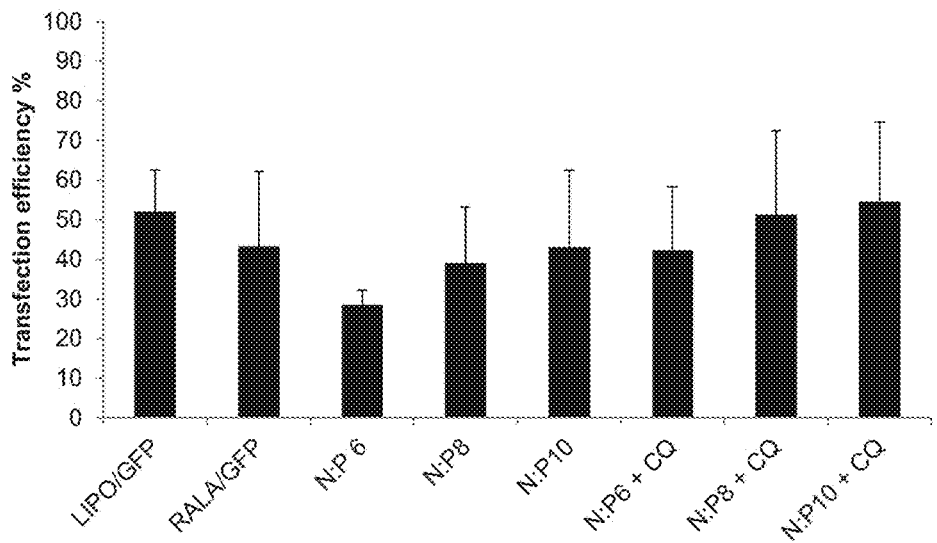
Figure 22A:
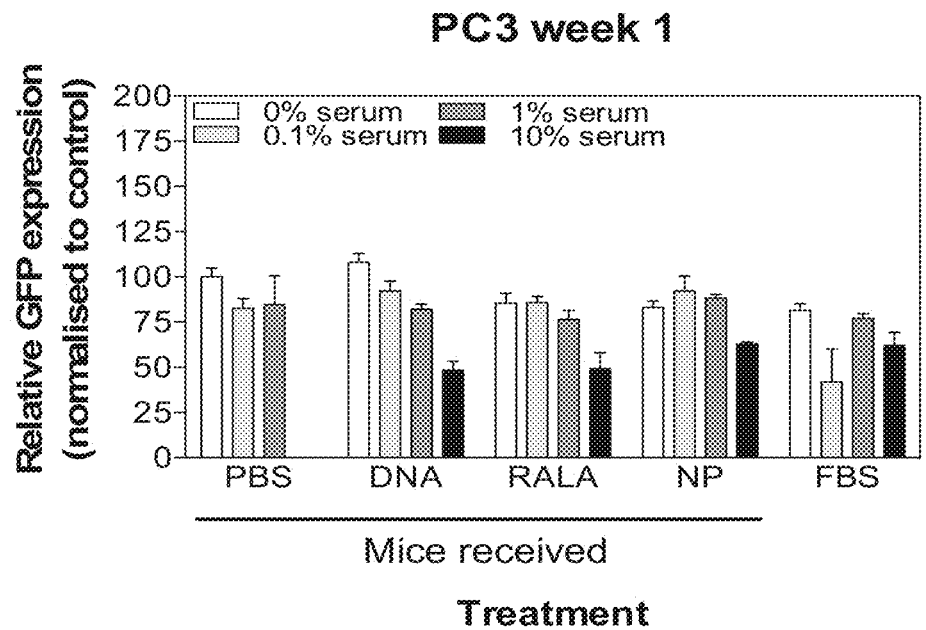
Figure 22B:
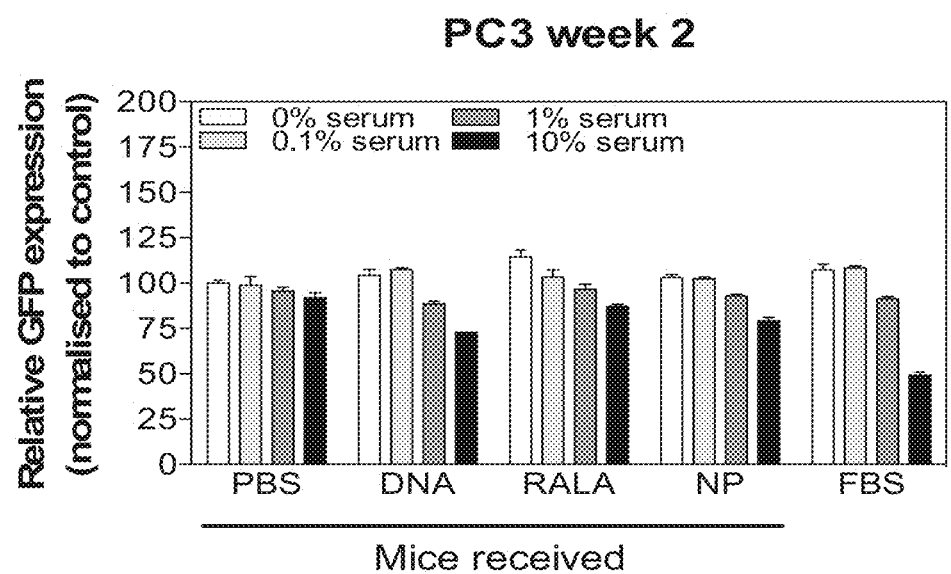
Figure 22C:
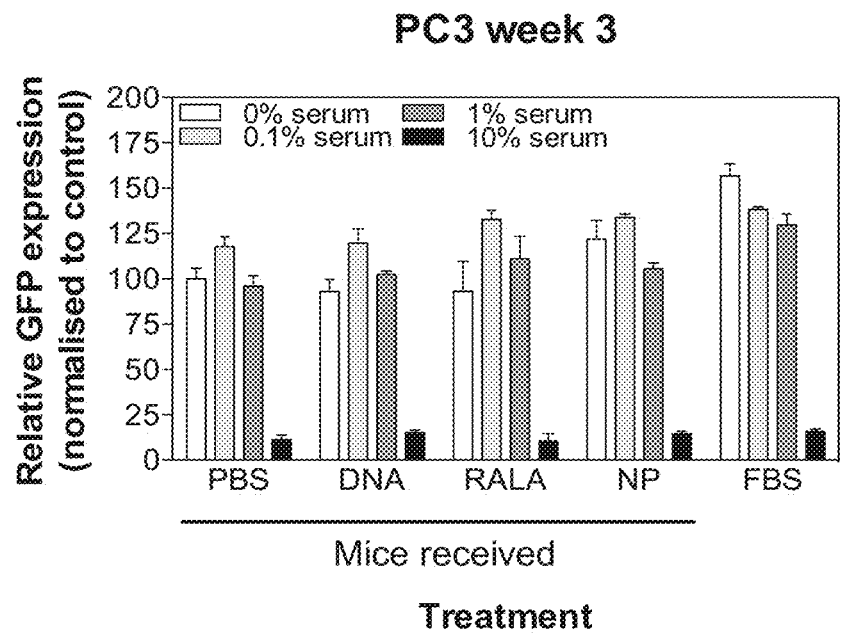
Figure 23A:
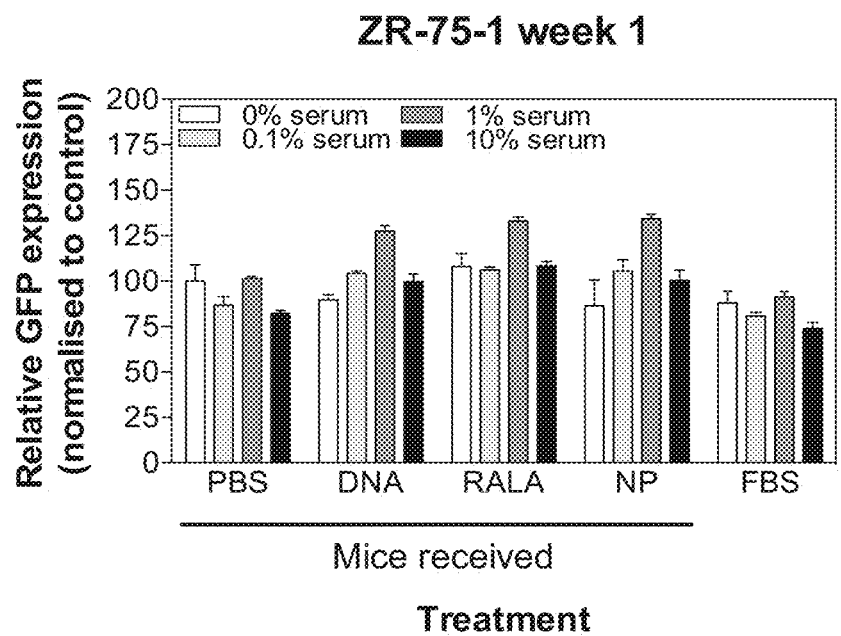
Figure 23B:
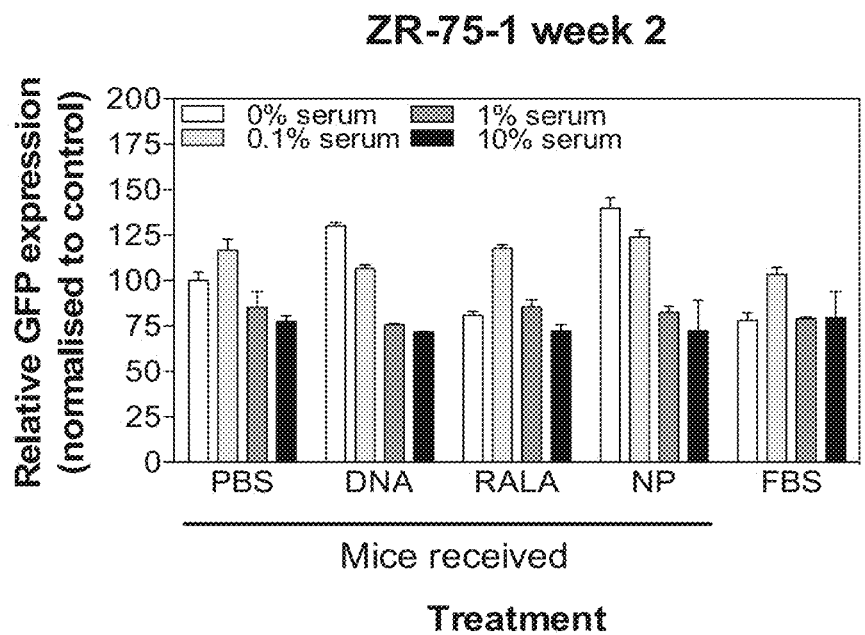
Figure 23C:
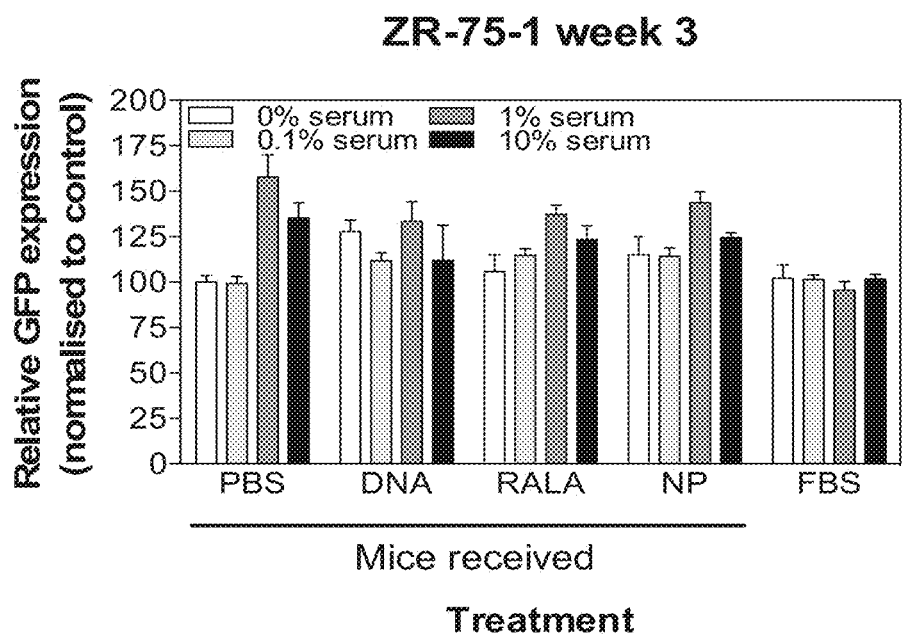

FIG. 16: Dose response curve based on manual cell counts using a haemocytometer. Cells were transfected with RALA/alendronate nanoparticles or treated with alendronate only at a range of concentrations between 10 μM and 250 μM for six hours and allowed to recover for 72 hours before analysis. The untreated control was taken as being 100% cell viability and percentage growth inhibition was determined based on this. The $EC_{50}$ for alendronate only is 97.9 μM and for RALA/alendronate nanoparticles it is 14.3 μM. Data is the mean of three independent experiments +/−S.E.

FIGS. 17A-B, 18A-B, 19A-B, 20A-B, and 21A-B: Nanoparticle size and charge analysis of RALA peptide derivatives with sizes less than 150 nm enabling transport across the cellular membrane. A positive charge of ~10 mV indicates that the nanoparticles are positively charged and will enter cells. Transfection efficiencies of Peptides 2-6 nanoparticles (N:P 8-10) in PC-3 prostate cancer cells. Lipofectamine/GFP and RALA/GFP were controls. Transfections were also performed in the presence of chloroquine to assess endosomal disruption. Transfection efficiency was measured via FACS analysis. Data is the mean of three independent experiments +/−S.E.

FIGS. 22A-C and 23A-C: Vector Neutralisation assay was performed to ensure that RALA/pEGFP nanoparticles are not subject to neutralisation by host immune system in FIG. 22 PC-3 prostate cancer cells from weeks 1 to 2 and FIG. 23 ZR-75-1 breast cancer cells from weeks 1 to 2. C57/BL6 mice received either one/two/three intravenous injection treatments of PBS/DNA/RALA/pEGFP-N1-RALA nanoparticles, were sacrificed, blood isolated, heat-inactivated, incubated with fresh pEGFP-RALA nanoparticles and PC3 and ZR-75-1 cells were transfected. Transfection was normalised to controls and quantified using FACS analysis with 4% gating. Data are the mean of three independent experiments +/−S.E.

Figure 24:
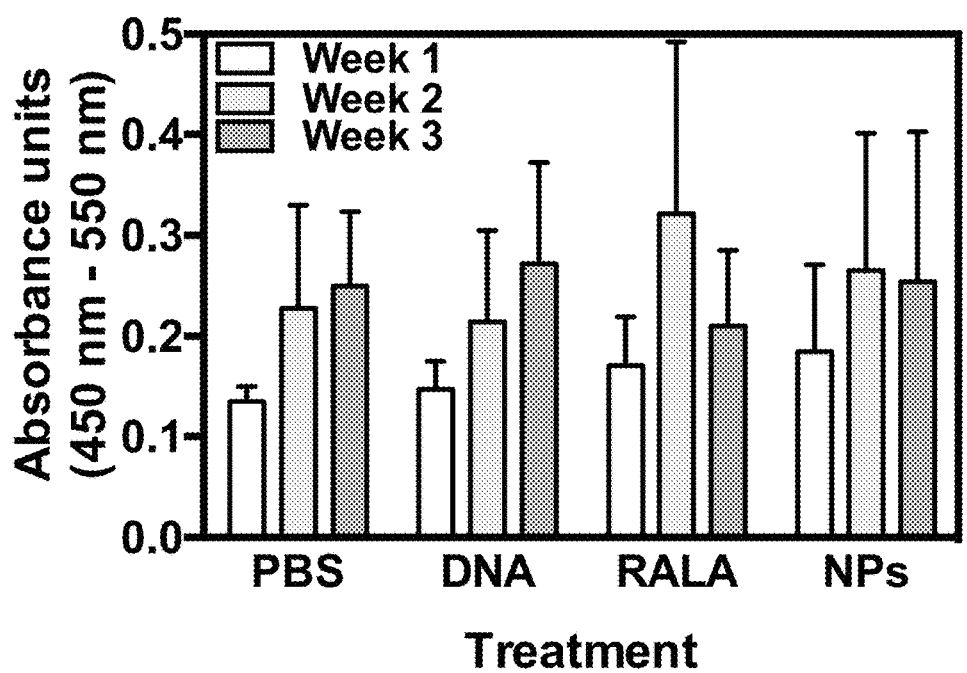

FIG. 24: C57BL6 mice received PBS, 10 μg pEGFP-N1, 14.5 μg RALA, or nanoparticles equivalent to 10 μg pEGFP-N1 complexed at N:P 10 with 14.5 μg RALA. To assess anti-RALA antibody content of mouse serum, the sera used in vector neutralization assays were analysed in ELISA studies. 96 well ELISA plates were coated with pEGFP-N1/RALA nanoparticles as the presentation antigen in PBS overnight at 4° C. Wells were washed with PBS, and non-specific binding to antigen was minimized by blocking with PBS/bovine serum albumin for 1 h at room temperature. The wells were probed with mouse sera (1:100 dilution) for 1 h at room temperature, followed by three washes with ELISA wash buffer. Wells were probed with an anti-mouse secondary antibody conjugated to streptavidin. Following three further washes, the ELISA will be completed by addition of the substrate (TMB), completion of the reaction, and quantification of the colorimetry using an ELISA plate reader. No immunoreactivity was observed compared to the controls. Data are the mean of three independent experiments +/−S.E.

Figure 25:
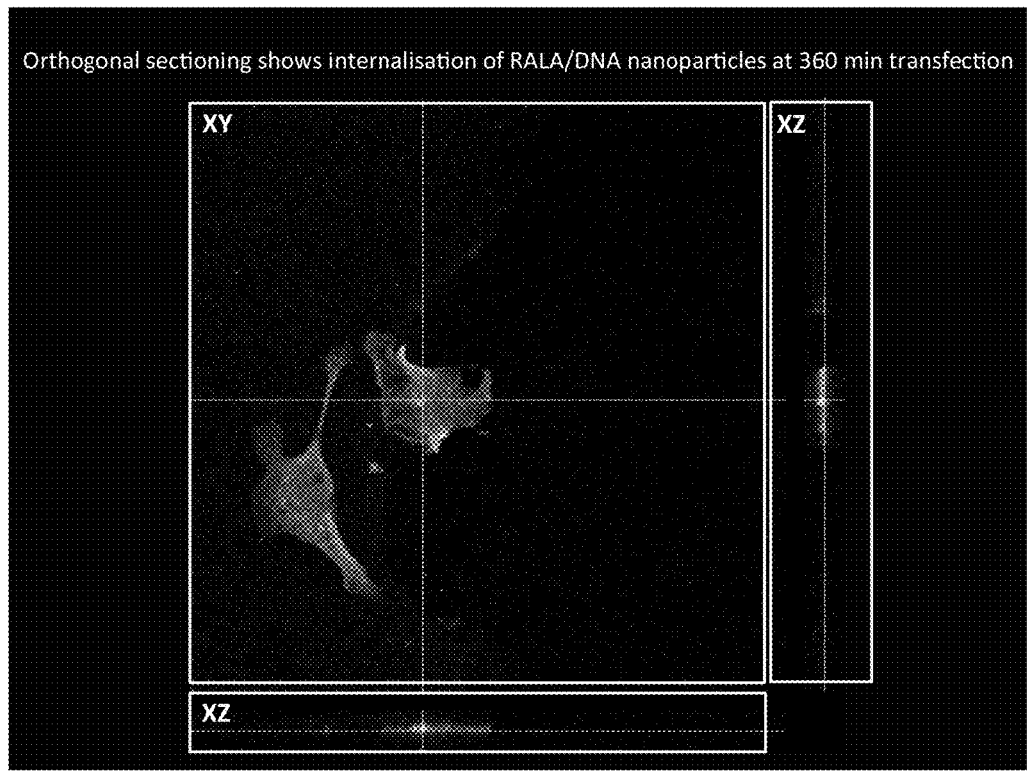

FIG. 25: Representative confocal image of Intranuclear Cy3-DNA/RALA nanoparticles following 360 min transfection in ZR-75-1. Orthogonal sectioning of Z slice at 5.2 μm. In the image, the nucleus appears blue, and Cy3-DNA/RALA nanoparticles appear red. The positioning of the crosshairs was set at a position of interest (in this case an area of intense red staining) in the XY image; the confocal software subsequently generates corresponding XZ and YZ images, allowing for accurate determination of subcellular nanoparticle location.

Figure 26:
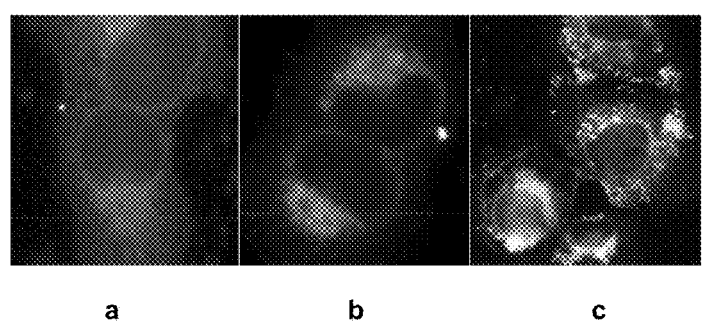

FIG. 26: Cytoviva—Hyperspectral scanned images of MDA-MB-231 cells. A) Untreated control cells. B) 5 nm phosphorylated Gold Nanoparticles. C) 5 nm phosphorylated RALA wrapped Gold Nanoparticles.

Figure 27:
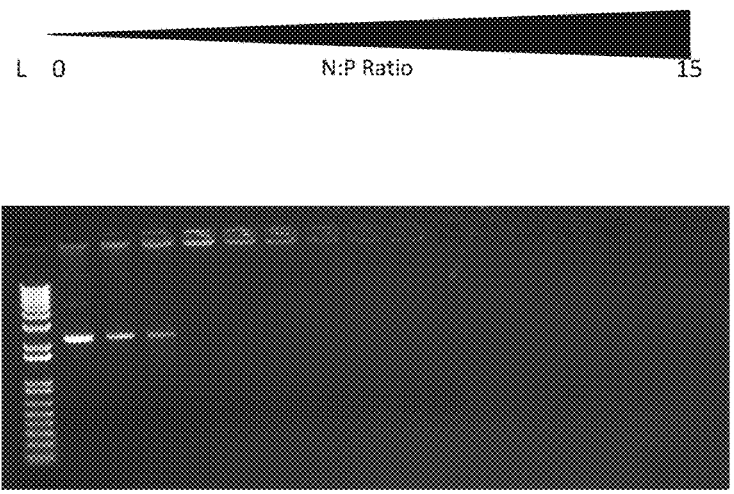

FIG. 27: Gel retardation assay of RALA/pORF-mIL4 nanoparticles over a range of N:P ratios (0-15). RALA/pORF-mIL4 complexes were prepared at N:P ratios 0-15 and incubated at room temperature for 30 minutes. Following incubation 30 μL of samples were electrophoresed through a 1% agarose gel containing 0.5 μg/mL ethidium bromide to visualize DNA. A current of 80V was applied for 1 hour and the gel imaged. L=1 Kb Plus DNA Ladder (Invitrogen, UK). Gel images are representative of three independent studies.

Figures 28A, 28B, 28C:
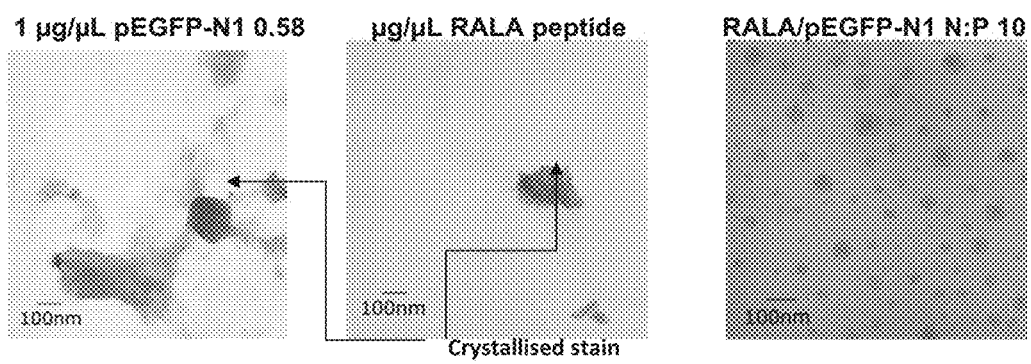

FIG. 28A-C: TEM images of air dried aqueous uranyl acetate (5%) stained Formvar/Carbon mesh grid loaded with (A) 1 μg/μL pEGFP-N1, (B) 0.58 μg/μL RALA peptide and (C) RALA/pEGFP-N1 N:P 10 nanoparticles. Three Formvar/Carbon mesh grids were loaded with 10 μL of each sample and left to dry overnight. The grids were then stained for 5 minutes with 5% aqueous uranyl acetate at room temperature and imaged immediately following staining. The grids were imaged using a JEOL 100CXII transmission electron microscope at an accelerating voltage of 80 kV and magnification 50,000×.

FIG. 29A-B: Characterisation of RALA/pORF-mIL4 nanoparticles N:P 10 via hydrodynamic size analysis following (A) incubation at temperatures 4-37° C. and (B) incubation at room temperature for up to 6 h. Following preparation of RALA/pORF-mIL4 nanoparticles N:P 10 they were characterised over a range of temperatures (4-37° C.) and following incubation at room temperature for up to 6 h using the Malvern Zetasizer NanoZS with DTS software. The measurements are reported as mean±SEM, (n=3).

FIG. 30: Agarose gel analysis of serum stability assay of peptide/pORF-mIL4 nanoparticles at N:P ratio 10 Row 1:Peptide/pORF-mIL4 nanoparticles N:P 10 incubated in water at 37° C. for 1-6 hours and decomplexed with SDS for 10 minutes; Row 2: Peptide/pORF-mIL4 nanoparticles N:P 10 incubated in 10% serum at 37° C. for 1-6 hours and decomplexed with SDS for 10 minutes. Following incubation 30 μL of samples were electrophoresed through a 1% agarose gel containing 0.5 μg/mL ethidium bromide to visualise DNA. A current of 80 V was applied for 1 h and the gel imaged. L=1 kb plus DNA ladder. Gel images are representative of three independent studies.

Figure 31:
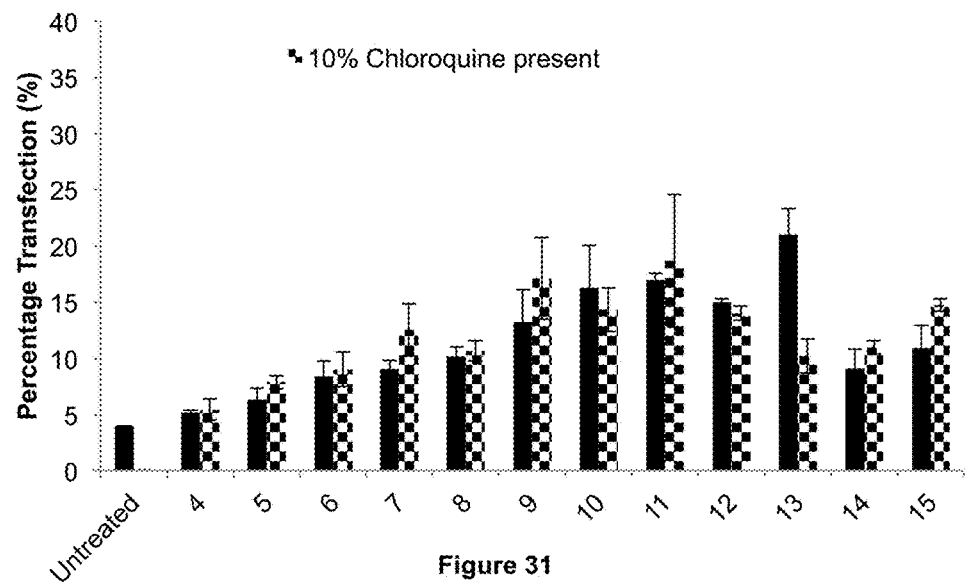

FIG. 31: Flow cytometric analysis of GFP expression 48 h post transfection in ZR-75-1 cell line with peptide/pEGFP-N1 nanoparticles N:P ratios 4-15. ZR-75-1 cells were conditioned for 2 h in 100 μL Opti-MEM serum free media which was then supplemented with 50 μL peptide/DNA complexes N:P ratios 4-15 containing 1 μg pEGFP-N1. Following transfection for 6 h the media was removed and replaced with RPMI 1640 containing 10% FBS. ZR-75-1 cells were imaged by fluorescence microscopy and fixed in formaldehyde for flow cytometry. The experiment was repeated with the addition of 10% chloroquine. Measurements are reported as mean±SEM, (n=3).

Figure 32:
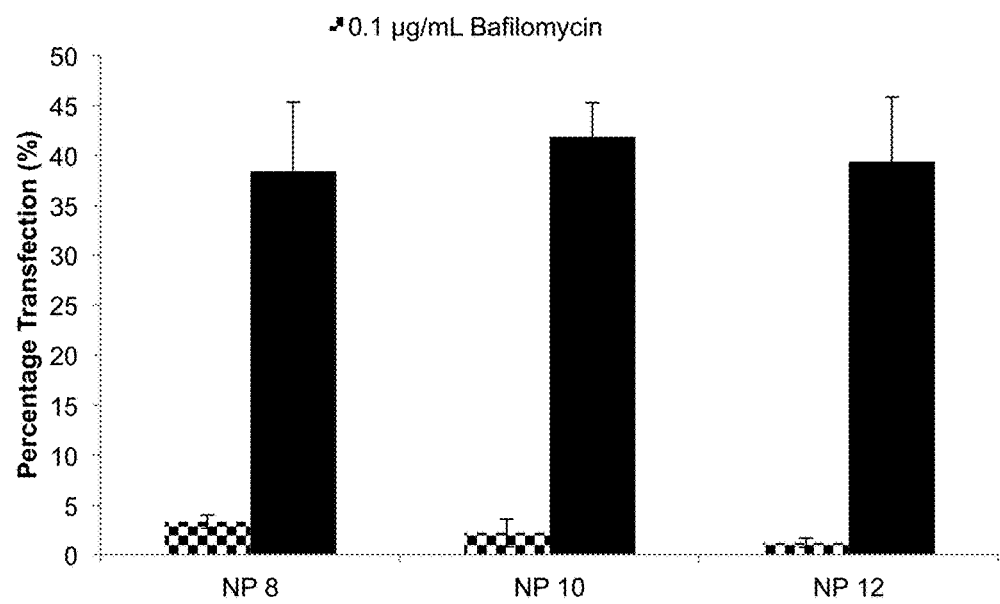

FIG. 32: Flow cytometric analysis of GFP expression 48 h post transfection in ZR-75-1 cell line with RALA/pEGFP-N1 nanoparticles N:P ratios 8, 10 and 12 in the presence and absence of Bafilomycin. ZR-75-1 cells were conditioned for 2 h in 100 μL Opti-MEM serum free media which was then supplemented with 50 μL peptide/DNA complexes N:P ratios 8, 10 and 12 containing 1 μg pEGFP-N1. Following transfection for 6 h the media was removed and replaced with RPMI 1640 containing 10% FBS. ZR-75-1 cells were fixed in formaldehyde for flow cytometry. The experiment was repeated with the addition of 0.1 μg/mL bafilomycin. Measurements are reported as mean±SEM, (n=3)

Figure 33:
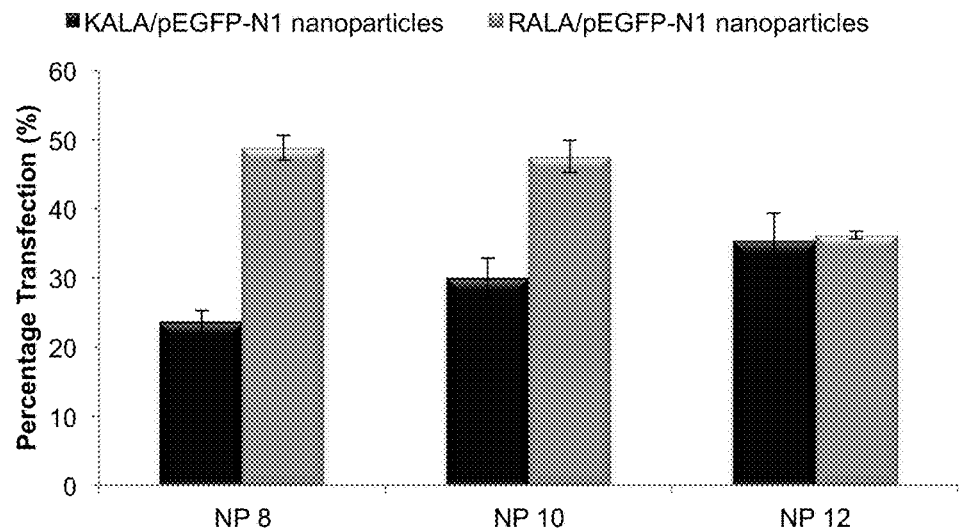

FIG. 33: Flow cytometric analysis of GFP expression 48 hours post transfection in ZR-75-1 cell line with KALA or RALA/DNA nanoparticles at N:P ratios 8, 10 and 12. ZR-75-1 cells were conditioned for 2 hours in 100 μL Opti-mem serum free media which was then supplemented with 50 μL peptide/pEGFP-N1 complexes N:P ratios 8, 10 and 12 containing 1 μg pEGFP-N1. After 6 hours the media was removed and replaced with RPMI 1640 containing 10% FBS. ZR-75-1 cells were fixed in formaldehyde for flow cytometry. The measurements are reported as mean±SEM, (n=3).

Figure 34:
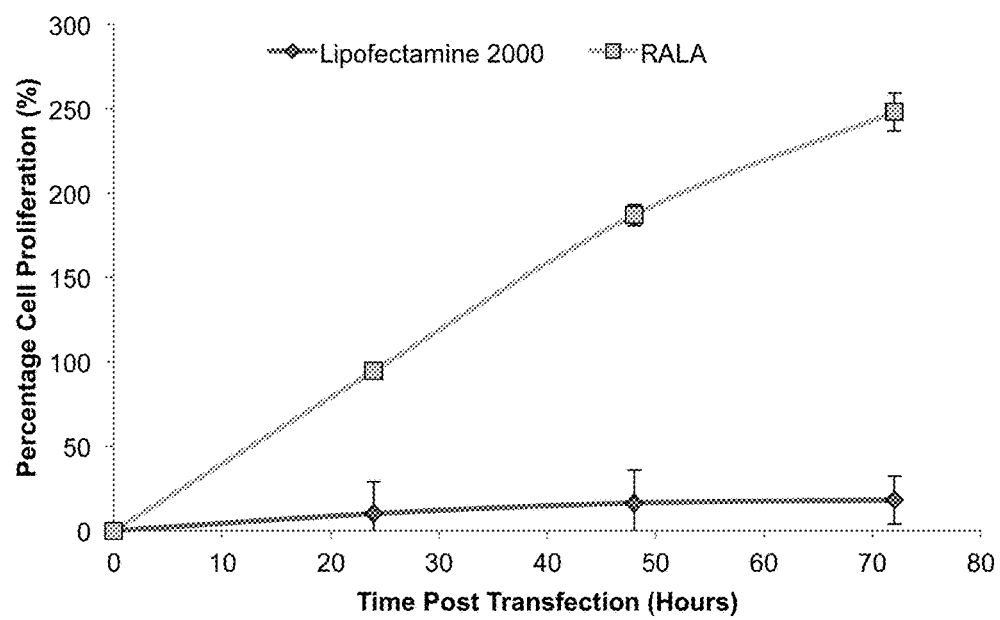

FIG. 34: Cell proliferation over time following transfection with Lipofectamine 2000/pEGFP-N1 and RALA/pEGFP-N1 N:P ratio 10. ZR-75-1 cells were conditioned for 2 hours in 100 μL Opti-mem serum free media which was then supplemented with 50 μL RALA/pEGFP-N1 complexes N:P 10 containing 1 μg pEGFP-N1. After 6 hours the media was removed and replaced with RPMI 1640 containing 10% FBS. Cells were trypsinised and analysed via cell count analysis 24, 48 and 72 hours post transfection. The measurements are reported as mean±SEM, (n=3).

Figure 35:
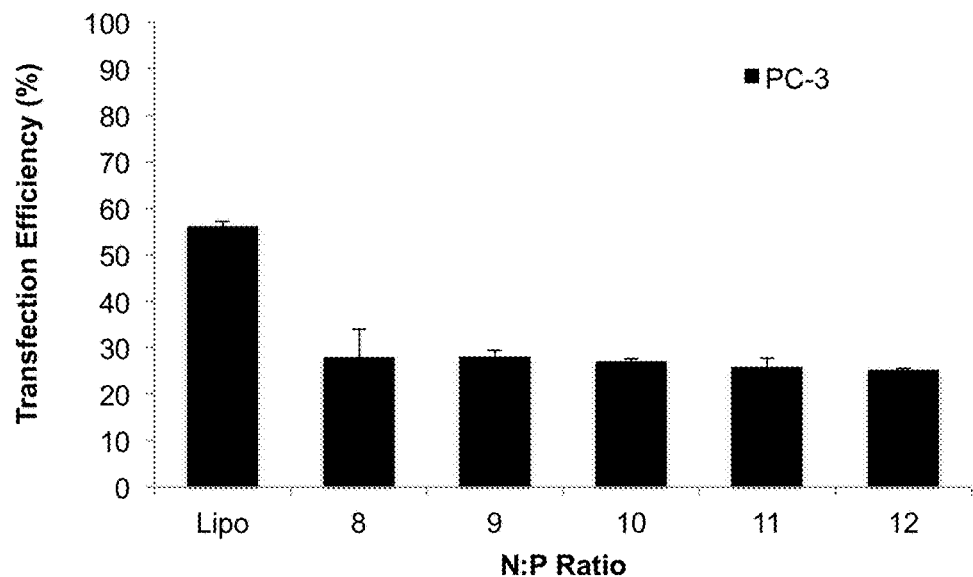

FIG. 35: Flow cytometric analysis of GFP expression 48 hours post transfection in PC-3 prostate cancer with RALA/pEGFP-N1 nanoparticles at N:P ratios 8-12. Cells were conditioned for 2 hours in 100 μL Opti-mem serum free media which was then supplemented with 50 μL RALA/pEGFP-N1 complexes N:P ratios 8-12 containing 1 μg pEGFP-N1. After 6 hours the media was removed and replaced with RPMI 1640 containing 10% FBS. Cells were fixed in formaldehyde for flow cytometry. The measurements are reported as mean±SEM, (n=3).

Figure 36:
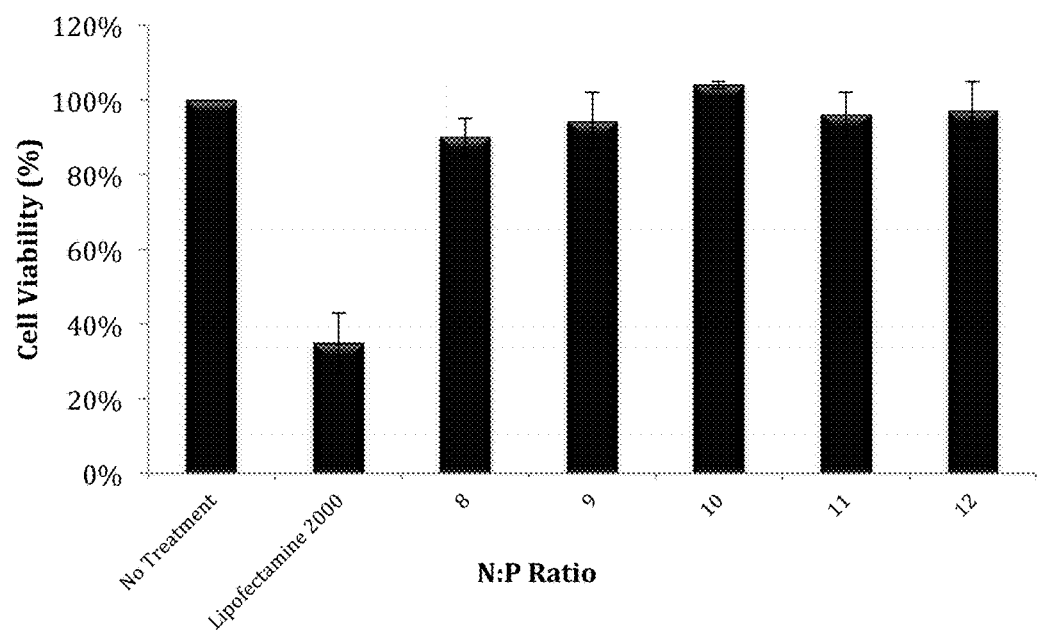

FIG. 36: WST-1 assay to measure cytotoxicity in PC-3 prostate cancer cells 48 hours post-transfection with a range of RALA/pEGFP-N1 N:P ratios. Cells were conditioned for 2 hours in 100 μL Opti-mem serum free media which was then supplemented with 50 μL RALA/pEGFP-N1 complexes N:P ratios 8-12 containing 1 μg pEGFP-N1. After 6 hours the media was removed and replaced with RPMI 1640 containing 10% FBS. The data was normalised against the untreated control which was considered 100% viable. The measurements are reported as mean±SEM, (n=3).

Figure 37A:
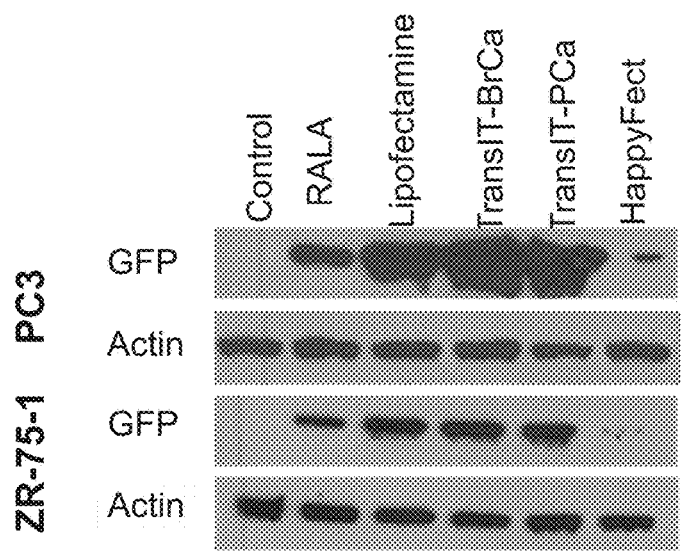
Figure 37B:
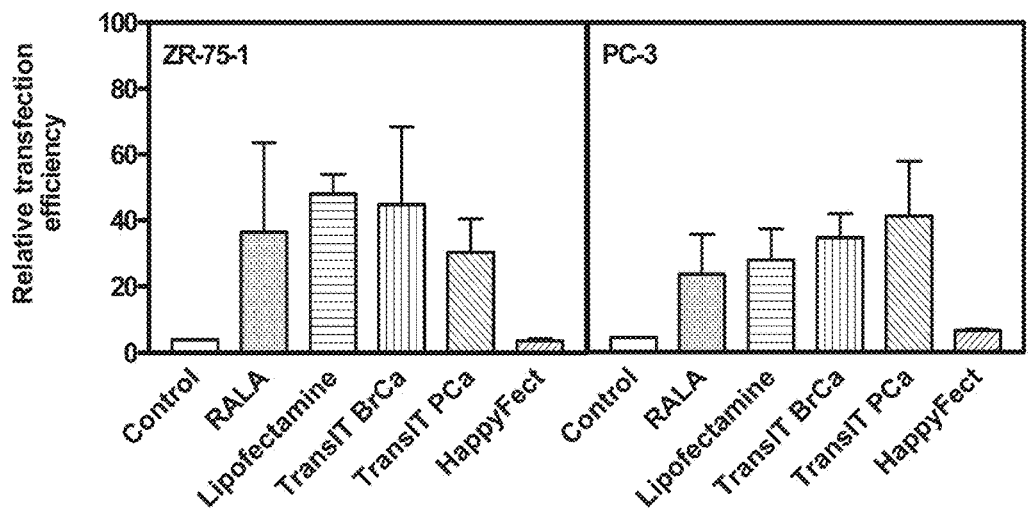

FIG. 37A-B: Assessment of RALA's transfection ability in PC-3 and ZR-75-1 cancer cells in comparison to commercially available transfection reagents. 1.5×105 ZR-75-1 or 1×105PC-3 were seeded into wells of 24 well plates and incubated overnight. Cells were transfected with 0.5 μg pEGFP-N1 per well for 6 h, before transfection complexes were removed and medium replaced with normal growth medium. Cells were analysed for EGFP expression 60 h post-transfection using A) immunoblotting and B) flow cytometry. N=3.

Figure 38:
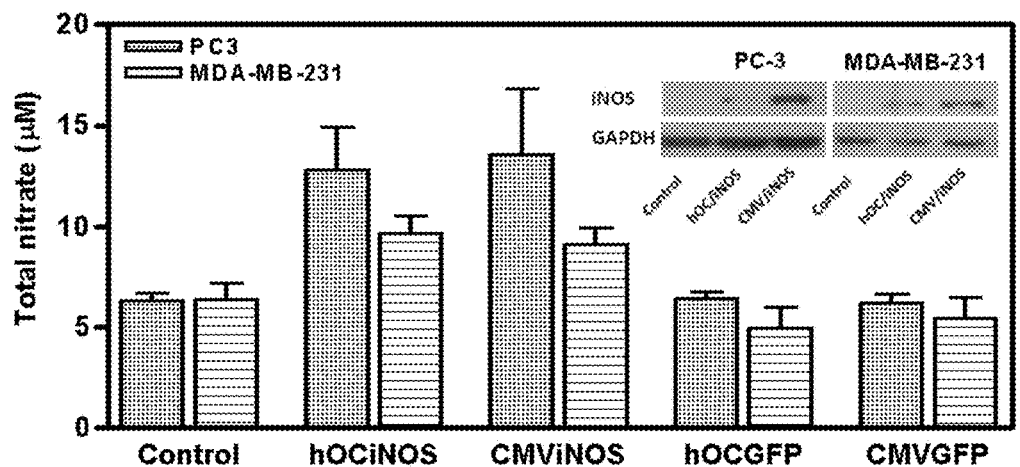

FIG. 38: Validation of CMV and hOC-driven iNOS plasmids. 1.5×105 ZR-75-1 or 1×105PC-3 were seeded into wells of 24 well plates and incubated overnight. Cells were transfected with 0.5 μg CMV-iNOS or hOC-iNOS complexed with RALA per well for 6 h, before transfection complexes were removed and medium replaced with MEM. Cells were analysed for iNOS expression 48 h post-transfection using immunoblotting, and the functionality of the iNOS product was confirmed using Greiss test for nitrate production (B). (N=3+/−SD).

Figure 39:
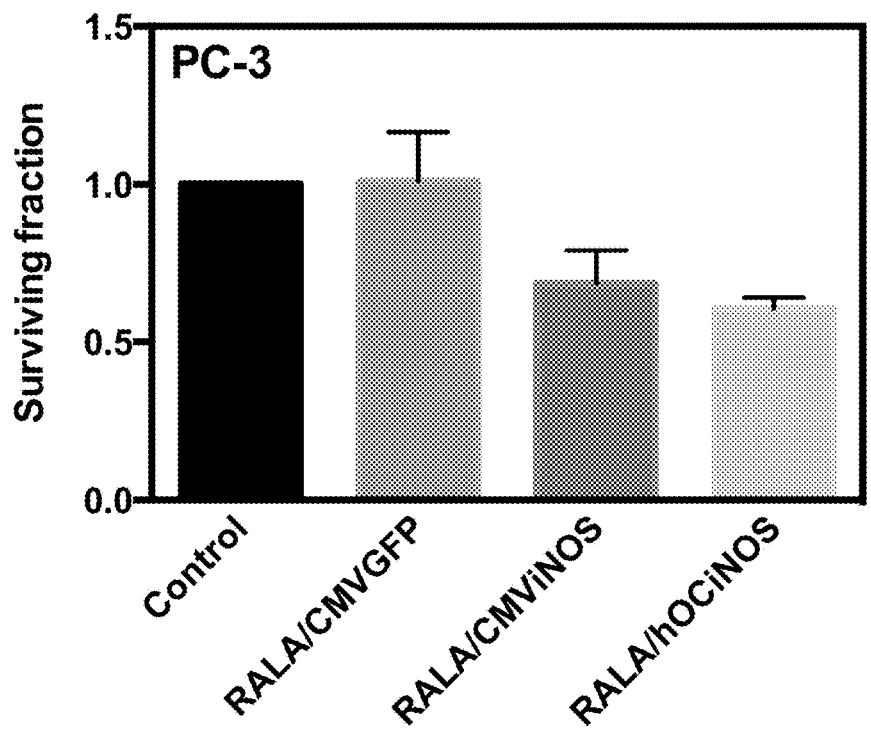

FIG. 39: iNOS gene therapy reduces the clonogenicity of PC-3 prostate cancer cells. Transfection with RALA/CMV-iNOS or RALA/hOC-iNOS nanoparticles reduced the clonogenic survival of PC-3s. 3×105 PC-3s in 6-well plates were transfected with 5 μg DNA complexed with RALA at N:P10. 24 h later, cells were plated into 6 well plates (200/500 per well). Following 10 days incubation, colonies were stained using crystal violet and enumerated. N=2.

Figure 40A:
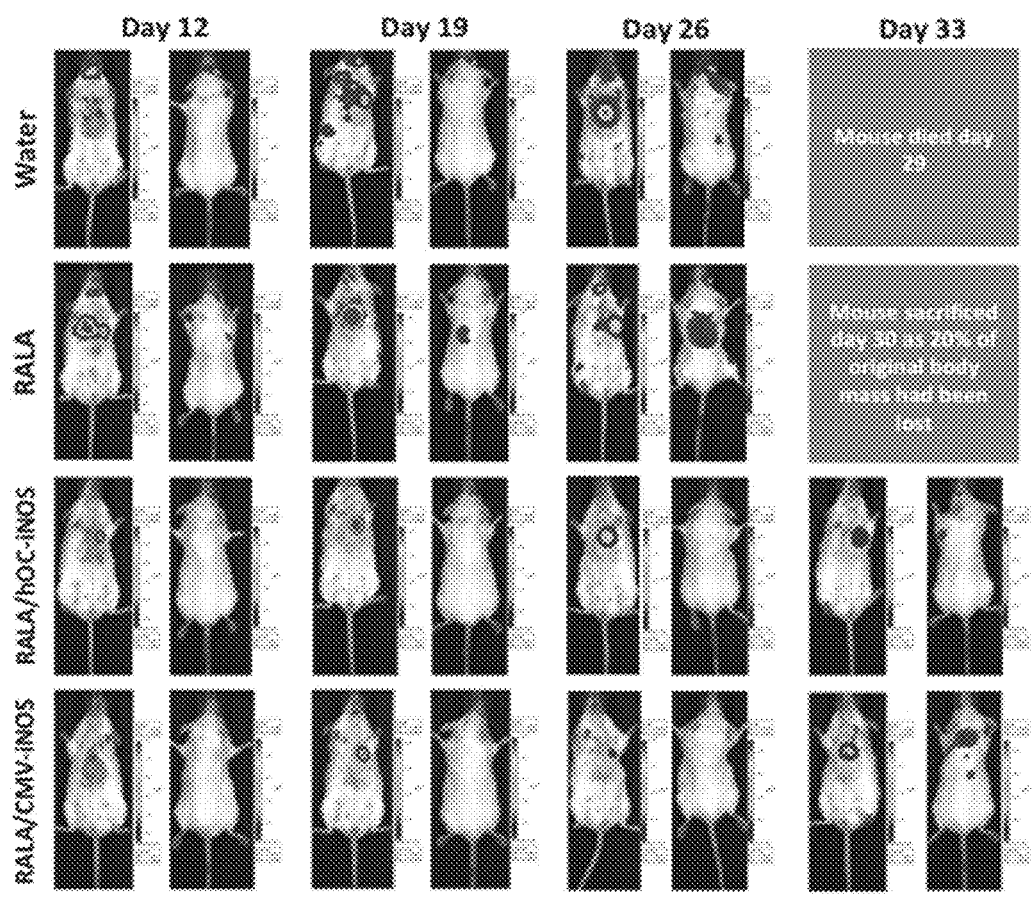
Figure 40B:
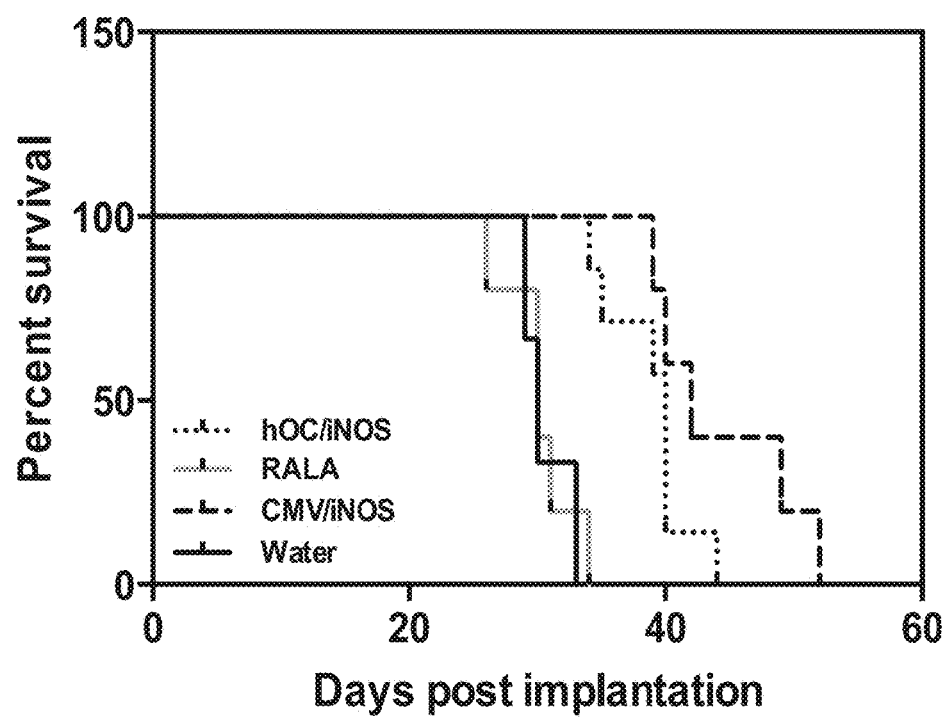

FIG. 40A-B: In vivo efficacy of the RALA/iNOS nanoparticles in a metastatic model of breast cancer. Female BALB/c SCID mice were inoculated via the left ventricle with 2×105 MDA-MB-231-luc2. 48 h later, mice received 10 μg plasmid CMV-iNOS or hOC-iNOS complexed with RALA (7 mice/group), and continued to receive therapy twice weekly for five treatments (Day 16); control mice received water only, or 100 μl of 1.45 mg/ml RALA (corresponding to the amount of RALA in the gene therapy treatments). FIG. 40A) contains bioluminescence images of 4 representative mice at 12, 19, 26 and 33 days post inoculation; at each time point, the degree of bioluminescence in the RALA only, RALA/CMV-iNOS and RALA/hOC-iNOS treated mice was standardised against the degree of bioluminescence in the time-matched water-treated mouse, thereby facilitating comparison of luminescence. In the case of the day 33 mice, for whom no time-matched water-treated control was available, bioluminescence was standardised using the scale parameters of the water-treated mouse as on day 26. FIG. 40B) contains a Kaplan-Meier curve detailing the survival of mice that received the indicated treatment. Mice that received CMV-iNOS or hOC-iNOS gene therapy survived significantly longer than mice that received water treatment (P=0.001 and 0.024 respectively); survival of mice that received RALA therapy without therapeutic DNA payload was not significantly different from that of water-treated mice (P=0.881).

Figure 41A:
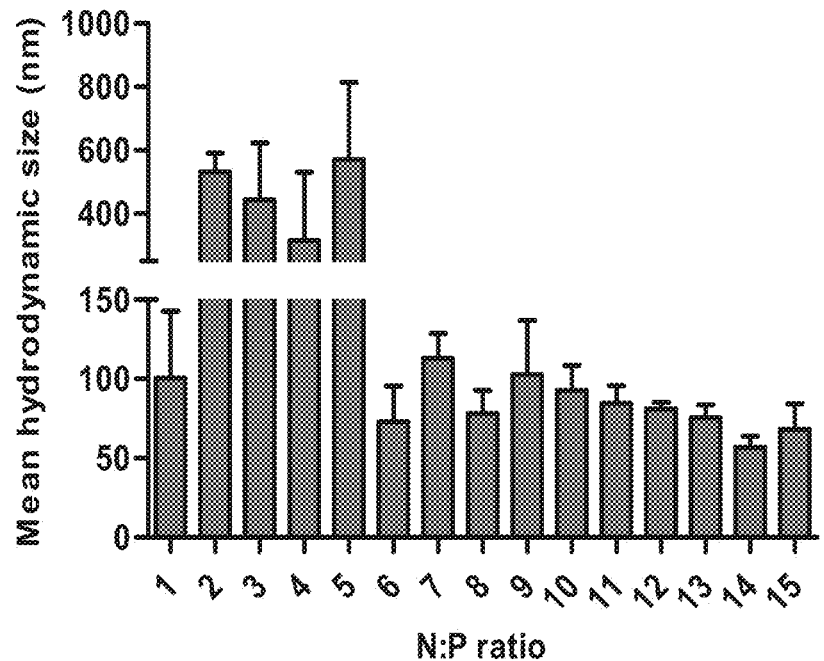
Figure 41B:
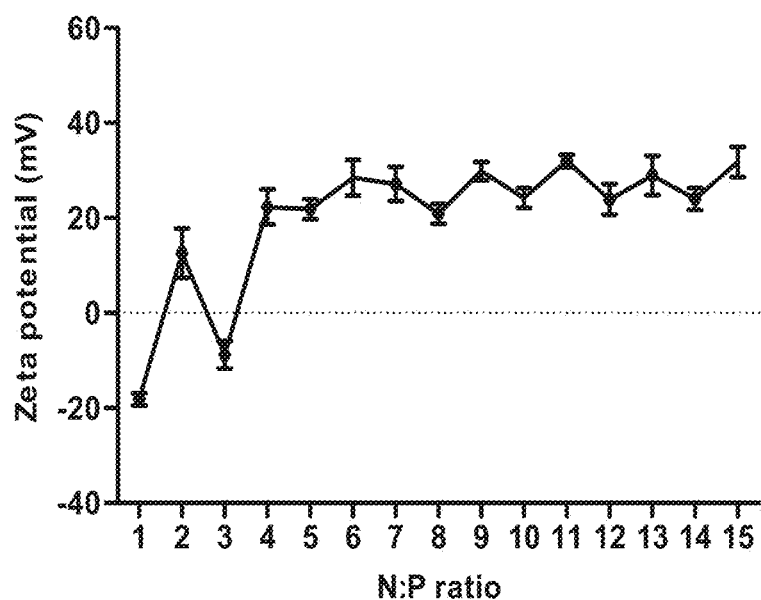

FIG. 41A-B: Mean hydrodynamic size and zeta potential of RALA/Runx2 siRNA nanoparticles prepared at a range of N:P ratios from 1-15. The nanoparticles were incubated for 30 min on ice before their hydrodynamic size (A) and corresponding zeta potential (B) were measured using a Malvern Zetasizer Nano ZS. Results are displayed as mean±SEM, n=3, where n represents the number of independent batches prepared for measurement.

Figure 42A:
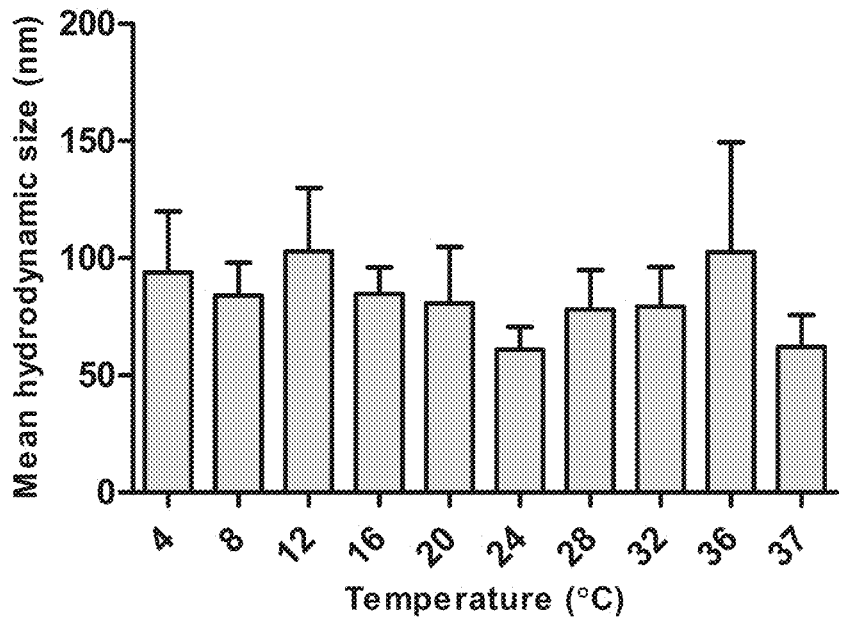
Figure 42B:
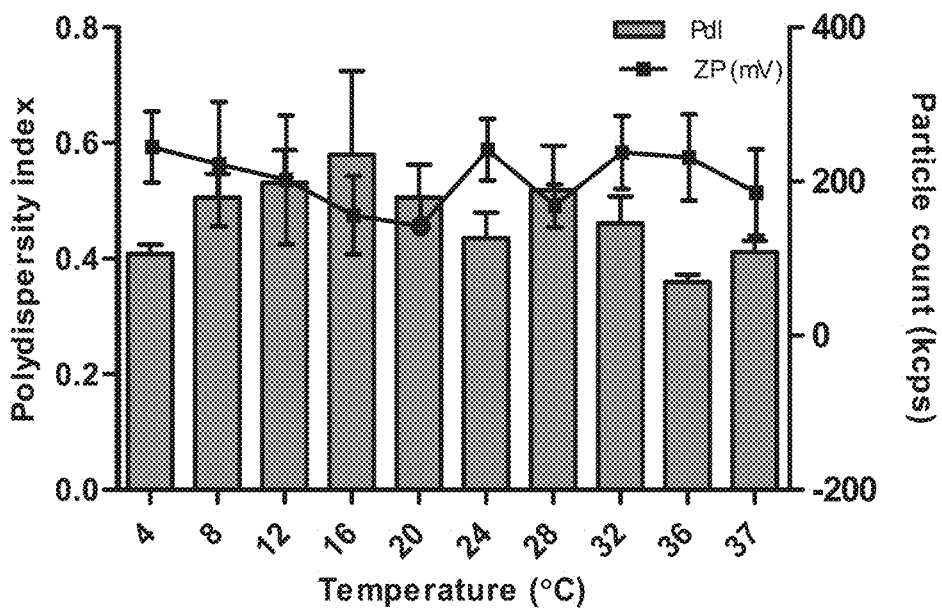

FIG. 42A-B: A: Mean hydrodynamic size of RALA/Runx2 siRNA nanoparticles was determined to assess stability of the particles across a temperature range. RALA/Runx2 siRNA nanoparticles were prepared at N:P 12 such that they contained 0.5 μg Runx2 siRNA and 7.25 μg RALA and incubated on ice for 30 min. The mean hydrodynamic size of the nanoparticles was then measured at 4° C. intervals, from 4° C. to 37° C., using a Malvern Zetasizer Nano ZS. B: The corresponding PDI and particle count were also recorded. Results are displayed as mean±SEM, n=3, where n represents the number of independent batches prepared for measurement.

Figure 43A:
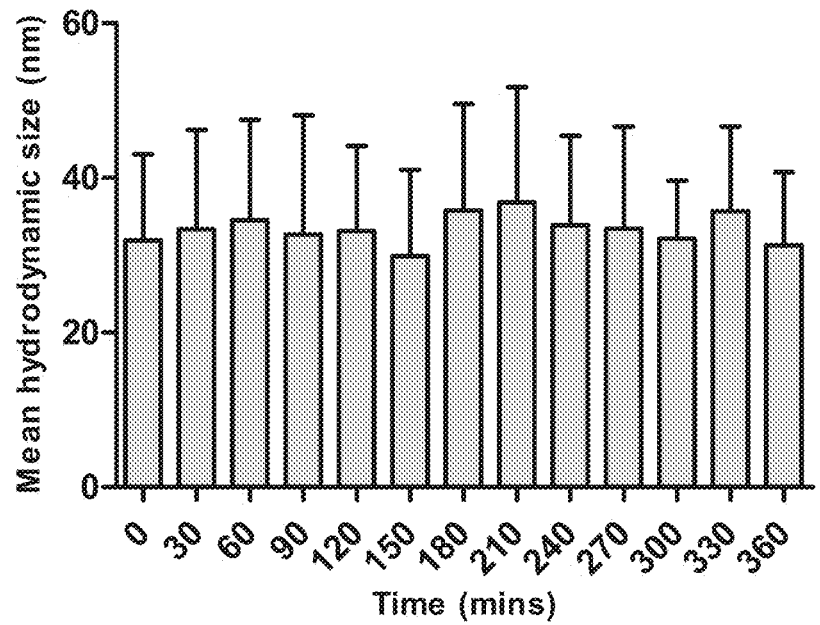
Figure 43B:
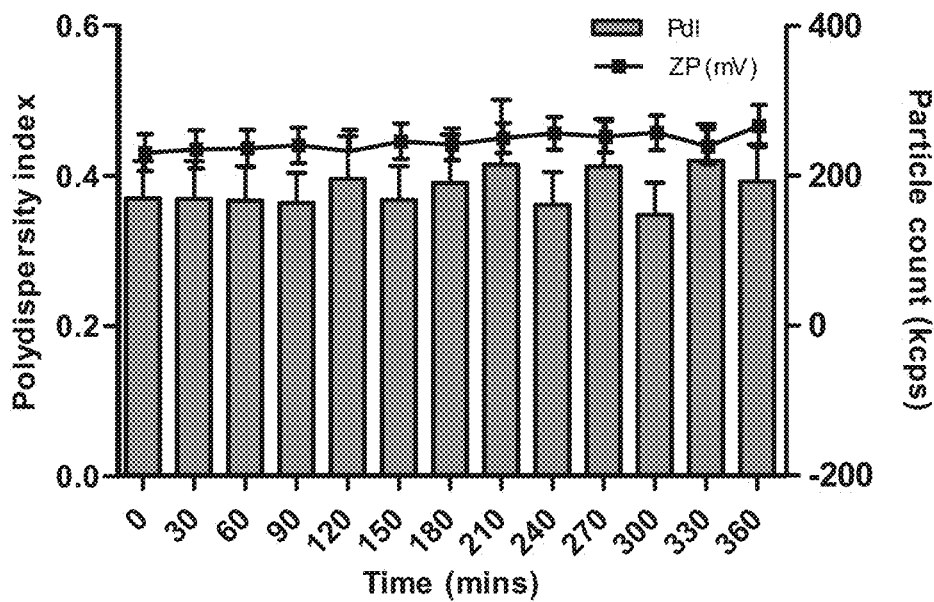

FIG. 43A-B: A: Mean hydrodynamic size of RALA/Runx2 siRNA nanoparticles was determined to assess stability of the particles across a 6 h time period. RALA/Runx2 siRNA nanoparticles were prepared at N:P 12 such that they contained 0.5 μg Runx2 siRNA and 7.25 μg RALA. The mean hydrodynamic size of the nanoparticles was measured at 30 min intervals, starting immediately after formulation until 6 h after, using a Malvern Zetasizer Nano ZS. B: The corresponding PDI and particle count were also recorded. Results are displayed as mean±SEM, n=3, where n represents the number of independent batches prepared for measurement.

Figure 44A:
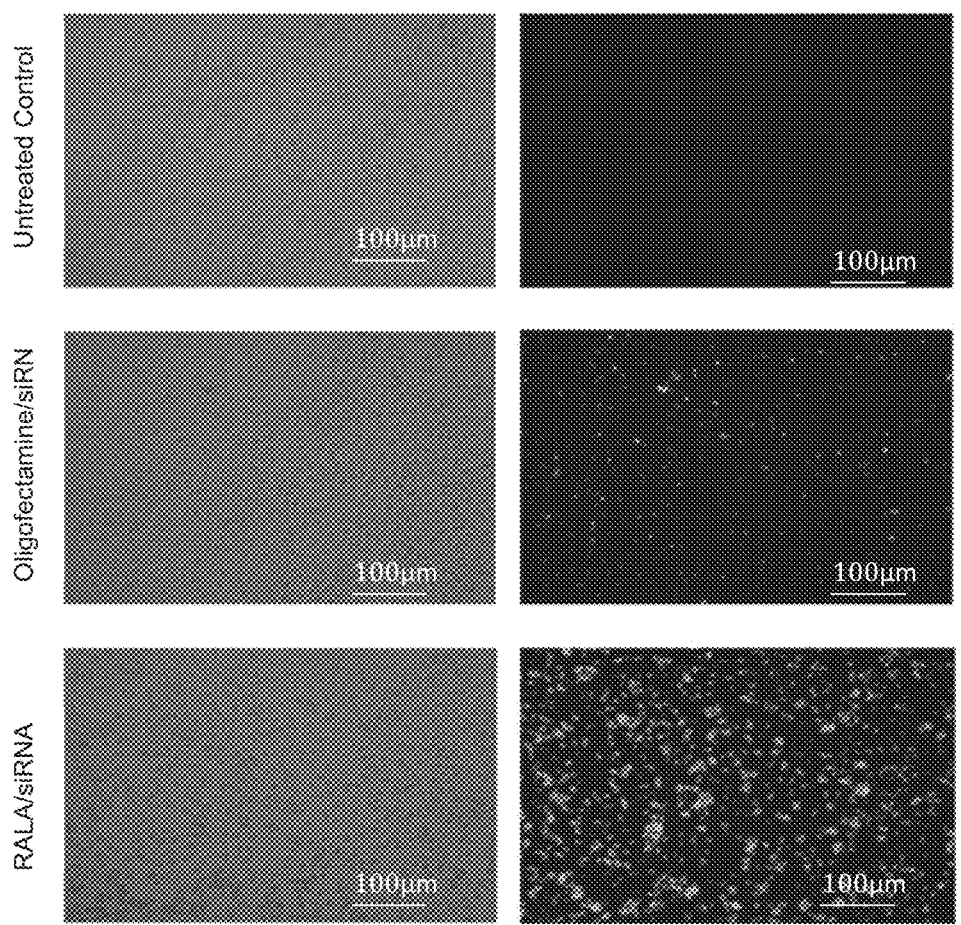
Figure 44B:
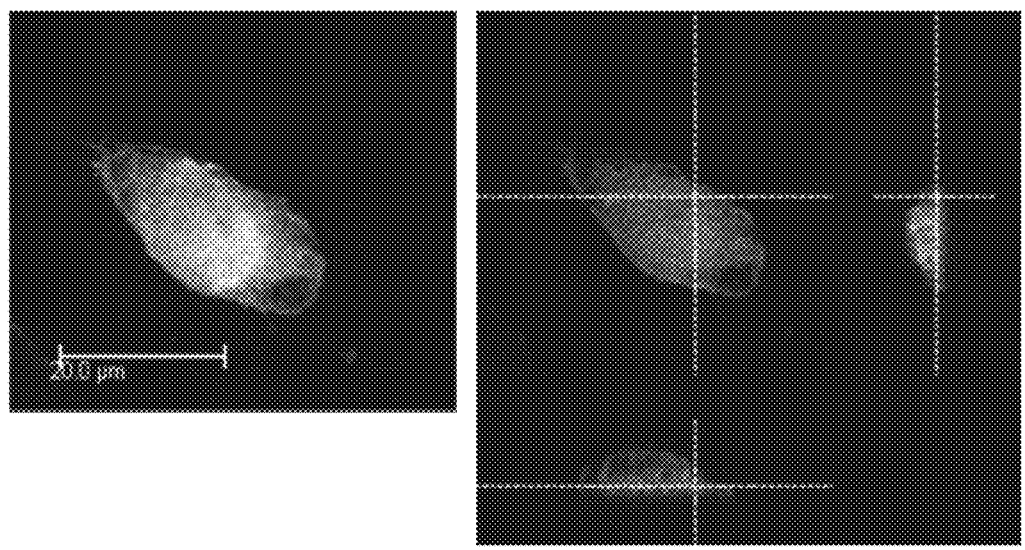

FIG. 44A-B: A: Transfection efficiency of RALA/fluorescent siRNA nanoparticles was assessed in a prostate cancer cell line. PC-3 prostate cancer cells were transfected for 4 h with RALA/fluorescent siRNA nanoparticles prepared at N:P 12 or Oligofectamine. Following the transfection the medium was removed and replaced with RPMI 1640 supplemented with 10% FCS and allowed to incubate for up to 72 h. B: PC3 prostate cancer cells were allowed to adhere to a coverslip overnight having been seeded at a density of 50,000 cells per coverslip prior to transfection with RALA/fluorescent siRNA nanoparticles (green) for 4 h. The cells were then fixed using 2% formaldehyde and stained with Wheat Germ Agglutinin, Alexa Fluor conjugate 488 (red) followed by Hoechst stain (blue), each for 20 min. The coverslips were subsequently mounted onto slides using ProLong Gold Antifade Reagent and sealed the following day. A Leica TCS SP8 confocal microscope was used to image the cells and produce orthogonal sectioning and a Z-stack using Leica software.

Figure 45:
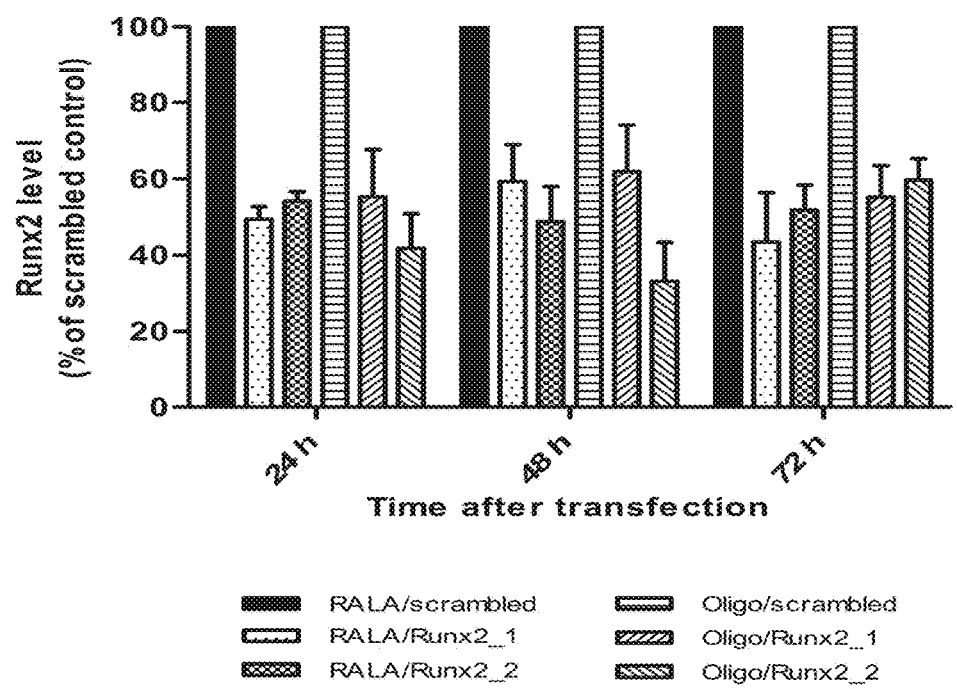

FIG. 45: Quantification of western blotting using image J software to determine the Runx2 knockdown. PC-3 prostate cancer cells were transfected with a 100 nM concentration of Runx2_1, Runx2_2 or non-targeting scrambled siRNA using either RALA peptide or Oligofectamine. Cell lysates were collected 24, 48 and 72 h following the 4 h transfection and run on 8% acrylamide gels. Results are obtained from at least 2 independent repeats.

Figure 46:
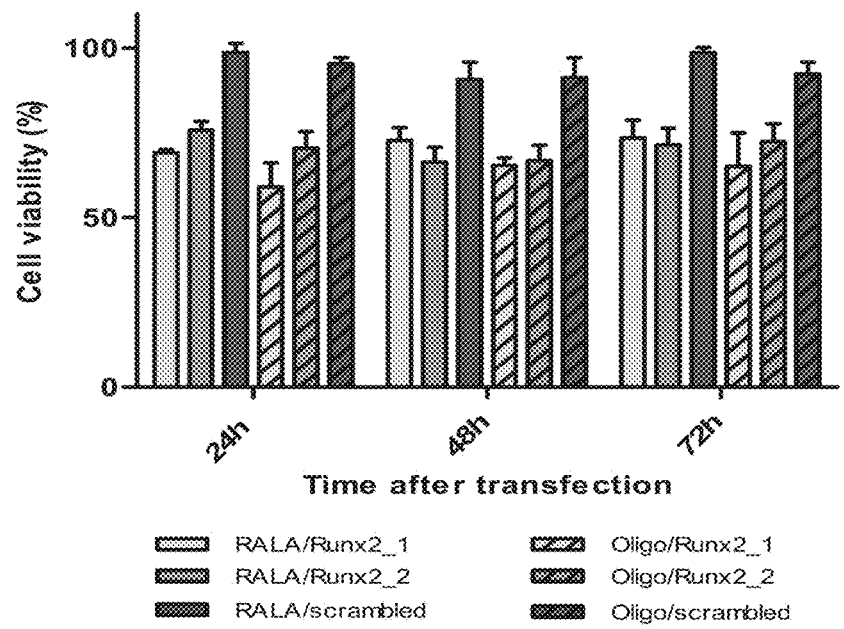

FIG. 46: The effect of Runx2 knockdown on cell proliferation was evaluated using two different delivery systems, namely RALA peptide and the commercial siRNA transfection reagent, Oligofectamine. Transfection with RALA/siRNA nanoparticles at N:P 12 and with Oligofectamine was for 4 h. Medium was then supplemented with RPMI 1640 containing 30% FCS for up to 72 h such that the final concentration of FCS was 10%. Subsequently cells were trypsinised and counted using a haemocytometer. Untreated cells were considered to be 100% viable and viability under all other conditions was calculated based on this. Results are reported as mean±SEM, n=3, where n represents the number of independent batches prepared for analysis.

Figure 47A:
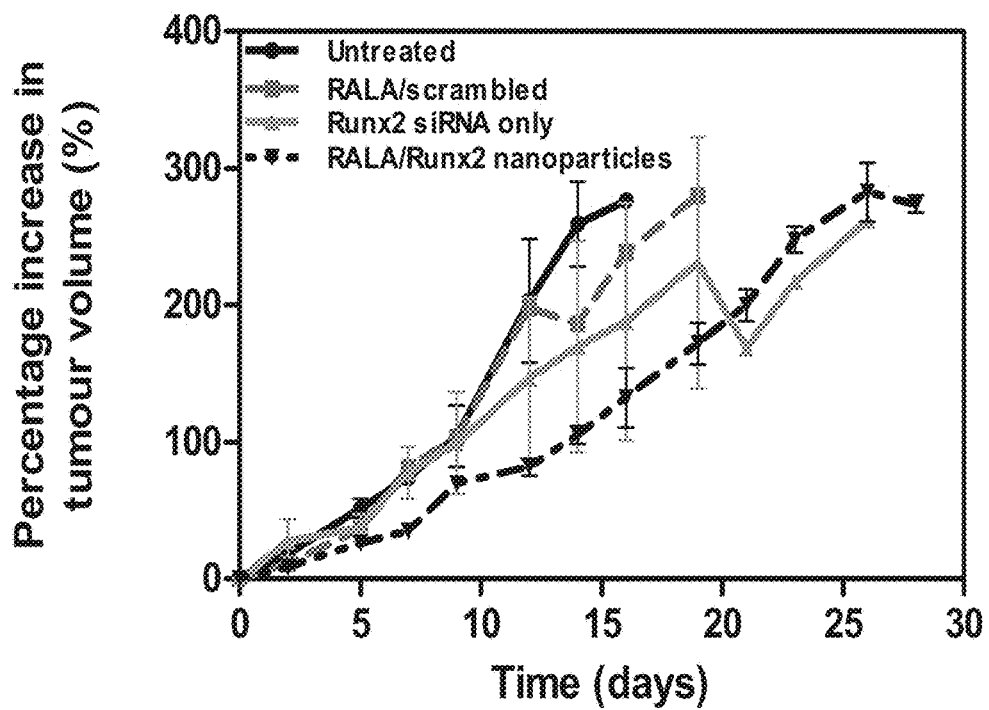
Figure 47B:
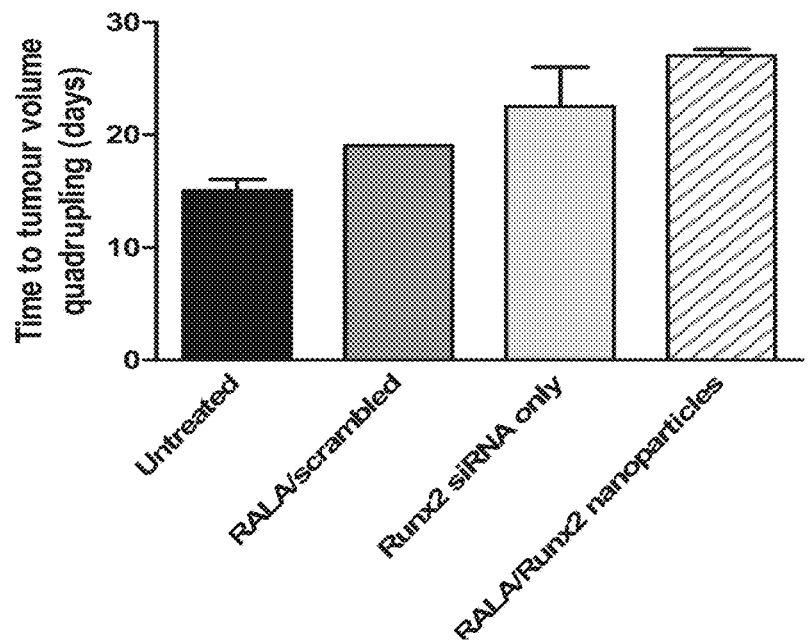
Figure 47C:
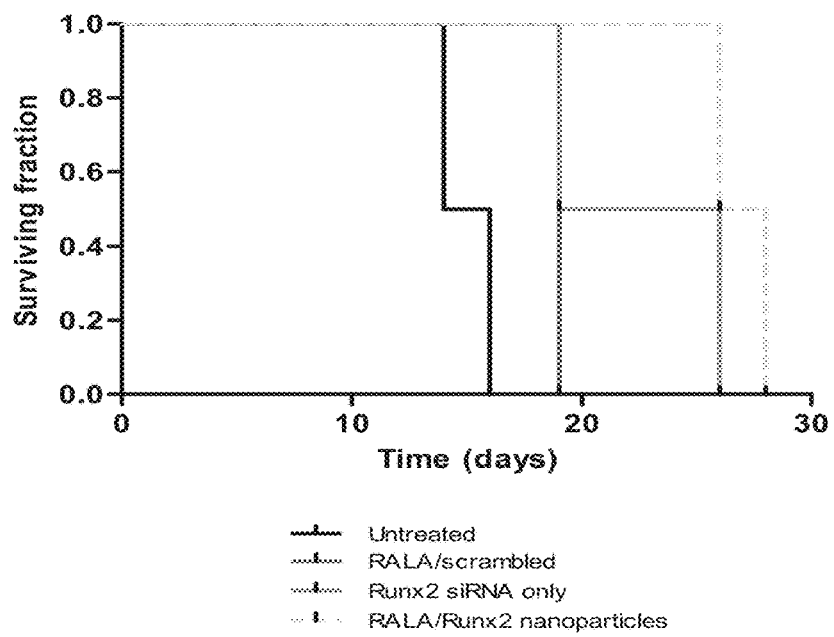
Figure 48A:
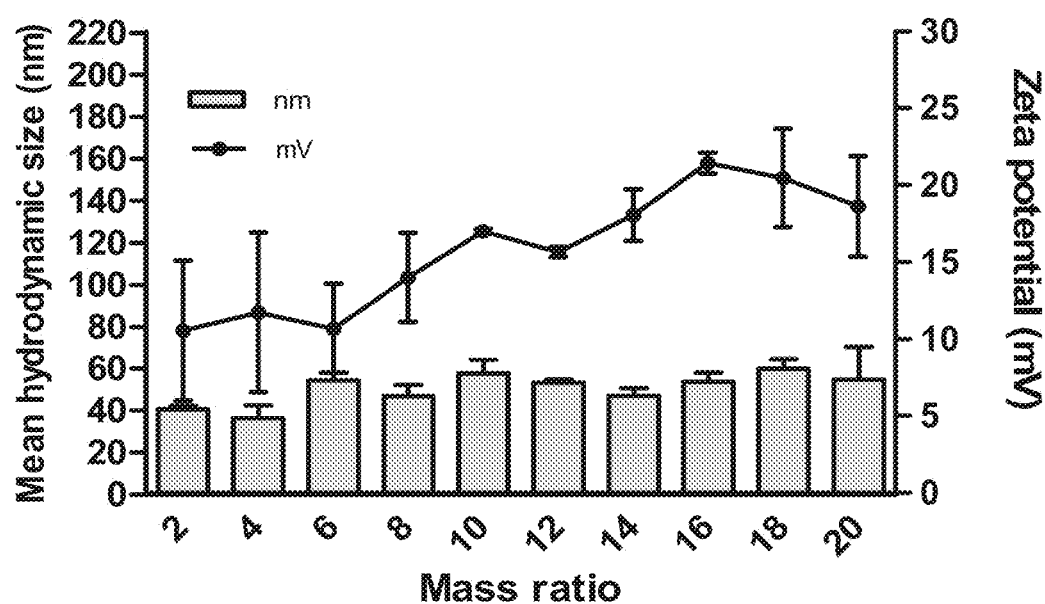
Figure 48B:
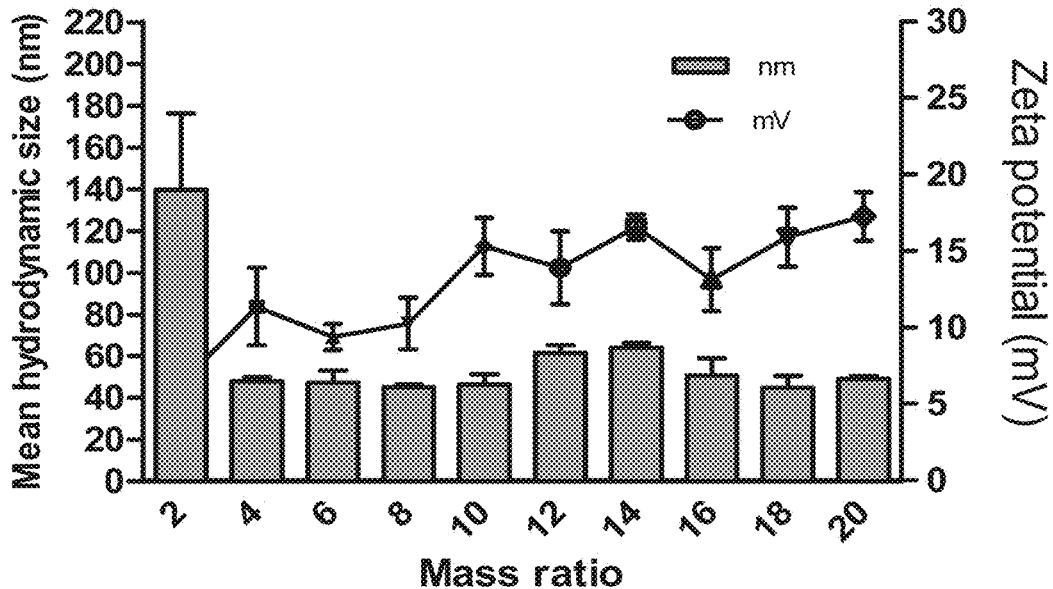
Figure 48C:
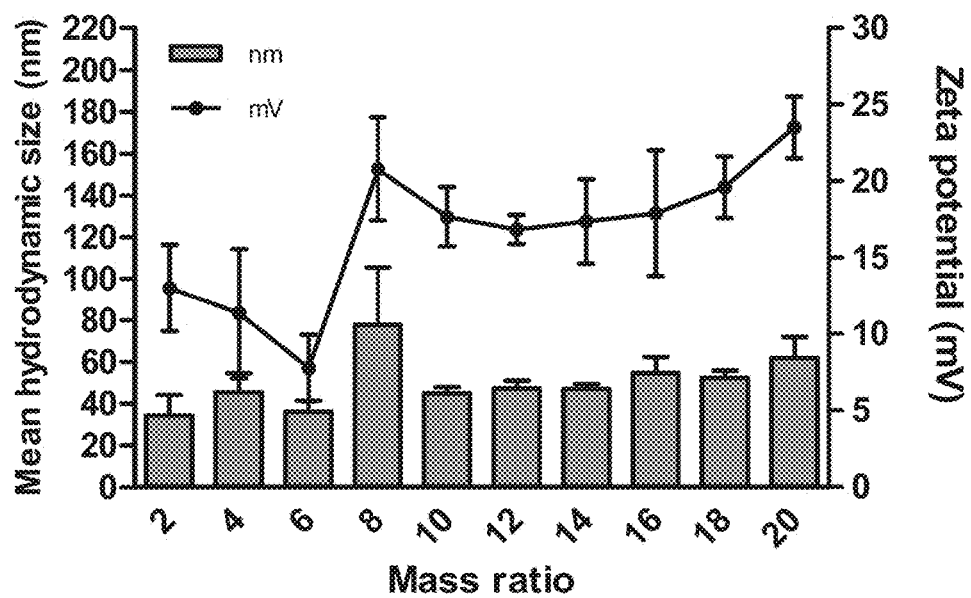
Figure 48D:
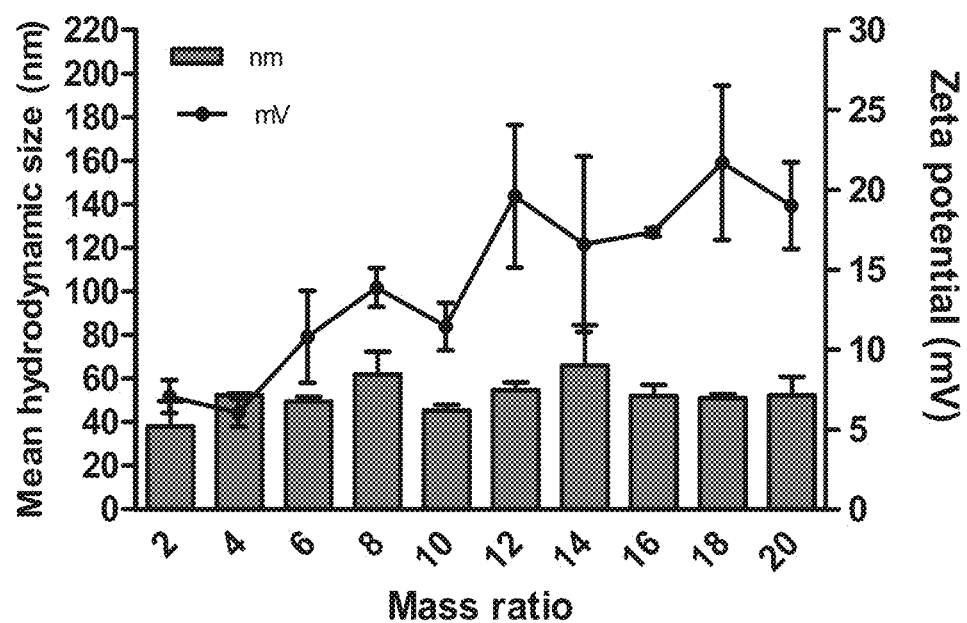
Figure 49A:
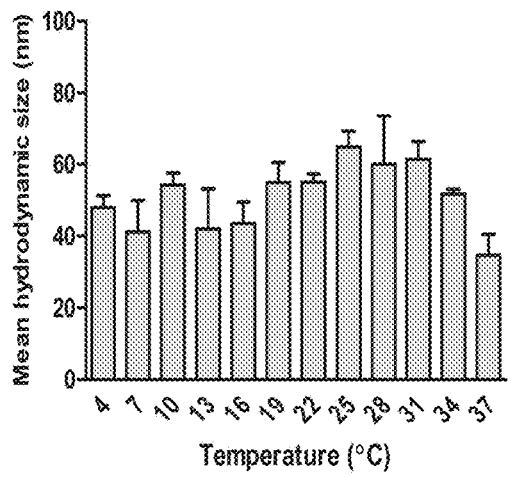
Figure 49B:
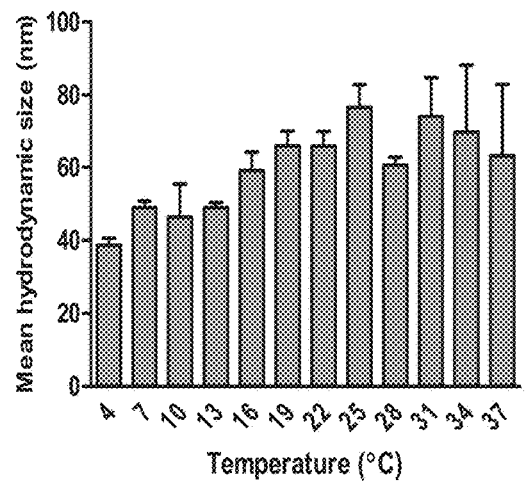
Figure 49C:
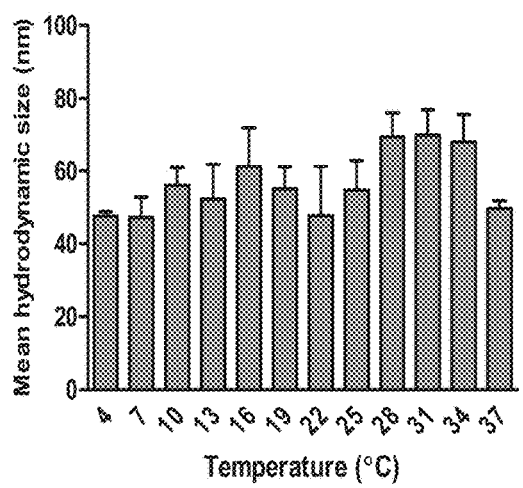
Figure 49D:
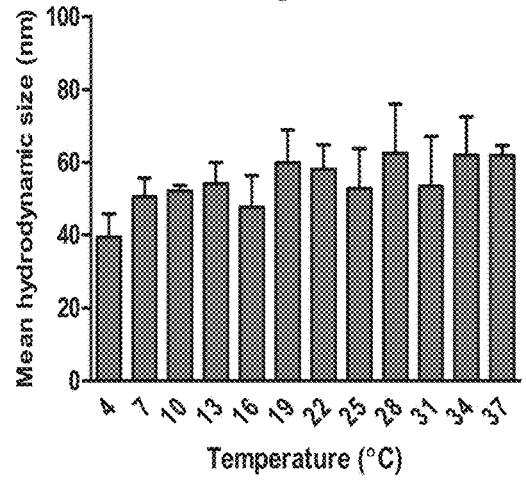
Figure 50A:
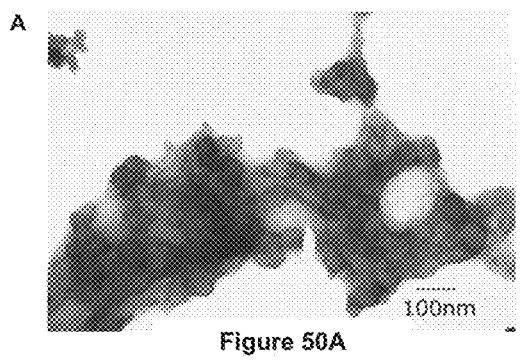
Figure 50B:
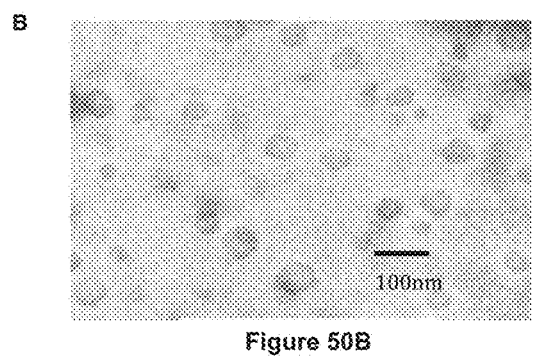
Figure 50C:
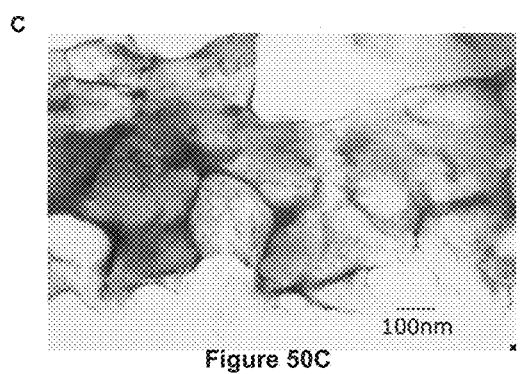
Figure 50D:
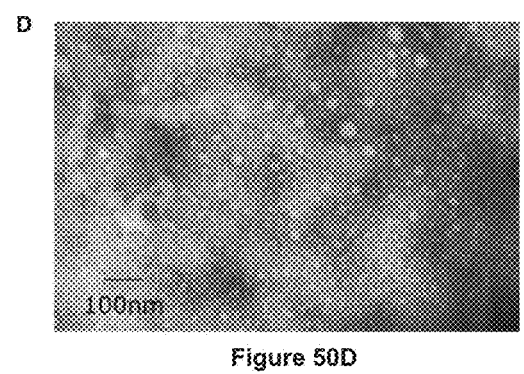
Figure 50E:
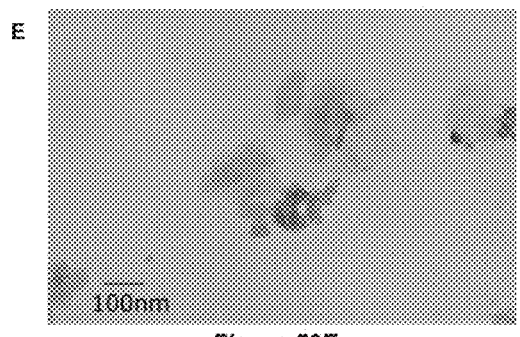
Figure 50F:
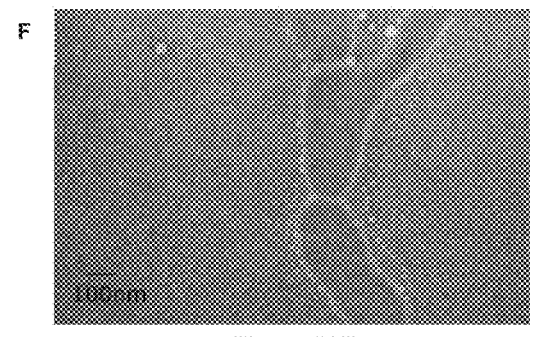
Figure 50G:
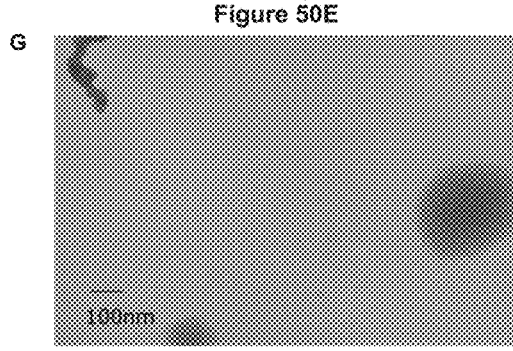
Figure 50H:
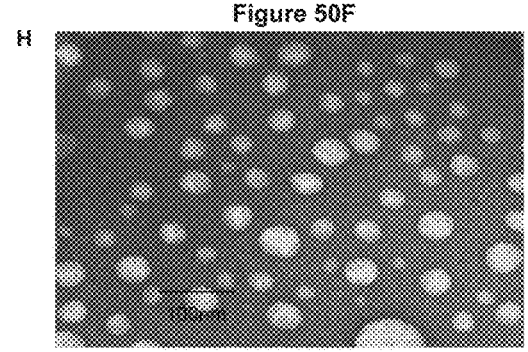

FIG. 47A-C: A PC-3 prostate cancer cell xenograft model was used for the in vivo assessment of RALA as a delivery system for siRNA and the effects of Runx2 knockdown on tumour cell proliferation. Tumours were implanted on the rear dorsum of BALB-C SCID mice and grown until the volume reached approximately 150 mm3. Treatments were once weekly for three weeks via intratumoural injection with mice being assigned randomly to either a water only, RALA/scrambled siRNA nanoparticles, Runx2 siRNA only or RALA/Runx2 siRNA nanoparticles treatment group. Runx2_1 and Runx2_2 siRNA were pooled for the purposes of in vivo analysis. As this was a pilot study the numbers within each group ranged from 1-4. The experimental endpoint was quadrupling of tumour volume. A: Percentage increase in tumour volume over time is presented showing a lower rate of tumour growth when tumours were treated with RALA/Runx2 siRNA nanoparticles. The rate of growth in Runx2 siRNA treated mice was slower than control groups; however, there was a large amount of variability. B: Time taken for tumour growth to quadruple is displayed with high statistical significance in overall survival time between RALA/Runx2 siRNA nanoparticles and water only treated mice (unpaired one-tailed t test p<0.001). However, there is no statistical significance in the difference in survival times of Runx2 siRNA only and RALA/Runx2 siRNA nanoparticles due to the variability of the survival time in Runx2 siRNA only treated mice (unpaired one-tailed t test p>0.05).

C: Kaplan-Meier plot demonstrating the survival of tumour-bearing mice for each of the treatment groups from the start of dosing until the time at which the tumour volume quadruples. Censoring was not required as all animals left the study due to the experimental endpoint being reached.

FIG. 48A-D: Mean hydrodynamic size and zeta potential of A: RALA/alendronate nanoparticles, B: RALA/etidronate nanoparticles, C: RALA/risedronate nanoparticles and D: RALA/zoledronate nanoparticles. RALA/BP nanoparticles were prepared at a range of mass ratios, such that for a mass ratio of 10:1 the nanoparticles contained 1 μg BP and 10 μg RALA. The nanoparticles were incubated for 30 min before their hydrodynamic size and zeta potential were measured using a Malvern Zetasizer Nano ZS. Results are displayed as mean±SEM, n=3, where n represents the number of independent batches prepared for measurement.

FIG. 49A-D: Mean hydrodynamic size of RALA/BP nanoparticles was determined to assess thermal stability over a range of temperatures. RALA/BP nanoparticles were prepared at a range of mass ratios, such that for a mass ratio of 10:1 the nanoparticles contained 1 μg BP and 10 μg RALA. The nanoparticles were incubated for 30 min before the mean hydrodynamic size was measured using a temperature trend function on the Malvern Zetasizer Nano ZS. Results are displayed as mean±SEM, n=3, where n represents the number of independent batches prepared for measurement. A: RALA/alendronate nanoparticles, B: RALA/etidronate nanoparticles, C: RALA/risedronate nanoparticles and D: RALA/zoledronate nanoparticles.

FIG. 50A-H: TEM of the RALA/BP Nanoparticles. Nanoparticles were prepared at a mass ratio of 10:1 and allowed to incubate for 30 min before being loaded onto carbon reinforced formvar coated copper grids. Samples were allowed to dry before being stained with 5% uranyl acetate for 5 min at room temperature. The nanoparticles were imaged using a JEOL 100CXII transmission electron microscope at an accelerating voltage of 80 kV and images were captured onto Kodak 4489 Electron Microscope Film. This was developed using Kodak D19 developer, fixed with Universal fixer, washed and dried. The negatives were then scanned onto a PC as JPEG images. A: Blank grid with no stain; B: Stained blank grid; C: RALA only; D: Alendronate only; E: RALA/alendronate nanoparticles; F: Etidronate only; G: RALA/etidronate nanoparticles; H: Risedronate only; I: RALA/risedronate; nanoparticles; J: Zoledronate only; K: RALA/zoledronate nanoparticles.

FIG. 51A-D: Cell viability was evaluated by manual counting of the viable adherent cells using a haemocytometer. PC-3 prostate cancer cells were seeded in a 96-well flat-bottom tissue culture plate at a density of 1×104 cells per well and incubated in complete culture medium for 24 h. Two hours prior to transfection the cells were conditioned in OptiMEM serum-free medium and subsequently treated with solutions of BP to achieve a final exposure concentration of 5 μM to 1 mM. RALA/BP nanoparticles were prepared using a mass ratio of 10:1 such that the final concentration of BP per well was in the range 5 μM to 75 μM. Cells were incubated at 37° C. with 5% CO2 for 6 h before medium was replaced with completed culture medium and left to incubate for 72 h. Following incubation the cells were trypsinised and counted. Cell viability was expressed as a percentage of the untreated control where the untreated control is considered to be 100% viable. Dose-response curves were obtained for free BP and RALA/BP allowing determination of EC50 values for each. EC50 values refer to the concentration that induces a response halfway between the baseline and the maximum plateau obtained. A: RALA/alendronate and alendronate treated cells; B: RALA/zoledronate and zoledronate treated cells; C: RALA/risedronate and risedronate treated cells; D: RALA/etidronate and etidronate treated cells.

Figure 52A:
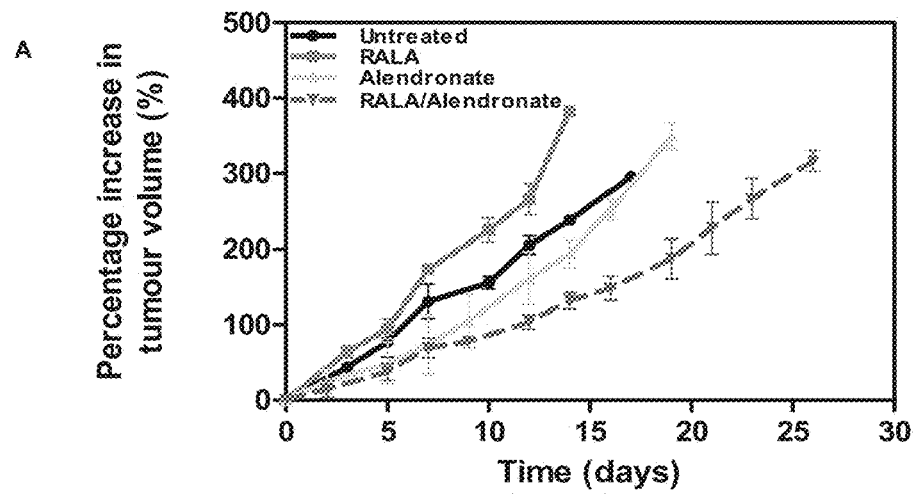
Figure 52B:
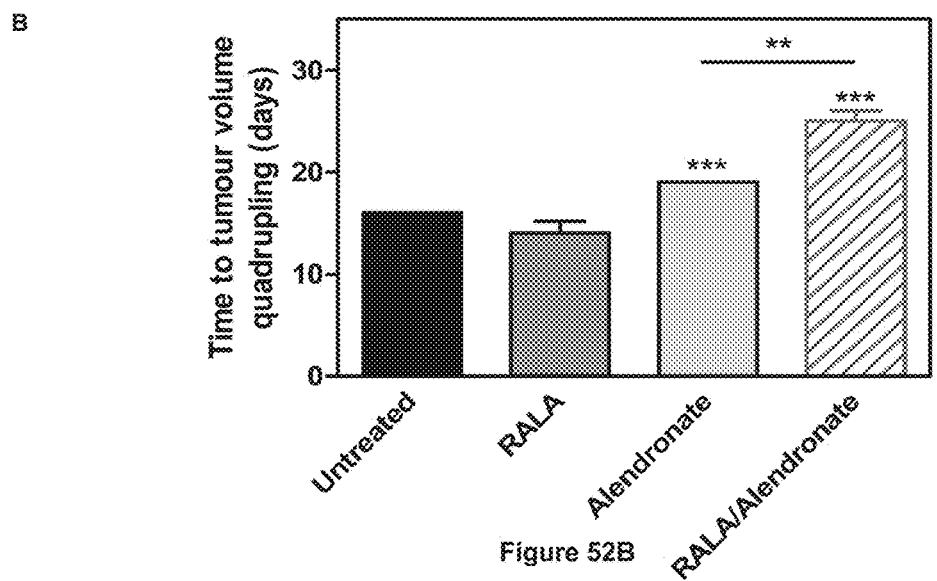
Figure 52C:
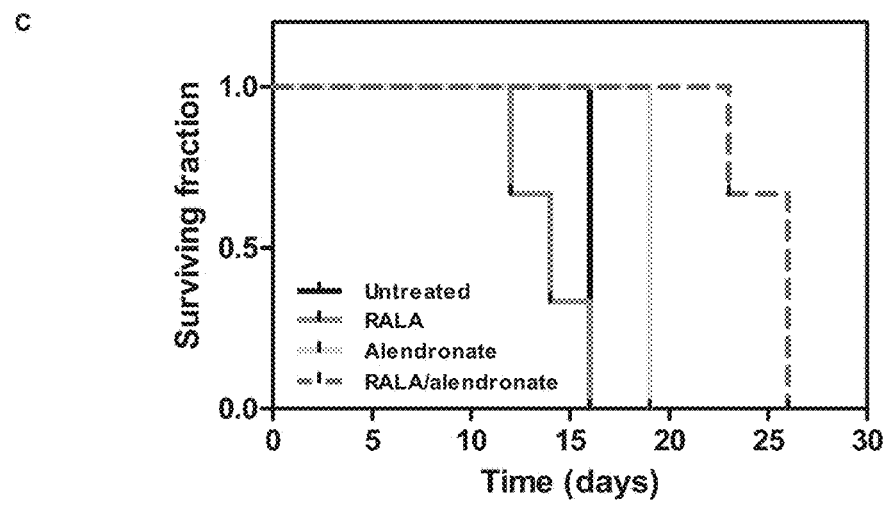

FIG. 52A-C: PC-3 prostate cancer cell xenograft model was used for the in vivo assessment of RALA as a delivery system for BPs. Tumours were implanted on the rear dorsum of BALB-C SCID mice and grown until the volume reached approximately 100 mm3. Treatments were three times weekly for three weeks via intratumoural injection with mice being assigned randomly to either an untreated, RALA only, free alendronate or RALA/alendronate treatment group. Each treatment group consisted of three mice which allowed statistical significance in the outcomes to be observed. The experimental endpoint was quadrupling of tumour volume. A: Percentage increase in tumour volume over time is presented showing a low rate of tumour growth when tumours were treated with RALA/alendronate nanoparticles. The rate of growth in the controls was considerably higher. B: Time taken for tumour growth to quadruple is displayed with high statistical significance in overall survival time between free alendronate and untreated control, and RALA/alendronate and untreated control (both p<0.001). Furthermore, there is statistical significance in the difference in survival times of free alendronate and RALA/alendronate (p<0.01). C: Kaplan-Meier plot demonstrating the survival of tumour-bearing mice for each of the treatment groups from the start of dosing until the time at which the tumour volume quadruples. Censoring was not required as all animals left the study due to the experimental endpoint being reached FIG. 53: Encapsulation assay of RALA/pEGFP-N1 nanoparticles over a range of N:P ratios (0-15). RALA/pEGFP-N1 nanoparticles were incubated for 30 mins with Picogreen and the fluorescence intensity of the resulting complexes measured at 520 nm using a spectrofluorometer. The measurements are reported as mean±SEM, (n=3).

Figures 53, 54:
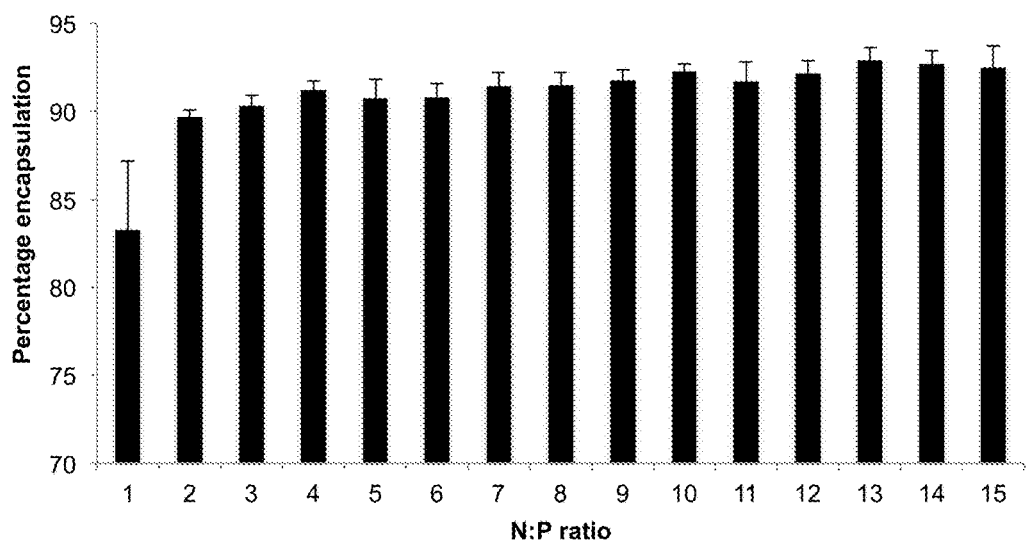

FIG. 54: The amino acid sequence of the RAT peptide consisting of three moieties, each with a specialist role to fulfil in delivering therapeutic DNA to target cells (e.g. PC-3); a TMTP-1 metastatic targeting peptide (TP) for specificity, an alpha helical spacer and RALA.

Figure 55A:
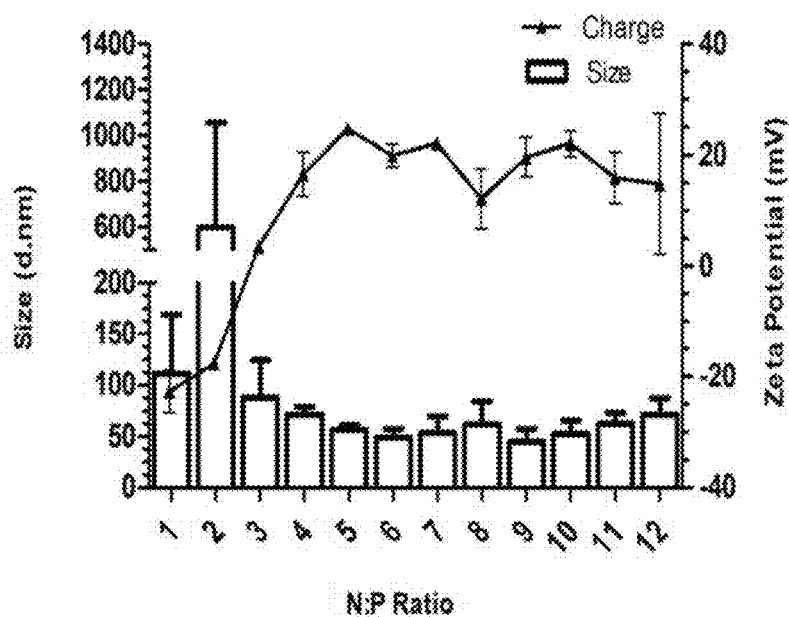
Figure 55B:
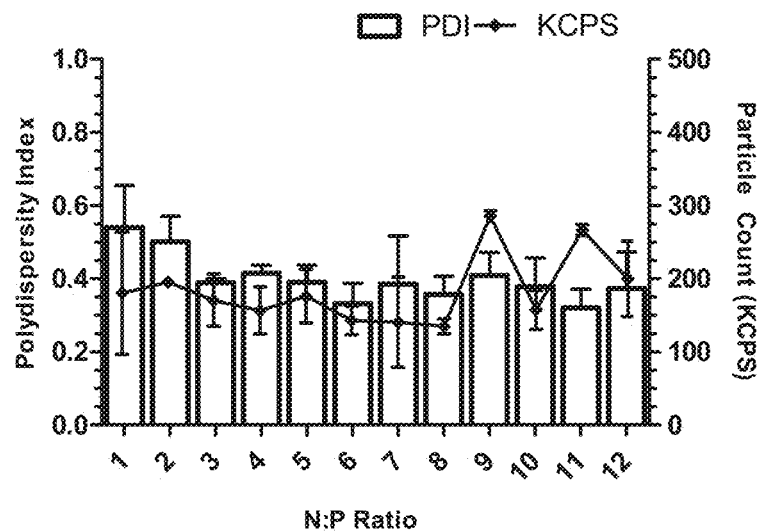

FIG. 55A-B: Zetasizer analysis of RAT/pEGFP-N1 nanoparticles over a range of nitrogen[peptide]:phosphate[DNA] (NP) ratios. A) Hydrodynamic size (nm) and surface charge (mV) B) Count rate (kilo counts per second and Polydispersity Index. Nanoparticles less than 200 nm are formed at N:P ratios of 3-12 with a charge in the 20 mV range. N:P12=71.03 nm±11.36 nm; 17.49 mV±11.92. Mean±SEM (n=3). A minimum of 15 measurement runs per repeat.

Figure 56:
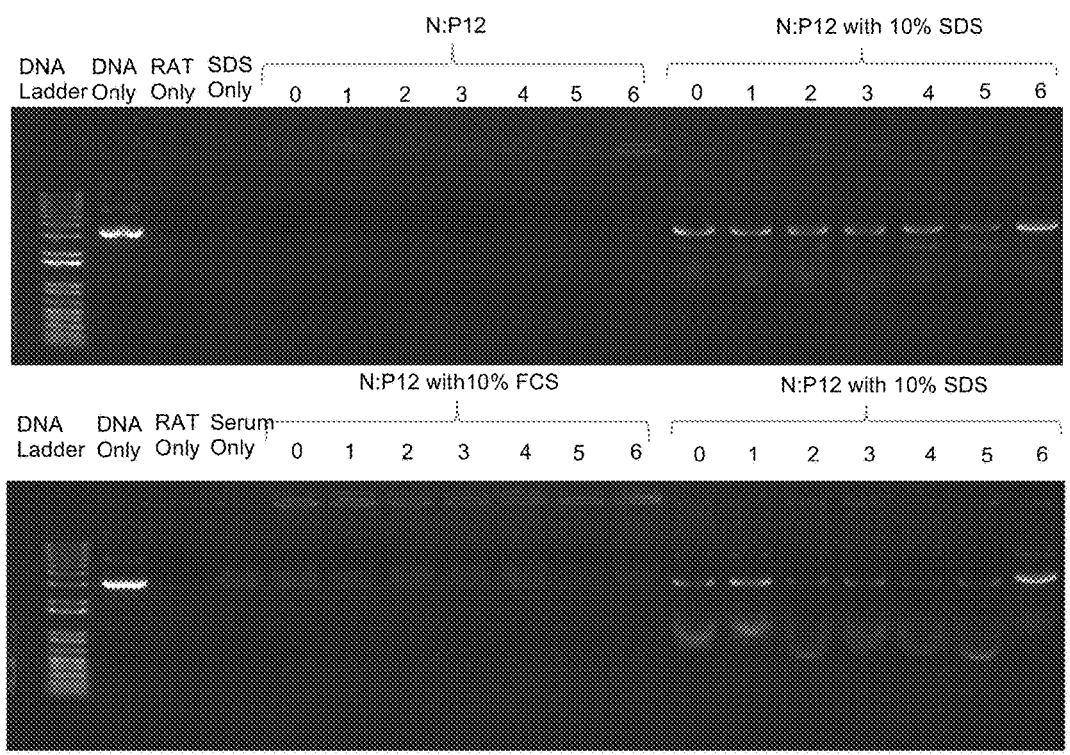

FIG. 56: N:P12 RAT/pEGFP-N1 nanoparticles incubated for 0-6 h (labelled 0-6) with and without the presence of 10% foetal calf serum. Replicates were de-complexed with 10% sodium dodecyl sulphate or 10 min to confirm the integrity of DNA. Nanoparticles were run on a 1% agarose gel for 1 h at 100 volts. Representative image of three experiments.

Figure 57:
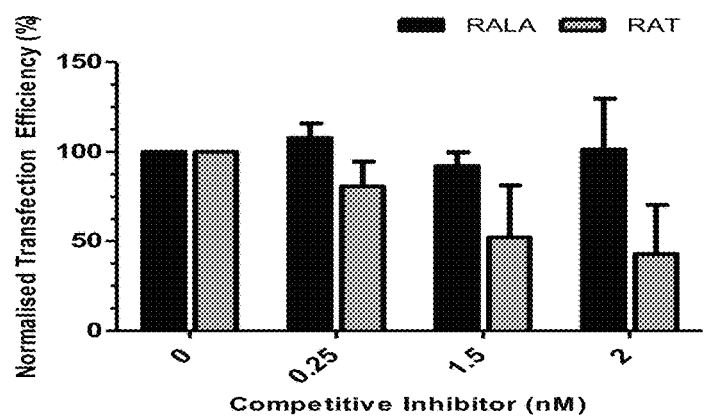

FIG. 57: Cells were transfected with RAT/pEGFP-N1 N:P12 nanoparticles with the additional of inhibiting peptide, TMTP1, and control peptide, scrambled TMTP1 (0.25 nM, 1.5 nM and 2 nM). Cells were fixed in formaldehyde for flow cytometry. The measurements are reported as mean±SEM, (n=3).

Figure 58:
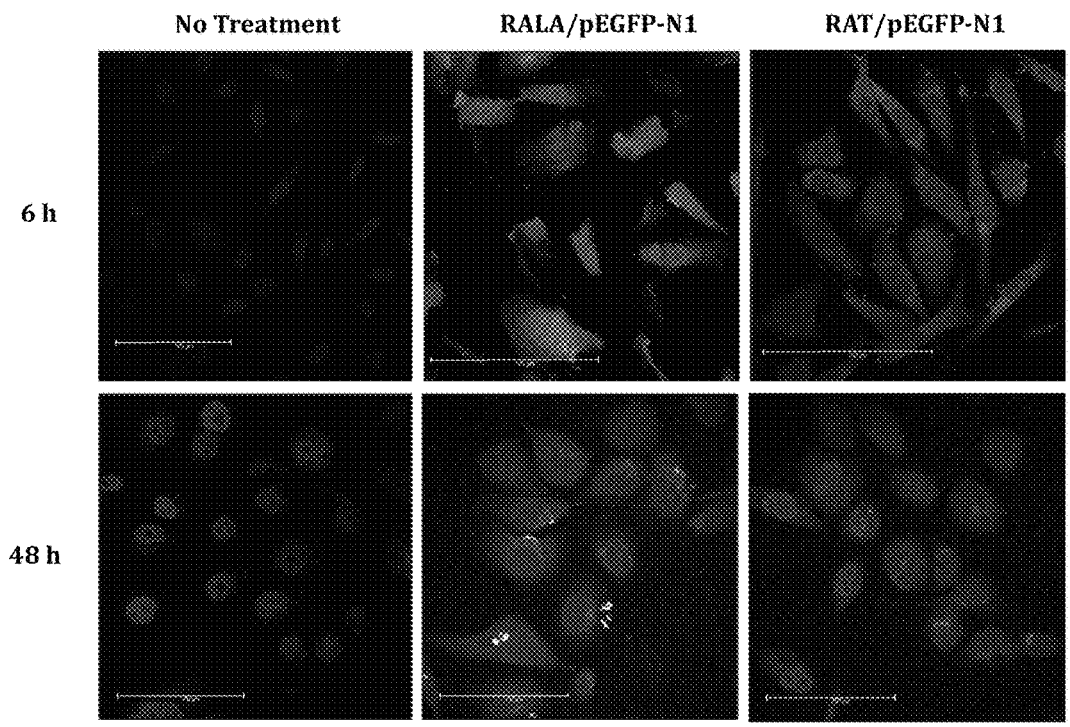
Figure 59A:
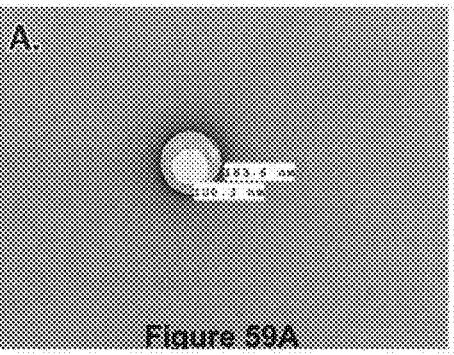
Figure 59B:
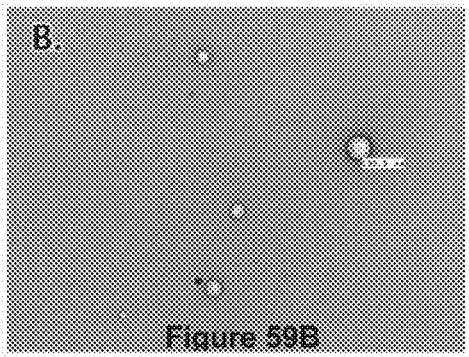
Figure 59C:
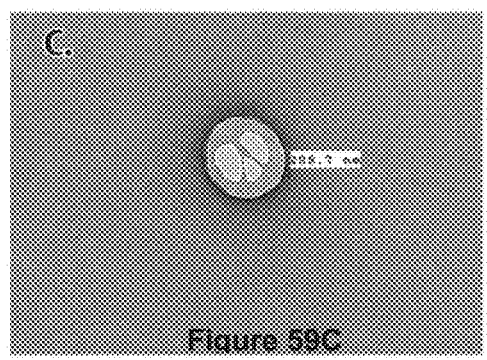
Figure 59D:
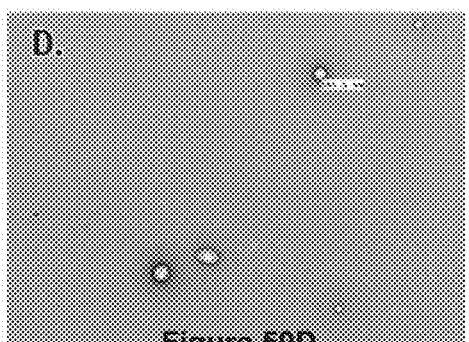
Figure 59E:
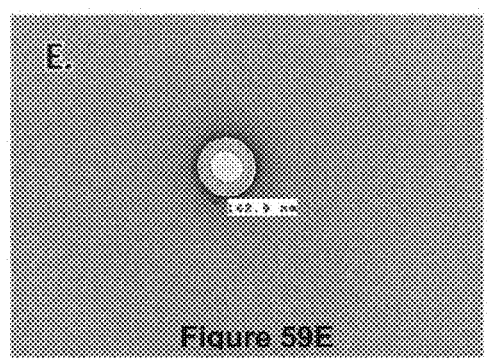
Figure 59F:
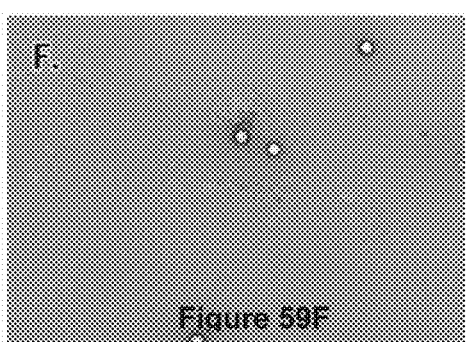
Figure 59G:
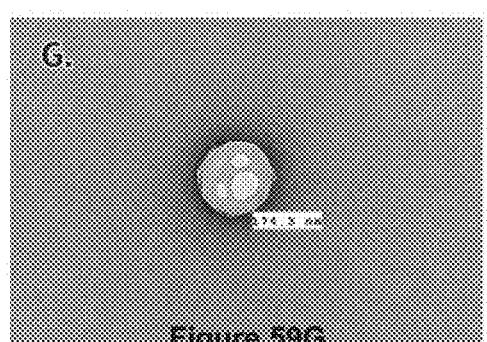
Figure 59H:
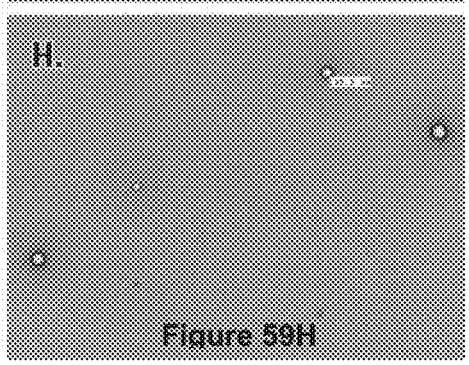

FIG. 58: Confocal microscopy of RAT and RALA/pEGFP-N1 transfected cells at 6 and 48 h. PC3 prostate cells were allowed to adhere to a coverslip overnight having been seeded at a density of 50,000 cells, per coverslip, prior to transfection with RALA/Cy3 labeled pEGFP-N1 DNA (red) or RAT/Cy3 labeled pEGFP-N1 DNA (red) for 6 and 48 h. The cells were then fixed for 10 minutes using 2% formaldehyde and stained with Hoeschst stain (blue) for 2 minutes. The coverslips were subsequently mounted onto slides using ProLong Gold Antifade Reagent and sealed. A Leica TCS SP8 confocal microscope was used to image the cells and produce a Z-stack. Gene expression produced by pEGFP-N1 (green) is distinguishable at certain time points FIG. 59A-H: Transmission electron microscopy of various composite nanoparticles. A. & B. PLGA; C & D: PLA10-PEG2; E & F: PLA25-PEG5; G & H: PLA50-PEG5. Images on the left were taken at 25,000×, images on the right were taken at 6,000× magnification.

FIG. 60: The amino acid sequence of a. RALA and b. PEGylated RALA. PEG will potentially minimize opsonisation and also increase tumour targeting via the enhanced permeation and retention effect (EPR).

EXAMPLES

Example 1

Generation of RALA Peptide

The following peptide (called "RALA" herein) was synthesised commercially in accordance with conventional techniques with the amino acid sequence (SEQ ID No. 1)
WEARLARALARALARHLARALARALRACEA RALA arrives in a lyophilised form and is reconstituted with molecular grade water to a desired concentration, aliquotted out and stored at −20° C. until further use. An aliquot is then taken as needed and defrosted on ice.

Example 2

Formation and In-Vitro/In-Vivo Testing of RALA/siRNA Nanoparticles

Materials and Methods
Calculation of N:P Ratio

DNA was complexed with either the RALA peptide at various N:P ratios (the molar ratio of positively charged nitrogen atoms to negatively charged phosphates in DNA). As the number of positive side-groups in a protein side chain depends upon the sequence, different proteins will have differing numbers of positive charges per unit mass. In order to calculate this, the following equation was used:

$$NP = M_{protein} / M_{DNA} C_{NP}$$

Where M protein is the mass of a protein, M DNA is the mass of DNA and C NP is the N:P constant. The N:P constant is the ratio of the protein's side chain positive charge density to the DNAs backbone density, with the charge density being the charge of a substance divided by its molecular mass. For the protein, lysine, arginine and histidine side groups are counted. For the DNA the average mass of one single base pair, and the charge of the phosphate group are used. For RALA an N:P ratio of 1 is 1.45 µg of RALA:1 µg of DNA.
Formation of the Nanoparticles The DNA/siRNA was diluted in molecular grade water to 200 µg/ml. 1 µg of DNA was added to a 1.5 ml eppendorf centrifuge tube. For 1 µg of DNA the final volume was 50 µl. The appropriate volume of protein to use to make the desired N:P ratio was added to a separate tube and the volume made up to 50 µl with molecular grade water. The 50 µl solution containing the protein was added to the 50 µl containing the DNA. The molecular grade water was added to the DNA before the protein. The tube was flicked five times in order to mix the content. The complexes were allowed to incubate for 30 minutes at room temperature prior to use. The results are shown in FIGS. 2 & 28.
Gel Retardation Assay RALA/DNA complexes were prepared at N:P ratios 1-15. Following incubation at room temperature for 30 minutes, 30 µL of the samples (corresponding to 0.6 µg of DNA) were electrophoresed through a 1% agarose gel containing 0.5 µg/mL ethidium bromide (EtBr) (Sigma, UK) to visualize DNA. A current of 80 V was applied for 1 h and the gel imaged using a Multispectrum Bioimaging System (UVP, UK). The purpose of this assay is to determine which N:P ratio/s neutralise the DNA. The assay works upon the principle that when complexes are formed with an excess positive charge DNA remains in the wells or migrates up the gel, hence, no DNA band will be visible following gel electrophoresis. However, DNA alone or complexed to give a net negative charge will migrate down the gel (FIG. 27).
Nanoparticle Size and Charge Analysis In order to obtain particle size and charge distributions the mean hydrodynamic particle size measurements RALA complexes were performed using Dynamic Light Scattering (DLS). Dynamic Light Scattering is based upon the principle that when particles are illuminated with a laser, due to Brownian motion there will be scattering of the light. The intensity of the scattered light fluctuates as a result of this Brownian motion caused by bombardment of the particles by solvent molecules. A correlation curve reflecting the decay rate is generated based on fluctuations of the scattered light where a slower correlation decay rate represents a slower moving particle. Based on the Stokes-Einstein equation larger particles move more slowly and, thus, the correlation function can be used to determine the size distribution of the particles. dynamic light scattering (DLS) was used.

Surface charge measurements of the RALA nanoparticles were determined by Laser Doppler Velocimetry. The zeta potential of the particles was measured using disposable foltable zeta cuvettes. Zeta cuvettes for the measurement of zeta potential were first washed with 70% ethanol, followed by two rinses with double distilled H2O prior to loading the sample. Enough diluted sample used for size measurement was used for determination of zeta potential.

The nanoparticles were made up at an appropriate range of N:P ratios with at least using 2 µg of DNA in each sample. Nanoparticles were analysed using either and analysis was completed on either the Zetasizer-HS3000 (Malvern Instruments) or the Zetasizer-Nano instrument with DTS software (Malvern Instruments, UK). Zetasizer-Nano (Malvern Instruments) (FIGS. 3, 9, 17-21, 41, 48 & 55).
Incubation Stability Study of RALA Nanoparticles This assay is designed to illustrate the stability of RALA complexes to indicate the optimal time period for nanoparticle formation. Following incubation at room temperature for 30 min the mean hydrodynamic size and zeta potential were measured using the Malvern Zetasizer NanoZS with DTS software at 15 or 30 min intervals over a period of 360 min. Size and zeta potential are reported as mean±SEM, n=3, where n represents the number of independent batches prepared for measurement (FIGS. 29b, & 43).

Temperature Stability Study of RALA Complexes

This assay determines the stability of the nanoparticles over a range of temperatures. Following preparation of the nanoparticles by incubation at room temperature for 30 min the mean hydrodynamic size and zeta potential were measured over a temperature range of 4-37° C. in 4° C. intervals using the Malvern Zetasizer NanoZS with DTS software. The sample was allowed to equilibrate at each temperature for 120 sec before measurements were taken in triplicate. Results are reported as mean±SEM, n=3, where n represents the number of independent batches prepared for measurement (FIG. 29a, 42, 49).

Serum Stability Assay

In order to determine the stability of the RALA nanoparticles when exposed to serum the following procedure was carried out. Six replicates of the complexes at NP ratios 5, 10 and 15 were made. Each N:P ratio was split into 3 aliquots or in the case of RALA 18 aliquots. 10% foetal calf serum was added to 12 of the aliquots. The 18 aliquots were incubated at 37° C. Every 55 min SDS (sodium dodecyl sulphate (Sigma, UK)) was added to one of aliquots containing serum for each N:P ratio which were then incubated for a further 5 min. For RALA the stability was assessed over a 6 h time course. Loading dye (Ficoll (Sigma, UK), Tris-HCl, bromophenol blue (Sigma, UK) in ddH2O) was added to all the aliquots prior to loading onto an ethidium bromide prestained 0.8% agarose-TAE gel. A current of 80V was applied for 1 h and the gel was visualised using a Multispectrum Bioimaging System (UVP, UK). (FIG. 5, 7a (with trehalose) 10 (with siRNA), 30, 56 (RAT nanoparticles))

Transmission Electron Microscopy

In an attempt to confirm the results obtained by DLS and obtain additional information about the structure of the nanoparticles Transmission Electron Microscopy was employed. The RALA complexes were prepared as pert or standard conditions and 5 µl was pipetted onto formvar coated copper grids (Agar Scientific, UK) and allowed to air dry overnight. Subsequently samples were stained with 5% aqueous 5% uranyl acetate for 5 minutes and allowed to dry overnight before visualisation. The nanoparticles were imaged using JEOL 100CXII transmission electron microscope at an accelerating voltage of 80 kV (FIG. 2 (siRNA), 15 (Alendronate), 28 (GFP DNA), 50 (Bisphosponates)).

Freeze Drying of the Nanoparticles

700 µl of RALA-pEGFP-N1 nanoparticles were subject to freezing for 1 h at −40° C. This was followed by primary drying at −40° C. and 60 mTorr for 24 h. This was followed by the secondary drying program; 3 h at −35° C. and 120 mTorr, 3 h at −30° C. and 190 mTorr, 3 h at −25° C. and 190 mTorr and 6 h at 20° C. (FIG. 7b).

Transfection of ZR-75-1 & PC-3 Cells in 96 Well Plates with the RALA Nanoparticles In order to test the RALA in vitro, small scale transfections were performed carried out. 5×104 cells were seeded onto each well of a 96 well plate and the cells incubated under with complete medium standard conditions for 48 hours. The medium was subsequently removed from the plates and 100 µl of transfection medium (Optimem Invitrogen, UK) was added to each well. Cells were incubated for 2 hours at 37° C. and 5% CO2 standard conditions. In the meanwhile complexes were made up using 1 µg of plasmid DNA with the RALA vector and added to the cells when the two hours had passed. 100 µl of the each N:P ratio were added to each well of the cells. Cells were then incubated for a further 4 hours under standard conditions and the medium with RPMI-1640 supplemented with +10% FCS. (FIG. 4, 31 (+Chloroquine), 32 (+Bafilomycin), 33 (+KALA NPs), 34 (+Lipofectamine), 35).

Flow Cytometry to Quantify Fluorescent Intensity

ZR-75-1 & PC-3 cells that were transfected with RALA/pEGFP-N1 complexes were trypsinised and washed twice with 2% formaldehyde in phosphate buffered saline. The expression of green fluorescent protein was measured by flow cytometry using FACS calibur system (BD Bioscience, UK). The data was analysed using the Flo-Jo software program and fluorescent intensity is reported at 4% gating. (FIG. 7b, 11, 31, 32, 33, 34, 35, 57 (+RAT/pEGFP-N1)).

Cell Proliferation Assay

Cell viability was evaluated by manual counting of the viable adherent cells using a haemocytometer as described in. PC-3 prostate cancer cells were seeded in a 96-well flat-bottom tissue culture plate at a density of 1×104 cells per well and incubated in complete culture medium for 24 h. Two hours prior to transfection the cells were conditioned in OptiMEM serum-free medium (Invitrogen, UK) optimised for transfection. Cells were treated with solutions of BP to achieve a final exposure concentration of 5 µM to 1 mM. RALA/BP nanoparticles were prepared using a mass ratio of 10:1 such that the final concentration of BP per well was in the range 5 µM to 75 µM. Cells were incubated at 37° C. with 5% CO2 for 6 h before medium was replaced with completed culture medium and left to incubate for 72 h. Following incubation the cells were trypsinised and counted. Cell viability was expressed as a percentage of the untreated control where the untreated control is considered to be 100% viable. Dose-response curves were obtained for free BP and RALA/BP allowing determination of EC50 values for each. EC50 values refer to the concentration that induces a response halfway between the baseline and the maximum plateau obtained (FIG. 46, 51).

WST-1 Cell Viability Assay

The WST-1 assay is a colorimetric assay that can analyse the number of viable cells present and hence, indicate the toxicity of complexes added to cells in vitro. The assay is based on the cleavage of tetrazolium salts that are added to the culture medium. The stable tetrazolium salt WST-1 is cleaved to a soluble formazan by a cellular mechanism that occurs primarily at the cell surface. This WST-1 cleavage is dependent on the glycolytic production of NAD(P)H in viable cells, therefore, the amount of formazan dye formed directly correlates to the number of metabolically active cells in the culture.

Cells were transfected and the complete medium was discarded at a range of time points and replaced with 100 µL Opti-MEM with 10% WST-1 reagent (Roche, UK). Cells were incubated for 2 h under standard cell culture conditions. Subsequently the plates were shaken for 1 min and absorbance measured at 450 nm on an EL808 96-well plate reader (Biotek, USA). The measured absorbance values are expressed as a percentage of the control where the control is defined as 100% viable (FIG. 36).

Intradermal Tumour Model in BALB-C SCID Mice

ZR-75-1 or PC-3 cells were trypsinised until they had detached and 8 ml of medium was added per flask. The cell suspension was transferred into 20 ml universal tubes. The cells were and centrifuged for 5 minutes at 80 g. Cells were resuspended in RPMI+10% FCS and counted using a Coulter Counter (Beckman Coulter, UK). Cells were subsequently centrifuged as before, and resuspended at 108 cells per ml in PBS before being diluted 1: in 1 in matrigel (BD Biosciences, UK). The matrigel cell suspension was loaded into syringes and kept on ice until implantation.

Matrigel was only required for the ZR-75-1 cells. Balb-C SCID mice were anaesthetised with isofluorane (Abbott, UK) and the rear dorsum was shaved. Subsequently the skin on the rear dorsum was pinched between forefinger and thumb and 5×106 cells (100 µl) were injected intradermally using with a 26 G needle (BD Biosciences, UK) at the prepared site. Mice were observed while recovering from the anaesthesia and then subsequently returned to their box (FIG. 6, 47, 52).

Tumour Size Measurements

The length (L), width (W) and depth (D) of the tumour was measured using vernier with calipers. Subsequently the volume of the tumour was estimated by using the equation, $V=\pi LWD/6$, an approximation of $V=4/3\pi r3$.

Intra-tumoural Injections

Mice were anaesthetised with isofluorane and a 26 G needle (BD Biosciences, UK) was inserted bevel side down into the tumour. 100 µl of the nanoparticle treatment was injected slowly before rotating the needle and removing very slowly. For the multiple dose regimen used in this study a 'round the clock' system of injections was used. Recovery of mice from anaesthesia was monitored (47,52).

Intra-Venous Injections

Mice were placed into a heat box at 36° C. for 5 minutes or until both of the tail veins were clearly visible. They were then moved into a heavy brass restrainer and injected with 50-100 µl of treatment into the tail vein with an insulin syringe (BD Biosciences, UK) equipped with 28 G needle. Mice were then replaced into the cage and monitored for signs of suffering associated with the injection. Mice found to be suffering or dying were euthanized by a schedule one protocol. (FIG. 6, 40).

Harvesting Blood Via Cardiac Puncture and Collection of Serum

For the harvesting of blood and intraperitoneal macrophages, cervical dislocation was the preferred method of euthanasia. Cardiac puncture was performed using a 21 G gauge needle (BD Biosciences, UK). The needle was placed horizontally slightly to the left side of the sternum to go up through the diaphragm. The needle was then withdrawn very slowly until ⁻500 µl of blood was collected and placed in an eppendorf. The eppendorf was then stored at room temperature with an open lid to facilitate coagulation. After 30 min the eppendorfs were centrifuged at 2000 rpm for 10 min. The supernatant containing the serum was carefully decanted and placed into a clean eppendorf and stored at −20° C. until further use. When harvesting intraperitoneal macrophages an incision was made and the peritoneal cavity was flushed out with 30% sucrose (Sigma, UK) solution. The macrophages were stored at 4° C. until they could be cultured (FIG. 8).

Western Blots with in vitro and in vivo Samples

Organs were homogenised and lysed in RIPA overnight. The samples were centrifuged at 5000 g for 10 minutes and the supernatant transferred to a fresh eppendorf tube. The lysate was diluted 1:2 in laemmli buffer, boiled for 10 minutes and loaded onto a Bis-Tris gel. Cells were put directly into laemmli buffer. The gel was run at 120V till the dye reached the bottom. The gel was and transferred into a western cassette. The protein was subsequently transferred for 2.5 hours at 25V onto a nitrocellulose membrane (Amersham, Biosciences, UK). Protein transfer was visualised by staining with Ponceau stain (Sigma, UK). The membrane was then subsequently incubated with primary antibody in blocking solution (PBS (Invitrogen, UK), 0.1% Tween (Sigma, UK), Skimmed milk (Merck, Germany)). Subsequently the membrane was then rinsed twice within Tween-PBS and once within PBS before being incubated in secondary antibody for 1.5 hours. The membrane was then was rinsed again, twice with Tween-PBS and once within PBS before the application of Immobilon reagent (Millipore, UK). Western blots were quantified using imageJ software (FIG. 6, 37, 38, 45).

Vector Neutralisation Assay

Female C57/BL6 mice (5-6 weeks old) were treated with one of;

PBS (control)
RALA alone
DNA alone (CMV/GFP)
RALA/DNA nanoparticles

Mice receiving DNA received 10 µg total. Nanoparticles were formulated with an N:P ratio of 10. Mice receiving RALA alone received an amount of vector equivalent to that received in the RALA/DNA group. Treatments were administered by tail vein injection performed over a three week period. There was 15 mice per treatment group, with 5 mice per time point. All animals received the relevant treatment on Day 0. Following 7 days, five mice from each group were sacrificed and blood from each will be isolated by cardiac puncture. Serum was isolated, serum from the five mice per group was pooled, heat-inactivated at 56° C. for 30-60 min, and serially diluted in Opti-MEM to produce serum concentrations of 10% v/v, 1% v/v and 0.1% v/v, plus a 0% control.

To these serum dilutions, fresh RALA/DNA nanoparticles (as above) were added at a DNA concentration of 1 µg/200 µl (the standard concentration for RALA/DNA transfection in 96 well plate format), and incubated at 37° C. for 1 h. This pre-incubated mix was then transferred to ZR-75-1 breast cancer cells previously seeded in 96 well plates (104 cells/ well) on Day 6, and transfection was performed in the usual manner. Transfection of the GFP construct was assessed by FACS analysis after 24 h.

On Day 7, the remaining 10 mice received a second administration of the appropriate treatment. On Day 14, five mice left the experiment and were treated as above, while the remaining five mice per group received a final administration of the appropriate treatment, and on Day 21, followed by the previously outlined treatment (FIG. 22, 23).

Enzyme-Linked Immunosorbent Assay

These assays were performed on the serum collected from immunocompetent C57/BL6 mice following either 1, 2, or 3 intravenous injection with the RALA/pEGFP-N1 nanoparticles. IgG, IgM, Il-12, IL-6, and TNF-β, ELISAs were performed using the ENZO ELISA Kits in accordance with the recommended protocol (FIG. 8).

For the neutralising antibody ELISA the following method applied;

Nunc Maxisorp ELISA plates were coated with RALA-pEGFP nanoparticles equivalent to 1 µg DNA per well. The wells were subsequently blocked with PBS/5% BSA. Wells were probed for 1 h with sera from mice diluted (1:500) in PBS/0.5% BSA at room temperature. (NB the sera came from the mice treated in the vector neutralisaiton assay). The wells were washed with PBS/0.5% Tween 20 and then probed for 30 min with HRP-conjugated anti-mouse secondary antibody. Wells were then washed again and probed with TMB substrate for 30 min. Colour development was measured at 450 nm with a reference wavelength of 550 nm (FIG. 24).

Confocal Microscopy

5000 ZR-75-1 breast cancer or PC-3 prostate cancer cells were grown on cover slips and transfected with Cy3 labelled RALA/pEGFP (lacks the promoter contained in the construct used in the neutralisation assay) or fluorescent siRNA. Confocal microscopy was used to determine subcellular localisation of RALA/Cy3-pEGFP nanoparticles (FIGS. 25, 44b & 58).

Gold Nanoparticle Experiment 5 nm phosphorylated gold nanoparticles were incubated with RALA peptide at a ratio of approximately 1:10 for 30 mins before being added to MDA-MB-231 breast cancer cells for 24 hours. The MDA-MB-231 cells (5000) had been seeded onto a coverslip. After 24 h the cells were fixed with 50% methanol and 50% acetone and sent to Cytoviva (Auburn, Ala.) for imaging (FIG. 26).

Greiss Test

Cells seeded in multiwell plates (6 or 24 well) were transfected with various amounts of pDNA (CMV/iNOS or hOC/iNOS) complexed with RALA at N:P 10 for 6 h, following which, transfection complexes were removed, and cells returned to normal growth medium (Minimum Essential Medium—MEM). After 48 h, 70 µl aliquots of conditioned MEM were assayed for their total nitrate (an indirect indicator of nitric oxide content) content using a Nitric Oxide Quantitation kit (Active Motif) following the manufacturer's instructions. A standard curve (using 0-35 µM sodium nitrate) was constructed and used to quantify nitrate content in sample wells of the assay plate. After incubation of standards and unknown samples with nitrate reductase and co-factors, Greiss reagents A and B were added to wells, and after a 20 min incubation to allow colour development, the absorbance of each well at 540 nm was determined (FIG. 38).

Clonogenic Assay

PC-3s grown in T25 tissue culture flasks were starved of serum by Opti-MEM incubation for 2 h before transfection with 10 µg of pDNA (CMV/iNOS, hOC/iNOS or CMV/GFP) for 6 h. Following transfection, media were replaced with MEM, and the cells incubated overnight. The next day, cells were trypsinised, resuspended in growth medium, enumerated, and plated in triplicate into 6 well plates (200 or 500 cells per well). Plates were incubated for 14 days to allow clonogenic growth, following which, medium was aspirated, colonies were stained with crystal violet and counted manually. Percentage cell survival was calculated by comparison with untransfected cells (FIG. 39).

Intracardiac Metastases Model

Female Balb/c SCID mice (5-8 weeks old) were inoculated via the left cardiac ventricle with 2×105 MDA-MB-231-luc2 breast cancer cells that express firefly luciferase. Mice then received an intraperitoneal injection of 200 µl D-luciferin (15 mg/ml) and were imaged (following 10 min) using IVIS imaging; successful left ventricular delivery was confirmed by whole body luminescence immediately following intracardiac delivery. Mice possessing luminescence limited to the thoracic cavity were sacrificed at this point. Remaining successfully inoculated mice were randomly assigned to one of four treatment groups (water, RALA only, RALA-CMV/iNOS or RALA-hOC/iNOS), and received five treatments twice weekly commencing two days post inoculation. Gene therapy mice received 10 µg pDNA complexed with RALA at N:P 10, RALA only mice received the corresponding amount of RALA dissolved with water; treatments were of 100 µl, and were delivered via the tail vein. Mice were routinely imaged twice weekly as described above, were observed daily by experienced animal husbandry experts, and body mass was monitored as an indicator of general health. A loss of 20% of original body mass was considered indicative of poor health of the mice, and this combined with a moribund appearance was determined to be a humane experimental end point (FIG. 40).

Effect of Runx2 Knockdown on Cell Proliferation

The effects of Runx2 knockdown on cell proliferation were evaluated at different time-points following transfection with RALA/Runx2 siRNA nanoparticles. Nanoparticles were prepared such that the final concentration of Runx2 siRNA was 100 nM and based on a N:P ratio of 12. Two Silencer Select Runx2 siRNAs were used and a Silencer Select non-coding siRNA (Invitrogen, UK). Cells were serum starved for 2 h prior to transfection. Transfections were carried out with both RALA peptide and Oligofectamine for a duration of 4 h in serum-free RPMI 1640 before RPMI 1640 containing 30% FCS was added to achieve a final FCS concentration of 10%. After 24, 48 and 72 h cells were detached using 2× trypsin and subsequently neutralised with RPMI 1640 containing 10% FCS. Cells were counted manually using a haemocytometer as described in 3.2.11.2 and the cell viability determined based on the assumption of a 100% viability of the untreated cells. Results are reported as mean±SEM, n=3, where n represents the number of independent batches prepared for analysis (FIG. 46).

Western Blotting for Runx2 Protein

To assess the ability of RALA/Runx2 siRNA nanoparticles to successfully inhibit Runx2 protein expression a range of siRNA concentrations and time-points following transfection were evaluated by Western blotting. PC-3 prostate cancer cells were seeded at a density of 150,000 cells per well in a 12-well plate. Transfections were initially carried out with various amounts of two types of Silencer Select Runx2 siRNA and Silencer Select non-targeting control siRNA such that the final siRNA concentration in the well was 50, 100 or 200 nM. Transfection was for 4 h followed by 48 h incubation. Following optimisation of the concentration the optimal time following transfection was determined using 100 nM concentrations. Cells were washed with ice-cold tris buffered saline (TBS) and lysed in a direct lysis buffer supplemented with MG-132 (Calbiochem, UK) and protease inhibitor cocktail (Roche, UK) (Appendix 1). Lysed samples were stored at −20° C. until required. Samples were run on 8% acrylamide gels at 100 V for 15 min followed by 150 V until the dye front reached the bottom of the gel in a tris-glycine running buffer. Subsequently the protein was transferred to PVDF membranes at 200 mA for 90 min in a tris-glycine transfer buffer. Membranes were blocked for up to 1 h in 2% blocking solution before leaving in primary antibody overnight at 4° C. with rocking. Runx2 primary antibody (MBL International, Woburn, Mass.) was used at a concentration of 1:200 and β-actin (Abcam, UK) at a concentration of 1:5000. Membranes were washed in TBS-tween (TBS-T) for 30 min before applying anti-mouse secondary antibody at 1:5000 for 1 h at room temperature. Membranes were washed vigorously in TBS-T for 30 min before developing. The chemiluminescent used for Runx2 protein was Thermo Scientific SuperSignal West Dura Chemiluminescent Substrate (Thermo Fisher Scientific, Waltham, Mass.) and for β-actin Thermo Scientific SuperSignal West Pico Chemiluminescent Substrate (Thermo Fisher Scientific, Waltham, Mass.) (FIG. 45).

Studies with the RAT Peptide

RAT was synthesised from a commercial company and is a fusogenic, consisting of RALA with an alphahelical concatemeric spacer, (EAAAK)4 (SEQ ID No. 18), and the TMTP1 (NVVRQ) (SEQ ID No. 12) metastatic prostate cancer targeting peptide (FIG. 54) (SEQ ID No. 14).

RALA-PEG5k

A pegylated version of RALA has been synthesised (FIG. 60).

Composite RALA Nanoparticles

RALA nanoparticles were prepared using desalted peptide in MOPS buffer at 50° C. to give a concentration of 50 µg/ml of DNA. PLGA and a series of PLA-PEG block copolymers were synthesized with various PEG chain length and LA/EG ratio (PLA10-PEG2; PLA25-PEG5; PLA50-PEG5) and formulated into composite nanoparticles (diameter <200 n m and PDI<0.2000) containing the RNPs. 100 µl of RALA nanoparticles was added to 0.5 ml 4% w/v copolymeric polymeric solution in dichloromethane under vortex and probe sonicated (120 Sonic Dismembrator with 3 mm probe, Fisher Scientific, USA) for 60 seconds at 50% of amplitude. This water-in-oil (w/o) emulsion was added to 2.5 ml of 5% w/v PVA solution in distilled water under vortex and probe sonicated as before in an ice bath for 2 minutes. The resultant emulsion was stirred overnight to form the composite nanoparticles. These were collected by centrifugation at 30,000 g for 30 min (3K30, Sigma Centrifuge, UK) and washed twice with distilled water, before suspending in 1 ml 5% w/v trehalose in water and were freeze-dried (Advantage, VirTis, Gardiner, N.Y., USA). TEM (JEOL JEM1400 transmission electron microscope at an accelerating voltage of 80 kV) was performed by loading samples onto a copper grid (Formvar/Carbon 200 mesh, Agar scientific). Osmium tetraoxide was incorporated by adding it to the organic phase during preparation of the composite nanoparticles.

Results

Particle Characterisation.

As shown in FIG. 2, RALA condensed siRNA to form discrete spherical nanoparticles formed at N:P 12. RALA also condensed DNA at N:P 10 and bisphosphonates giving spherical particles (FIG. 28, 50). This indicates that the RALA is condensing the nucleic acid in a uniform manner. Whether siRNA, DNA or bisphosphonates, the overall positive charge also ensures that the particles are discrete and repel each other which avoids aggregation and ensures a homogenous population.

Particle formation between DNA and RALA was studied by gel retardation assays and dynamic light scattering. It was found that RALA fully condensed DNA at N:P ratios above 4 (FIG. 27). Dynamic light scattering revealed that particle sizes were below 100 nm at N:P ratios above 4 and around 1 µm at N:P 2 and 3 (FIGS. 3,9, 17 to 21, 42). The zeta potential of the particles at N:P ratios 2 and 3 was −15 mV and −5 mV respectively. The zeta potential was only positive at N:P ratios greater than 4. A near-zero zeta potential also means that there is little surface repulsion between particles and as a result the large aggregates are observed which is reflected in the size of the nanoparticles at N:P ratios 2 and 3. Above N:P 4, on the other hand, particles have a diameter below 100 nm and as a result may theoretically enter cells via endocytosis. The RALA/pEGFP-N1 nanoparticles at a ratio of N:P 10 were dried and stained with 5% uranyl acetate and transmission electron microscopy at 80 kV further confirmed the presence of spherical particles in the region of 100 nm in diameter (FIG. 27). From N:P 3 upwards the encapsulation efficiency of the RALA/pEGFP-N1 nanoparticles was greater that 90% (FIG. 53).

Additionally, serum stability of particles at N:Ps of 5, 10 and 15 showed that the nanoparticles are stable in the presence of 10% serum and dissociate in 1% SDS revealing that the integrity of the DNA remains intact (FIGS. 5, 7a, 10 & 30). As the nanoparticles were found to be stable for up to 6 (FIG. 30, 33). Nanoparticles were also stable in range of temperatures 4-37° C. (FIG. 29, 42).

In Vitro Transfection Efficacy & Cytotoxicity.

ZR-75-1 cells were transfected with RALA/pEGFP-N1 nanoparticles. Epi-fluorescence microscopy showed a high transfection efficacy of ZR-75-1 cells, when transfected with RALA/pEGFP at N:P of 10 with and without chloroquine. Chloroquine is a known endosomal disrupter and will increase transfection if the nanoparticles are inefficient endosome disrupters. At N:P 10 this is clearly not the case. Flow cytometry was then used to further analyse the effect of N:P on transfection efficacy and revealed an optimal transfection efficacy of around 30% between N:P ratios 8-12. More importantly though the WST-1 cell viability assay revealed minimal toxicity of the nanoparticles over a range of N:P ratios. Cell viability was 90% for N:P 4 and 80% at N:P 10. Indeed when cellular proliferation was examined there was significant difference between lipofectamine 2000 and RALA/pEGFP-N1 transfected cells (FIG. 34). Similar effects were also observed for PC-3 cells in respect of transfection and also cell viability (FIG. 35, 36). In addition transfection with RALA peptide derivative 2-6 showed transfection efficiencies of at least 40% (FIGS. 17 to 21, 31). Percentage transfection with these nanoparticles in the absence and presence of bafilomycin (FIG. 32) showed a significant reduction at all N:P ratios investigated (p=0.0037, 0.0002 and 0.0021 respectively for N:P ratios 8, 10 and 12 with RALA/pEGFP-N1 using an unpaired one-tailed t-test), indicating the acidic pH is essential for nanoparticle release from the endosome.

To determine if RALA/pEGFP-N1 nanoparticles are significantly more efficient at eliciting cellular transfection in comparison to KALA/pEGFP-N1 nanoparticles a transfection experiment with both peptide-based nanoparticles was carried out in parallel (FIG. 33). It is possible to see that percentage transfection achieved with RALA/pEGFP-N1 nanoparticles N:P ratio 8 and 10 is significantly higher than those achieved with the KALA/pEGFP-N1 nanoparticles (p=0.0002 and 0.0048 using a one-tailed unpaired t-test). The RALA/pEGFP-N1 nanoparticles were more efficient than the commercially available happyfect (FIG. 37).

Confocal microscopy also confirmed successful transfection with a time course revealing diffuse pattern of distribution of nanoparticles that focus into distinct foci with increasing duration of transfection (FIG. 25). Internalisation of RALA/DNA nanoparticles has been demonstrated. There was also increased internalisation and disruption of the endosomes when RALA was used to deliver gold nanoparticles (FIG. 26). When fluorescent siRNA was delivered it could also be seen that it was internalized into the cytosol and indeed proved more efficacious than the commercially available oligofectamine (FIG. 44).

Lyophylisation of RALA.

As RALA/pEGFP-N1 nanoparticles transfect cells efficiently and are non-toxic, it was decided to use these nanoparticles as a model of a potentially therapeutic peptide based polyplex. It is well know that a major problem with gene therapy protocols is storage as both peptide and DNA degrade if stored in aqueous solutions at room temperature for prolonged periods of time. As such, the nanoparticles were lyophylised with a range of concentrations of trehalose as a lyoprotectant. Transfections, as well as serum stability assays were performed before and after freeze-drying. Serum stability assays were performed on all formulations up to 6 h. All formulations were found to be as stable upon incubation with 10% serum as the fresh particles without trehalose (FIG. 7a). In addition, decomplexation with 1%

SDS disrupted the nanoparticles in all cases and revealed no significant DNA damage in the reconstituted samples (FIG. 7a). It was also found that the RALA based polyplexes are equally efficient at transfecting cells both before and after lyophilisation (FIG. 7b). Increasing the concentration of trehalose did not improve transfection, but rather seemed to decrease transfection efficiency at high concentrations although there was no significant difference between fresh and freeze-dried nanoparticles. It was also found that those nanoparticles without trehalose still retained activity post freeze-drying (FIG. 7b). Although the freeze dried particles in this formulation tended to stick to the glass vials and needed more time to resuspend.

Overall these results highlight the stability of RALA/pEGFP-N1 nanoparticles as well as the ease with which dried formulations can be stored, even without lyoprotection. These data indicate that the RALA could be lyophilised, stored and reconstituted prior to administration without losing activity.

Transfection Efficacy & Immunogenicity of RALA in vivo.

As RALA has proven highly effective in vitro, the next logical step would be to test its transfection efficacy and distribution and most importantly, bio-compatibility in vivo. As such, ZR-75-1 tumour bearing BALB/C-SCID mice were injected intravenously with 50 µl of N:P 10 RALA/pEGFP-N1 or RALA/phOCMetLuc nanoparticles carrying a total of 10 µg of plasmid DNA per dose. Western blots showed transfection in all organs with the pEGFP-N1 carrying nanoparticles and in the tumour, surrounding tissue and liver with phOCMetLuc nanoparticles (FIG. 6). Immunoperoxidase staining of organs sections revealed low levels of transfection in the tumour, liver, lungs and kidney, with transfection being undetectable in heart and peritumoral tissue for the RALA/pEGFP-N1 treated animals (FIG. 6).

In order to determine whether the RALA based nanoparticles would be safe for repeated administration, immunocompetent C57/BL6 mice were treated once a week with either 50 µl of PBS, PEI, RALA, pEGFP-N1, PEI/pEGFP-N1 or RALA/pEGFP-N1 for 3 weeks. In each instance the dose of plasmid DNA delivered was 10 µg. Blood was collected via cardiac puncture and ELISA's were performed for IgGs, IgMs, TNFα, IL6 and IL1β, alongside a Greiss test for increased nitric oxide concentrations. No morbidity or visible immune response was seen upon inspection of the live animals. ELISAs for interleukins yielded no statistically significant differences between groups of treatments (FIG. 8) Concentrations of nitrates were found to be elevated in the third week compared to previous weeks ($p<0.01$), but no significant differences were seen between treatments (FIG. 8). The change in TNFα concentrations with repeated treatments were found to be highly statistically significant, with higher concentrations in the first week, and lower concentrations following subsequent treatments, this was especially prominent in the PBS only and PEI only treatment groups ($p<0.05$ and $p<0.01$ respectively). In addition, the RALA only treated mice had a significantly lower initial response of TNFα than the PEI only treated animals ($p<0.05$) (FIG. 8). Concentrations of IgM were found to be significantly lower with repeated administration ($p<0.001$). This effect was more pronounced in the PBS only treatment group ($p<0.05$). Changes in IgG concentrations depended heavily on both the treatment group and the treatment applied ($p<0.01$). Naked DNA induced a strong IgG response on the third week ($p<0.05$), which was significantly higher than that induced by RALA only, RALA/pEGFP-N1, PEI/pEGFP-N1 and PBS only ($p<0.05$, $p<0.01$, $p<0.05$, and $p<0.01$ respectively), indicating that naked DNA induces an adaptive immune response, while neither the RALA or PEI based nanoparticles cause this kind of response (FIG. 8). This in turn indicates that RALA and PEI shield the plasmid DNA from detection by the immune system This data set clearly indicates that systemic delivery of RALA/pEGFP-N1 nanoparticles does not induce a significant immune response either innate or adaptive even after multiple injections.

Furthermore multiple injections of the RALA nanoparticles did not evoke neutralising antibodies that would prevent RALA from delivering its payload. FACS analysis of PC3 and ZR-75-1 cells indicated that transfection of both cell types was hampered by the presence of 10% serum, but this occurred with the FBS controls as well eliminating the activation of an immune response (FIGS. 22 and 23). This was further confirmed by the ELISA on the sera samples which showed that there was there was no significant difference in immunoreactivity between the different treatment groups (FIG. 25).

Systemic Delivery of RALA/iNOS Nanoparticles

Transfection of PC-3 and MDA-MB-231 with plasmid iNOS constructs complexed with RALA evoked nitric oxide production (as determined by total nitrate content of growth media—an indirect method of nitric oxide quantification). PC-3s and MDA MB-231s transfected with the inducible hOC/iNOS plasmid produced significantly more nitrates than were present in control ($P=0.038$ and $0.048$ respectively), and those transfected with the constitutively active CMV/iNOS also produced levels of nitrates considerably higher than seen in control. Nitrate content of media of cells transfected with green fluorescent protein constructs under the control of the same promoters were consistent with control (FIG. 38).

Transfection of PC-3s with hOC/iNOS complexed with RALA prior to clonogenic assay resulted in significantly lower clonogenic survival compared to control ($P=0.004$). Transfection of the same cells with CMV/iNOS resulted in a roughly similar loss of clonogenic survival ($0.69\pm0.08$ vs $0.61\pm0.03$), while transfection with CMV/GFP did not affect clonogenic survival of PC-3s (surviving fraction of $1.01\pm0.11$) (FIG. 39). This experiment has been performed twice; it is likely that a third replicate will resolve the significance of CMV/iNOS treatment, and further support that of hOC/iNOS.

Metastatic deposits were established in female BALB/c SCID mice by inoculation with $2\times10^5$ MDA-MB-231-D3H1 that express luciferase via the left ventricle of the heart. Metastatic development was monitored routinely by IVIS imaging of bioluminescence (FIG. 40). Control treatment for these mice was water (the vehicle for gene therapy treatments); mice receiving water treatment had a median survival of 30 days post inoculation. The median survival for mice receiving RALA only treatment was also 30 days ($P=0.76$ compared with water control). Treatment with hOC/iNOS or CMV/iNOS complexed with RALA resulted in a significant improvement of post inoculation survival, with mice receiving hOC/iNOS having a median survival of 40 days ($P=0.001$ compared with water), and those that received CMV/iNOS having a median survival of 42 days ($P=0.004$).

Delivery of RALA/siRUNX2 as a Therapeutic

To confirm that Runx2 protein expression could successfully be knocked down using the RALA, PC-3 prostate cancer cells were transfected and the cell lysate collected for Western blotting. Two types of Runx2 siRNA were used as well as a non-targeting scrambled siRNA. Furthermore, Oligofectamine was used as a positive control for comparison. Initially the concentration of siRNA required to achieve knockdown was assessed followed by the optimal incubation time post-transfection. Densitometry of the Western blots using Image J software enabled the degree of knockdown of protein expression to be quantified by assuming the scrambled control siRNA results in 0% knockdown.

FIG. 45 shows the optimisation of the time required following transfection to achieve optimal knockdown of Runx2 protein expression. This was assessed using a siRNA concentration of 100 nM as determined previously. It can be seen clearly that there is substantial knockdown of protein expression at each timepoint. There was no increase in knockdown with increasing time as confirmed by one-tailed unpaired t tests which found no significance between the knockdown at each timepoint as well as no difference in knockdown between each of the delivery systems ($p>0.05$). As such it can be confirmed that 24 h is sufficient time to detect optimal knockdown. Furthermore, there is no significant difference in the effectiveness of each of the two Runx2 siRNAs across any of the concentrations or timepoints with both of the transfection reagents used ($p>0.05$) as determined by one-tailed unpaired t test.

RALA peptide was able to achieve comparable levels of knockdown to the commercial RNA transfection reagent, Oligofectamine. Analysis of the transfection profile of RALA and Oligofectamine using fluorescent siRNA showed a peak in transfection immediately after transfection with RALA but it took 24 h to reach a peak with Oligofectamine.

To determine the effects of Runx2 knockdown on prostate cancer cell proliferation, PC-3 prostate cancer cells were transfected with 100 nM Runx2_1, Runx2_2 or non-targeting scrambled siRNA using RALA or Oligofectamine as a positive control. Where RALA was used nanoparticles were prepared at N:P 12 and Oligofectamine was used as per the manufacturer's guidelines. Cells were trypsinised and counted using a haemocytometer at 24, 48 and 72 h following the 4 h transfection. Untreated cells were assumed to have 100% viability and the percentage viability for all other treatments was based on this.

Cell viability was significantly lower with Runx2_1 compared to Runx2_2 24 h following transfection with RALA peptide ($p=0.0376$). However, no significant difference between the two siRNAs is seen at any other timepoint or following delivery using Oligofectamine ($p>0.05$) as determined by two-way ANOVA. Furthermore, there is no significant difference in cell viability following transfection of Runx2_1 and Runx2_2 across the timepoints studied up to 72 h ($p>0.05$) when determined by two-way ANOVA. RALA/Runx2_1 siRNA nanoparticles resulted in a significant reduction in cell viability when compared to RALA/scrambled siRNA nanoparticles at each of the 24, 48 and 72 h timepoints evaluated ($p<0.001$, 0.05 and 0.01 respectively). Similar results were found with RALA/Runx2 siRNA nanoparticles ($p<0.01$, 0.01 and 0.001 respectively). These results were consistent with the positive control, Oligofectamine, which also resulted in a significant decrease in cell viability compared to the scrambled control with Runx2_1 ($p<0.001$, 0.01 and 0.001 at 24, 48 and 72 h respectively) and Runx2_2 ($p<0.01$, 0.05 and 0.01 at 24, 48 and 72 h respectively). Overall, knockdown of Runx2 protein expression results in a reduction in cell viability of approximately 30% over 72 h (FIG. 46).

Tumours were grown on the rear dorsum of BALB-C SCID mice until the volume reached approximately 150 mm3 before intratumoural treatment with either RALA/Runx2 siRNA nanoparticles, Runx2 siRNA only or RALA/scrambled siRNA nanoparticles commenced. Runx2_1 and Runx2_2 siRNA were pooled for the purposes of in vivo analysis as neither was found to be significantly better in achieving Runx2 knockdown. Dosing was once weekly until tumour quadrupling defined the endpoint of the experiment. Control tumours grew rapidly with all tumours quadrupling in volume within 16 days of the start of treatment (average 15 days). RALA/scrambled siRNA nanoparticle treatment mice follow a similar rate of growth as the untreated. The rate of growth is also similar for Runx2 siRNA treated mice until after the second treatment; following this the tumours grow at a slower rate than the untreated and RALA/scrambled siRNA groups. In mice treated with RALA/Runx2 siRNA nanoparticles, tumours grow at a slower rate than all other groups until the point of tumour volume quadrupling (FIG. 47a). It appears that the difference in survival time between the untreated mice compared to those receiving RALA/scrambled siRNA nanoparticles is small; however, it is not possible to determine the significance of this difference due to the small group numbers. Mice treated with Runx2 siRNA had a higher survival time of 22.5 days compared to 15 days for untreated mice (FIG. 47b). The Kaplan-Meier plot required no censoring of the data as no animals were euthanised or died apart from those in which the tumour volume quadrupled (experimental end-point). A significant increase in survival time of RALA/Runx2 siRNA nanoparticle treated mice of 80% was seen when compared to the untreated control group ($p=0.0002$) (FIG. 47c)

Delivery of RALA/BP as a Therapeutic

Figure 51A:
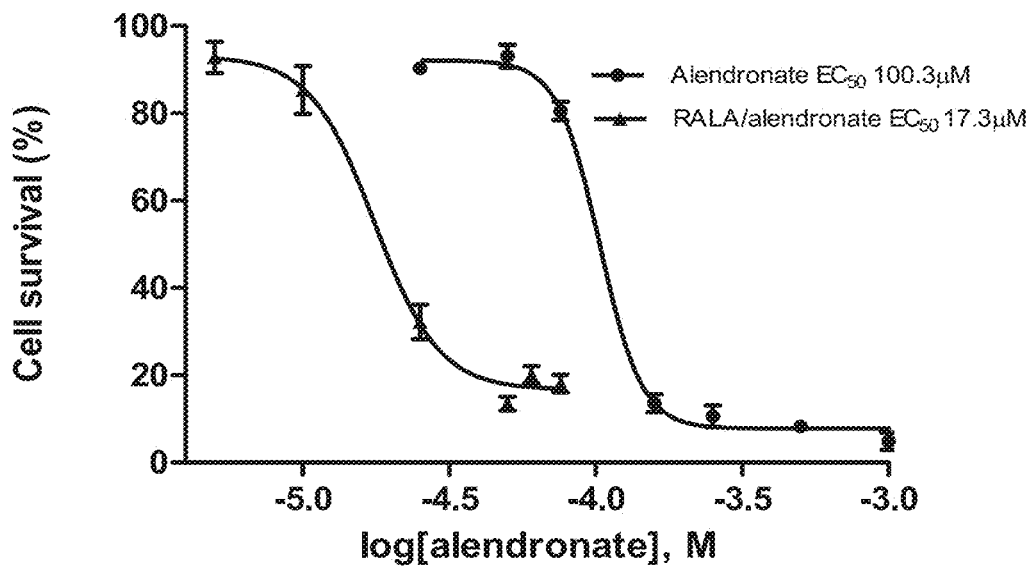
Figure 51B:
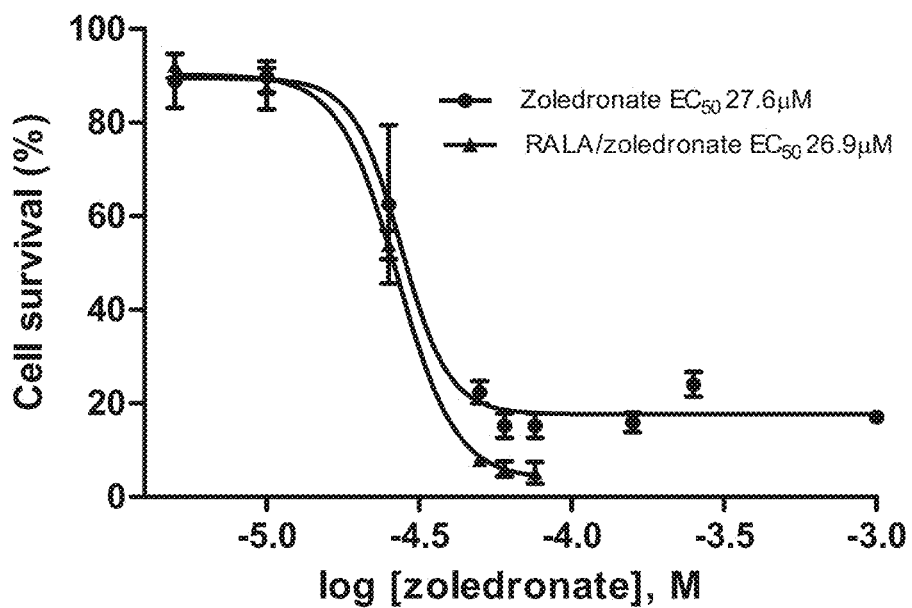
Figure 51C:
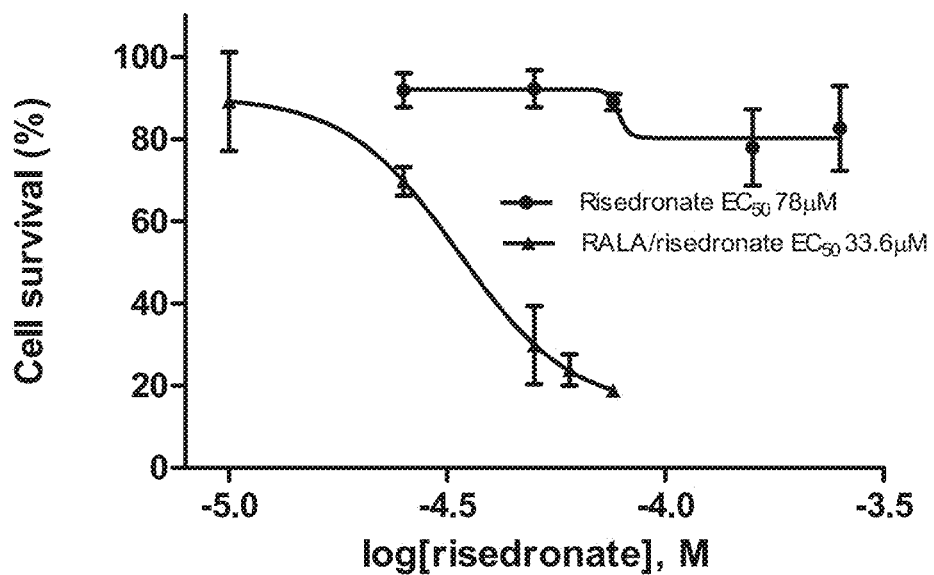
Figure 51D:
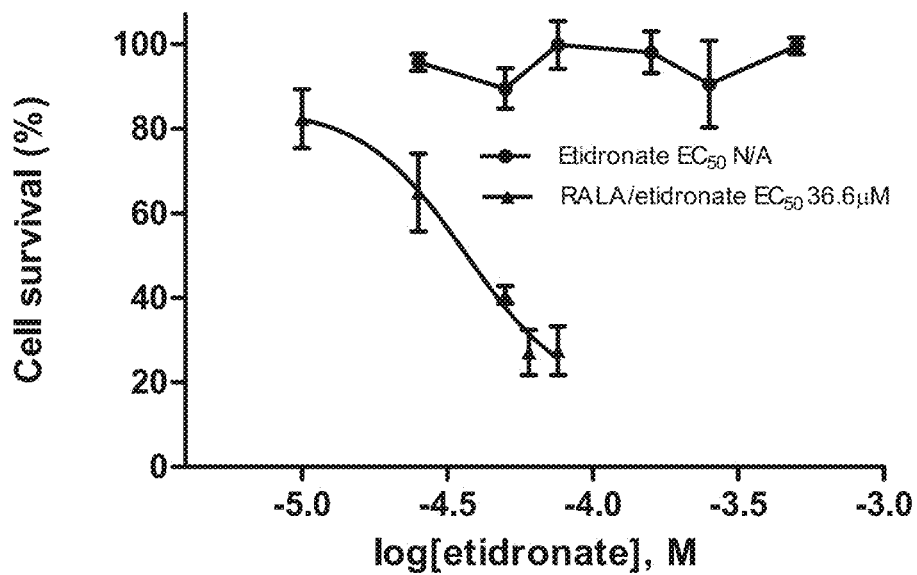

In order to assess the effectiveness of RALA as a delivery agent for optimisation of the antitumour effects of BPs, PC-3 prostate cancer cells were either treated with free BP or transfected with RALA/BP nanoparticles at a range of concentrations for 6 h and then incubated for 72 h before evaluating cell viability. Cell viability was analysed by cell counting using a haemocytometer. EC50 values were determined using the dose-response curves generated from this cell viability data. The EC50 of alendronate was reduced from 100.3 µM to 17.6 µM when delivered in a RALA nanoparticle, a potentiation factor of 5.7 (FIG. 51a). The EC50 of zoledronate was reduced from 27.6 µM to 26.9 µM when delivered in RALA nanoparticles as determined by the dose-response curve. However, the maximum cell kill that could be achieved with zoledronate only was 82% compared to the 96% seen with RALA/zoledronate nanoparticles (FIG. 51b). The EC50 of risedronate was determined from the dose-response curve to be 78 µM. However, this concentration equated to the concentration required to see a 10% cell kill as the maximum cell kill observed when cells were treated with risedronate was 20%. Transfection of the cells with RALA/risedronate nanoparticles, however, saw a maximal cell kill of 86% with an EC50 of 33.6 µM (FIG. 51c). It was not possible to determine an EC50 value for etidronate using the dose-response curve as there was no reduction in percentage cell survival with increasing BP. However, when etidronate is delivered in RALA/etidronate nanoparticles a reduction in cell survival can be seen and the EC50 of RALA/etidronate nanoparticles was determined from the dose-response curve to be 36.6 µM (FIG. 51d).

Tumours were grown on the rear dorsum of BALB-C SCID mice until the volume reached approximately 100 mm3 before intratumoural treatment with RALA/alendronate, alendronate or RALA commenced. Dosing was thrice weekly until tumour quadrupling defined the endpoint of the experiment. It can be seen clearly that RALA only had no significant effect on tumour growth ($p=0.0792$) while alendronate and RALA/alendronate show high statistical significance when compared to the untreated control ($p<0.0001$ and p=0.0004 respectively) (FIG. 52a). Furthermore, the difference in time taken for tumour volume to quadruple is also significantly different between alendronate and RALA/alendronate (p=0.0019) (FIG. 52b). Control tumours grew rapidly with all tumours quadrupling in volume within 16 days of the start of treatment. This is consistent with previous results from the group on the PC-3 tumour model. Treatment with alendronate and RALA/alendronate slows tumour growth at an almost identical rate up to treatment 4. However, beyond treatment 4 the rate of growth in alendronate treated tumours changes with tumour volume beginning to increase more rapidly. RALA/alendronate tumours continue to grow at a similar rate to the beginning of treatment up to the end of the treatment course (3 times weekly dosing for 3 weeks) but then began to grow more rapidly after discontinuation of therapy. However, the rate of growth upon discontinuation of treatment is still lower than the controls and the higher rate of growth in alendronate treated mice (FIG. 52). The Kaplan-Meier plot required no censoring of the data as no animals were euthanised or died apart from those in which the tumour volume quadrupled (experimental end-point). A significant increase in survival time of RALA/alendronate nanoparticle treated mice of 56.3% was seen when compared to the untreated control group (p<0.001). The survival time of this group was also significantly higher compared to the alendronate only treated group at 32% (p<0.01) (FIG. 52c).

RAT Results

RAT was synthesized (FIG. 54) and was able to complex pEGFP-N1 into nano-sized particles. Zetasizer analysis coupled with dynamic light scattering software analysis was performed to analyse the size, charge, particle count and polydispersity index of the RAT/pEGFP-N1 nanoparticles (FIG. 55). Through N:P ratios 1 to 4 the zeta potential increases from −17.9 mV±3.60 to 19.13 mV±3.75 and at N:P12 the nanoparticles were 71.03 nm±11.36 with a zeta potential of 17.49 mV±11.92. Taken together it is likely that N:P ratios of 4 to 12 have characteristics suitable for transfection.

A serum incubation study was used to determine if RAT/pEGFP-N1 nanoparticles were stable over a 6 h time period with and without the presence of foetal calf serum (FIG. 56). DNA migration was not observed with N:P12 nanoparticles on a 1% agarose gel when incubated for up to 6 h at 37° C.; supporting the gel retardation assay which demonstrated that DNA is neutralised by RAT from N:P3 upward. Decomplexation of the nanoparticles occurred in the presence of 10% sodium dodecyl sulphate enabling the integrity of the DNA to be assessed. In the presence of 10% serum, over a 6 h period, nanoparticles have not been disrupted as they remained within the wells of the agarose gel. The serum remains visible in all lanes indicating no aggregation with the positively charged nanoparticles. Analysis of DNA cargo, using 10% SDS to disrupt the nanoparticles, reveals that DNA integrity was not affected by serum endonucleases and protection was afforded by RAT.

The specificity of the RAT peptide was assessed using a targeting inhibition study (FIG. 57). Free targeting peptide, TMTP-1, was added at a range of concentrations prior to transfection as a competitive inhibitor of RAT/pEGFP-N1 nanoparticles and results were compared with the untargeted RALA peptide. The results show that as the concentration of competitive inhibitor increased transfection efficacy with RAT decreased. Conversely the inhibitor had no significant effect upon transfections with RALA. For example when 0.25 nM, 1.5 nM and 2 nM of inhibitor was placed upon PC-3 cells, gene expression with RAT/pEGFP-N1 was significantly reduced by 19.16%±8.00, 48%±17.00 and 57.26%±16.01 respectively (P<0.1). This indicates that the RAT nanoparticles are internalising via the TMTP-1 receptor thus conferring a degree of specificity.

TEM also confirmed the presence of the RALA nanoparticles inside the composite nanoparticles (FIG. 59). An in vitro DNA release study also demonstrated that the composite nanoparticles were able to release DNA, with 10% DNA content released in 24 hours and continuous release over 6 weeks.

In summary, the results presented show that RALA is efficient, stable, safe and a viable delivery vehicle for iNOS DNA, RUNX2 siRNA and bisphosphonate anti-cancer therapeutics.

Conclusion

The physical properties of the RALA/pEGFP-N1 nanoparticles have been analysed and their efficacy as a transfection agent demonstrated both in vitro and in vivo. RALA was found to form stable complexes with pEGFP-N1 and facilitate the transfection of ZR-75-1 cells. Gel retardations show that complexes are formed at N:P ratios as low N:P 1, but full complexation is not seen until N:P 4, which is comparable with KALA and ppTG peptides [Rittner et al. 2002]. The RALA/pEGFP-N1 complexes cannot be defined as nanoparticles until N:P 4, as their size at N:P ratios 2 and 3 was in the micrometer range. At ratios of N:P 4 and above, RALA forms nanoparticles with pEGFP-N1 with a positive charge of 30 mV. This is in agreement with the counter-ion condensation theory, which states that particle sizes of charged complexes should be lower than those of uncharged particles, as electrostatic repulsion should prevent aggregation [de Smedt et al. 2000, Bagwe et al. 2006].

Given that at the N:P ratios which yield the highest transfection efficacy, the particles have a positive surface charge and a mean diameter below 100 nm, it is possible that they bind to the negatively charged cell surface proteoglycans non-specifically and are subsequently taken up into the endosomes.

With respect to transfection efficiency, the use of arginine in the RALA peptide has two distinct advantages; firstly arginine has consistently been shown to be the optimal amino acid for condensing DNA with arginine rich sequences binding in milliseconds (Murray et al 2001). Secondly arginine rich sequences based on the Rev sequence have the capacity to actively transport DNA into the nucleus of cells via the importin pathway (Malim et al 1989). This gives RALA a distinct advantage over conventional peptide delivery systems.

We have also shown that the RALA/pEGFP-N1 nanoparticles are not strongly cytotoxic, causing only a 20% reduction in cell viability in transfected cell monolayers. Perhaps the most important result is the confirmation of in vivo activity of the nanoparticles following systemic administration. High levels of delivery to the lungs were seen when a plasmid expressing luciferase was delivered to mice using the ppTG-1 peptide, but the liver was not examined [Rittner et al. 2002]. When fluorescently labelled siRNA was delivered with the MPG-8 peptide, it was observed in the majority of organs with high levels in the lungs and liver [Crombez et al. 2009]. No morbidity or mortality of animals was observed following treatment in the experiments described in this work, although this has not always been the case with peptide based gene delivery agents (Rittner et al. (2002) reported the death of several mice when delivering the plasmid systemically with the ppTG1 peptide.

In addition, RALA does not appear to cause a significant immune response upon repeated administration beyond the inflammation associated with tissue damage caused by the needle at the site of injection. There is also no neutralization of RALA following repeated administration. Furthermore, RALA appears to shield naked DNA from generating an adaptive immune response and does not cause an antibody response on its own. This is an encouraging result given that peptides are often used as vaccines because they share homology with viral and tumour proteins and produce a high antigenic response [Yang et al. 2009, Rodriguez and Grubman 2009]. As such, it might be expected that RALA, a peptide that is analogous to viral fusion proteins, might likewise be highly immunogenic. It appears, that as RALA uses a simple highly repetitive, artificially designed sequence that is not common in nature, its immunogenicity is low.

Part of the effectiveness of RALA as a transfection agent is probably related to its ability to protect DNA or siRNA from a hostile environments. The complexation of RALA to plasmid DNA forms nanoparticles that protect DNA from, freeze-drying and degradation in serum. While the ability to protect the cargo from degradation by serum has a bearing on transfection efficacy, the ability to act as a lyoprotectant has implications for further formulation related issues that surround transfection agents. The logistics behind supplying gene medicine to clinics are complicated by the lack of stability of most prospective vectors. Since viral vectors are notoriously difficult to store and non-viral vectors usually require lyoprotectants, which alter the final formulation, before they can be successfully freeze-dried, it is promising to see that RALA/pEGFP-N1 nanoparticles retain activity following reconstitution after lyophilisation.

RALA has also been shown to successfully condense and form nanoparticles with a range of bisphosphonates, siRNA and is an excellent tool for local delivery. It has also been used for the systemic delivery of the iNOS therapeutic to metastatic deposits of cancer with an excellent response. This indicates a wide range of applications for this peptide delivery system.

Example 3

Alternative Peptide Sequences

The following peptide sequences based on RALA (WEARLARALARALARHLARALARALRACEA) (SEQ ID No. 1) were also prepared using conventional commercial techniques as expanded on in Example 1.

TABLE 3

Key Characteristics RALA (WEARLARALARALARHLARALARARACEA) (SEQ ID No. 1) derivative Peptides in ZR-75-1 breast cancer cells determined in accordance with the protocols of Example 2.

| Peptide N:P10 | SEQ ID No. | Characteristics Length Hydrophilic:Hydrophobic +/− | Best Size (nm) | Charge (mV) | Transfection Efficiency in ZR-75-1 Cells |
|---|---|---|---|---|---|
| 1. Original RALA | 1 | 30 mer 30:67:1 8:2 | 70 | 25 | 30% |
| 2. Peptide 2 (H Removed) | 2 | 29 mer 31:70 7:2 | 76 | 22 | 55 |
| 3. Peptide 3 (H Replaced with E) | 4 | 30 mer 33:67 7:3 | 51 | 24 | 41 |
| 4. Peptide 4 (H Removed and Replaced W replaced with R) | 5 | 29 mer 33:67 8:2 | 37 | 12 | 50 |
| 5. Peptide 5 (H Removed and W replaced with R and C replaced with R) | 6 | 29 mer 37:63 9:2 | 53 | 13 | 46 |
| 6. Peptide 6 (H Replaced with E and W replaced with R and C replaced with R) | 7 | 30 mer 40:60 9:3 | 308 | 6 | 43 |

Results

The results in terms of transfection efficiency in ZR-75-1 cells are shown in Table 3. Peptides 1-5 successfully condensed the DNA into nanoparticles less than 100 nm. The exception being peptide 6, where the smallest nanoparticle measured was 308 nm. It can also be deduced that the highest transfection efficiency was with peptide 2 at 55% and as the hydrophilic ratios increase up to 40% the surface charge of the nanoparticle decreases. Furthermore the addition of glutamic residues reduces transfection efficiency as evidenced by peptide 3 and peptide 6. Nevertheless all sequences have potential as delivery vehicles for nucleic acids and hydrophilic compounds.

A 22mer WEARLARALARALARHLRACEA (SEQ ID No. 8) was also tested but was unable to condense DNA into nanoparticles and transect cells and was therefor deemed unsuccessful.

REFERENCES

Rittner K, Benavente A, Bornpard-Sorlet A, Heitz F, Divita G, Brasseur R, Jacobs E. New basic membrane-destabilizing peptides for plasmid-based gene delivery in vitro and in vivo. Mol Ther. 2002 February; 5(2):104-14.

De Smedt S C, Demeester J, Hennink W E. Cationic polymer based gene delivery systems. Pharm Res. 2000 February; 17(2):113-26.

Bagwe R P, Hilliard L R, Tan W. Surface modification of silica nanoparticles to reduce aggregation and nonspecific binding. Langmuir. 2006 Apr. 25; 22(9):4357-62.

Murray K D, Etheridge C J, Shah S I, Matthews D A, Russell W, Gurling H M, Miller A D. Enhanced cationic liposome-mediated transfection using the DNA-binding peptide mu (mu) from the adenovirus core. Gene Ther. 2001 March; 8(6):453-60.

Malim M H, Hauber J, Le S Y, Maizel J V, Cullen B R. The HIV-1 rev trans-activator acts through a structured target sequence to activate nuclear export of unspliced viral mRNA. Nature. 1989 Mar. 16; 338(6212):254-7.

Crombez L, Morris M C, Dufort S, Aldrian-Herrada G, Nguyen Q, Mc Master G, Coll J L, Heitz F, Divita G. Targeting cyclin B1 through peptide-based delivery of siRNA prevents tumour growth. Nucleic Acids Res. 2009 August; 37(14):4559-69.

Yang T, Wang H N, Wang X, Tang J N, Lu D, Zhang Y F, Guo Z C, Li Y L, Gao R, Kang R M. The protective immune response against infectious bronchitis virus induced by multi-epitope based peptide vaccines. Biosci Biotechnol Biochem. 2009 July; 73(7):1500-4.

Rodriguez L L, Grubman M J. Foot and mouth disease virus vaccines. Vaccine. 2009 Nov. 5;

```
<400> SEQUENCE: 4

Trp Glu Ala Arg Leu Ala Arg Ala Leu Ala Arg Ala Leu Ala Arg Glu
1               5                   10                  15
Leu Ala Arg Ala Leu Ala Arg Ala Leu Arg Ala Cys Glu Ala
            20                  25                  30

<210> SEQ ID NO 5
<211> LENGTH: 29
<212> TYPE: PRT
<213> ORGANISM: Artificial Sequence
<220> FEATURE:
<223> OTHER INFORMATION: amphipathic peptide sequence (Table 2)

<400> SEQUENCE: 5

Arg Glu Ala Arg Leu Ala Arg Ala Leu Ala Arg Ala Leu Ala Arg Leu
1               5                   10                  15
Ala Arg Ala Leu Ala Arg Ala Leu Arg Ala Cys Glu Ala
            20                  25

<210> SEQ ID NO 6
<211> LENGTH: 29
<212> TYPE: PRT
<213> ORGANISM: Artificial Sequence
<220> FEATURE:
<223> OTHER INFORMATION: amphipathic peptide sequence (Table 2)

<400> SEQUENCE: 6

Arg Glu Ala Arg Leu Ala Arg Ala Leu Ala Arg Ala Leu Ala Arg Leu
1               5                   10                  15
Ala Arg Ala Leu Ala Arg Ala Leu Arg Ala Arg Glu Ala
            20                  25

<210> SEQ ID NO 7
<211> LENGTH: 30
<212> TYPE: PRT
<213> ORGANISM: Artificial Sequence
<220> FEATURE:
<223> OTHER INFORMATION: amphipathic peptide sequence (Table 2)

<400> SEQUENCE: 7

Arg Glu Ala Arg Leu Ala Arg Ala Leu Ala Arg Ala Leu Ala Arg Glu
1               5                   10                  15
Leu Ala Arg Ala Leu Ala Arg Ala Leu Arg Ala Arg Glu Ala
            20                  25                  30

<210> SEQ ID NO 8
<211> LENGTH: 22
<212> TYPE: PRT
<213> ORGANISM: Artificial Sequence
<220> FEATURE:
<223> OTHER INFORMATION: 22mer protein sequence (Table 2)

<400> SEQUENCE: 8

Trp Glu Ala Arg Leu Ala Arg Ala Leu Ala Arg Ala Leu Ala Arg His
1               5                   10                  15
Leu Arg Ala Cys Glu Ala
            20

<210> SEQ ID NO 9
<211> LENGTH: 30
<212> TYPE: PRT
<213> ORGANISM: Artificial Sequence
<220> FEATURE:
```

<223> OTHER INFORMATION: prior art GALA sequence (anionic)

<400> SEQUENCE: 9

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: prior art KALA sequence (cationic)

<400> SEQUENCE: 10

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 11
<211> LENGTH: 16
<212> TYPE: PRT
<213> ORGANISM: Artificial Sequence
<220> FEATURE:
<223> OTHER INFORMATION: prior art RALA 16mer sequence

<400> SEQUENCE: 11

Arg Ala Leu Ala Arg Ala Leu Ala Arg Ala Leu Arg Ala Leu Ala Arg
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: targeting peptide TMTP-1

<400> SEQUENCE: 12

Asn Val Val Arg Gln
1               5

<210> SEQ ID NO 13
<211> LENGTH: 5
<212> TYPE: PRT
<213> ORGANISM: Artificial Sequence
<220> FEATURE:
<223> OTHER INFORMATION: spacer

<400> SEQUENCE: 13

Glu Ala Ala Ala Lys
1               5

<210> SEQ ID NO 14
<211> LENGTH: 60
<212> TYPE: PRT
<213> ORGANISM: Artificial Sequence
<220> FEATURE:
<223> OTHER INFORMATION: Targeting Peptide-alpha helical spacer (four
      repeats)-RALA

<400> SEQUENCE: 14

Asn Val Val Arg Gln Leu Ala Glu Ala Ala Ala Lys Glu Ala Ala Ala
1               5                   10                  15

```
Lys Glu Ala Ala Ala Lys Glu Ala Ala Ala Lys Ala Ala Trp Glu
            20                  25                  30

Ala Arg Leu Ala Arg Ala Leu Ala Arg Ala Leu Ala Arg His Leu Ala
        35                  40                  45

Arg Ala Leu Ala Arg Ala Leu Arg Ala Cys Glu Ala
    50                  55                  60

<210> SEQ ID NO 15
<211> LENGTH: 14
<212> TYPE: PRT
<213> ORGANISM: Artificial Sequence
<220> FEATURE:
<223> OTHER INFORMATION: Consensus Sequence

<400> SEQUENCE: 15

Glu Ala Arg Leu Ala Arg Ala Leu Ala Arg Ala Leu Ala Arg
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Consensus Sequence

<400> SEQUENCE: 16

Leu Ala Arg Ala Leu Ala Arg Ala Leu Arg Ala
1               5                   10

<210> SEQ ID NO 17
<211> LENGTH: 30
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (1)..(1)
<223> OTHER INFORMATION: Xaa is Trp or Arg
<220> FEATURE:
<221> NAME/KEY: MISC_FEATURE
<222> LOCATION: (16)..(16)
<223> OTHER INFORMATION: Xaa is Optional or selected from His or Glu
<220> FEATURE:
<221> NAME/KEY: MISC_FEATURE
<222> LOCATION: (28)..(28)
<223> OTHER INFORMATION: Xaa is Cys or Arg

<400> SEQUENCE: 17

Xaa Glu Ala Arg Leu Ala Arg Ala Leu Ala Arg Ala Leu Ala Arg Xaa
1               5                   10                  15

Leu Ala Arg Ala Leu Ala Arg Ala Leu Arg Ala Xaa Glu Ala
            20                  25                  30

<210> SEQ ID NO 18
<211> LENGTH: 20
<212> TYPE: PRT
<213> ORGANISM: Artificial Sequence
<220> FEATURE:
<223> OTHER INFORMATION: alpha helical spacer (four repeats)

<400> SEQUENCE: 18

Glu Ala Ala Ala Lys Glu Ala Ala Ala Lys Glu Ala Ala Ala Lys Glu
1               5                   10                  15

Ala Ala Ala Lys
            20
```

We claim:

1. An amphipathic cell penetrating peptide of less than 50 amino acid residues comprising at least 6 arginine residues (R), at least 12 alanine residues (A), at least 6 leucine residues (L), optionally at least one cysteine residue (C) and at least two but no greater than three glutamic acids (E) wherein
   - the arginine (R) residues are evenly distributed along the length of the peptide;
   - the ratio of arginine (R) to negatively charged glutamic acid (E) residues is from at least 6:2 to 9:2; and
   - the ratio of hydrophilic amino acid residues to hydrophobic amino acid residues at pH 7 is at least 30:67 to 40:60; or
   - wherein the peptide comprises or consists of WEARLARALARALARELARALARALRACEA (SEQ ID No. 4).

2. An amphipathic cell penetrating peptide of less than 50 amino acid residues comprising at least 6 arginine residues (R), at least 12 alanine residues (A), at least 6 leucine residues (L), optionally at least one cysteine residue (C), and at least two but no greater than three glutamic acids (E) wherein
   - (a) the arginine (R) residues are evenly distributed along the length of the peptide;
   - the ratio of arginine (R) to negatively charged glutamic acid (E) residues is from at least 6:2 to 8:2; and
       - the ratio of hydrophilic amino acid residues to hydrophobic amino acid residues at pH 7 is at least 30:70 to 40:60 ; or
       - wherein the peptide comprises or consists of WEARLARALARELARALARALRACEA (SEQ ID No. 4).

3. The amphipathic cell penetrating peptide according to claim 1 or 2 wherein said peptide does not comprise glycine.

4. The peptide according to claim 1 or 2 comprising a consensus sequence selected from EARLARALARALAR (SEQ NO No. 15) and LARALARALRA (SEQ ID No. 16).

5. The peptide according to claim 1 or 2 comprising or consisting of the amino acid sequence X-EARLARALARALAR-Y-LARALARALRA-Z-EA (SEQ ID No. 17 ), wherein
   X is W or R;
   Y is optional or selected from H or E; and
   Z is C or R;
   or a sequence with at least 80% sequence identity or homology.

6. The peptide according to claim 1 or 2 comprising or consisting of one of the following amino acid sequences:

```
                                          (SEQ ID No. 1)
WEARLARALARALARHLARALARALRACEA (SEQ ID No. 2)
WEARLARALARALARLARALARALRACEA (SEQ ID No. 3)
WEARLARALARALARLARALARALRACEA (SEQ ID No. 5)
REARLARALARALARLARALARALRACEA (SEQ ID No. 6)
REARLARALARALARLARALARALRAREA (SEQ ID No. 7)
REARLARALARALARELARALARALRAREA
``` or a fragment thereof.

7. A peptide according to claim 1 or 2 wherein the peptide comprises or consists of the following amino acid sequence WEARLARALARALARHLARALARALRACEA (SEQ ID No. 1).

8. The peptide according to claim 3 wherein said peptide is coupled to a polyethylene glycol (PEG) molecule or comprising a cell targeting motif sequence conjugated to the peptide via a spacer sequence.

9. The peptide according to claim 8 comprising the cell targeting motif sequence conjugated to the peptide via the spacer sequence wherein the cell targeting motif is the metastatic prostate cancer targeting peptide TMTP-1 (NVVRQ) (SEQ ID No. 12) and the spacer is an alpha helical spacer comprising from 1 to 4 repeats of the sequence EAAAK (SEQ ID No. 13).

10. A cell delivery system comprising the peptide of claim 1 or 2 complexed with a nucleic acid or other agent, wherein the other agent is a negatively charged or hydrophilic compound.

11. The cell delivery system according to claim 10 wherein the nucleic acid is inducible nitric oxide synthase (iNOS) plasmid DNA under the control of a tumour specific promoter selected from the human osteocalcin (hOC) promoter, osteopontin promoter, WAF1, CARG and a prostate specific promoter.

12. The cell delivery system according to claim 10 wherein the other agent is a small molecule agent.

13. The cell delivery system according to claim 12 wherein the small molecule agent is a phosphate based drug selected from alendronate, etidronate, zolendrate or any other nitrogen or non-nitrogen based bisphosphonate drug.

14. A method for the nuclear localisation of nucleic acids selected from DNA, RNA, shRNA, or siRNA, to cells comprising providing and administering the cell delivery system of claim 10 to said cells.

15. A method of improving the bioavailability of a phosphate based drug to an individual, comprising the administration of a nanoparticle comprising the peptide of claim 1 or 2 complexed with a negatively charged or hydrophilic compound being a phosphate based drug, to an individual in need thereof.

16. A method of improving the cellular uptake of gold to an individual in need thereof comprising the administration of a nanoparticle comprising the peptide of claim 1 or 2 complexed with a negatively charged or hydrophilic compound being gold, to an individual.

17. A pharmaceutical composition comprising the peptide of claim 1 or 2 and a suitable pharmaceutical excipient.

* * * * *